(12) United States Patent  
Boronkay et al.

(10) Patent No.: US 9,752,185 B2  
(45) Date of Patent: Sep. 5, 2017

(54) MICROFLUIDIC DEVICES

(71) Applicant: IntegenX Inc., Pleasanton, CA (US)

(72) Inventors: Allen Boronkay, San Jose, CA (US); Stevan Bogdan Jovanovich, Livermore, CA (US); Iuliu Ioan Blaga, Fremont, CA (US)

(73) Assignee: IntegenX Inc., Pleasanton, CA (US)

( * ) Notice: Subject to any disclaimer, the term of this patent is extended or adjusted under 35 U.S.C. 154(b) by 0 days.

(21) Appl. No.: 14/824,333

(22) Filed: Aug. 12, 2015

(65) Prior Publication Data

US 2016/0053314 A1  Feb. 25, 2016

Related U.S. Application Data

(63) Continuation of application No. 13/896,581, filed on May 17, 2013, now abandoned, which is a (Continued)

(51) Int. Cl.  
*C12M 1/00* (2006.01)  
*C12M 1/34* (2006.01)  
(Continued)

(52) U.S. Cl.  
CPC ........ *C12Q 1/6869* (2013.01); *B01F 11/0071* (2013.01); *B01F 13/0059* (2013.01); (Continued)

(58) Field of Classification Search  
CPC .... C12C 1/68; C12M 1/00; B01L 3/50; B01L 7/52  
(Continued)

(56) References Cited

U.S. PATENT DOCUMENTS 3,075,740 A   1/1963  McIntosh  
3,190,310 A   6/1965  Honsinger  
(Continued)

FOREIGN PATENT DOCUMENTS

CA   2433145 A1   5/2002  
CN   1109597 A    10/1995  
(Continued)

OTHER PUBLICATIONS

Krsek et al , Comparison of different methods for the isolation and purification of total community DNA from soil, 1999, Journal of Microbiological Methods 39, 1-16.*

(Continued)

*Primary Examiner* — Narayan Bhat  
(74) *Attorney, Agent, or Firm* — Wilson Sonsini Goodrich & Rosati

(57) ABSTRACT

Methods and devices for the interfacing of microchips to various types of modules are disclosed. The technology disclosed can be used as sample preparation and analysis systems for various applications, such as DNA sequencing and genotyping, proteomics, pathogen detection, diagnostics and biodefense. Also disclosed in the present disclosure is a flow through, traveling-wave, bead-beating device which comprises a rotating pole piece, a flow through tube, and a magnetic piece. Rotation of the rotating pole piece may create a magnetic wave down the flow through tube, thereby producing sufficient acceleration of beads through the tube to disrupt or lyse target analytes flowing through the tube.

8 Claims, 38 Drawing Sheets

Related U.S. Application Data continuation of application No. 12/815,685, filed on Jun. 15, 2010, now Pat. No. 8,476,063, which is a continuation of application No. 11/670,866, filed on Feb. 2, 2007, now Pat. No. 7,745,207, said application No. 12/815,685 is a continuation-in-part of application No. 11/229,065, filed on Sep. 15, 2005, now abandoned.

(60) Provisional application No. 60/764,980, filed on Feb. 3, 2006, provisional application No. 60/609,970, filed on Sep. 15, 2004.

(51) Int. Cl.

| | | |
|---|---|---|
| *G01N 15/06* | (2006.01) | |
| *B01J 19/08* | (2006.01) | |
| *B01J 19/12* | (2006.01) | |
| *B01D 21/00* | (2006.01) | |
| *C12Q 1/68* | (2006.01) | |
| *B01F 11/00* | (2006.01) | |
| *B01F 13/00* | (2006.01) | |
| *C12Q 1/24* | (2006.01) | |
| *C12Q 1/70* | (2006.01) | |
| *C12N 15/10* | (2006.01) | |
| *B01L 3/00* | (2006.01) | |
| *B01L 7/00* | (2006.01) | |
| *B01L 9/00* | (2006.01) | |
| *G01N 35/00* | (2006.01) | |

(52) U.S. Cl.
CPC ....... *B01L 3/5027* (2013.01); *B01L 3/502715* (2013.01); *B01L 3/502753* (2013.01); *C12N 15/1003* (2013.01); *C12N 15/1013* (2013.01); *C12Q 1/24* (2013.01); *C12Q 1/686* (2013.01); *C12Q 1/6806* (2013.01); *C12Q 1/6844* (2013.01); *C12Q 1/70* (2013.01); *B01L 3/5025* (2013.01); *B01L 3/502738* (2013.01); *B01L 3/502761* (2013.01); *B01L 7/52* (2013.01); *B01L 9/527* (2013.01); *B01L 2200/027* (2013.01); *B01L 2200/028* (2013.01); *B01L 2200/0668* (2013.01); *B01L 2200/10* (2013.01); *B01L 2300/0627* (2013.01); *B01L 2300/0636* (2013.01); *B01L 2300/0654* (2013.01); *B01L 2300/0803* (2013.01); *B01L 2300/087* (2013.01); *B01L 2300/0816* (2013.01); *B01L 2300/0864* (2013.01); *B01L 2300/0867* (2013.01); *B01L 2300/0874* (2013.01); *B01L 2300/0887* (2013.01); *B01L 2300/1822* (2013.01); *B01L 2300/1827* (2013.01); *B01L 2300/1844* (2013.01); *B01L 2400/0415* (2013.01); *B01L 2400/0421* (2013.01); *B01L 2400/0481* (2013.01); *B01L 2400/0655* (2013.01); *G01N 2035/00514* (2013.01); *Y10T 436/163333* (2015.01); *Y10T 436/25875* (2015.01)

(58) Field of Classification Search
USPC ........ 435/6.1, 283.1, 287.2, 288.5; 422/68.1, 422/186.01, 527
See application file for complete search history.

(56) References Cited

U.S. PATENT DOCUMENTS

| | | | |
|---|---|---|---|
| 3,352,643 A | 11/1967 | Ando et al. | |
| 3,433,257 A | 3/1969 | Jensen | |
| 3,568,692 A | 3/1971 | Metzger et al. | |
| 3,610,274 A | 10/1971 | Levesque et al. | |
| 3,662,517 A | 5/1972 | Tascher et al. | |
| 4,011,357 A | 3/1977 | Haase | |
| 4,113,665 A | 9/1978 | Law et al. | |
| 4,390,307 A * | 6/1983 | Rice | E02D 7/00 173/117 |
| 4,558,845 A | 12/1985 | Hunkapiller | |
| 4,703,913 A | 11/1987 | Hunkapiller | |
| 4,847,120 A | 7/1989 | Gent | |
| 4,963,498 A | 10/1990 | Hillman et al. | |
| 5,085,757 A | 2/1992 | Karger et al. | |
| 5,275,645 A | 1/1994 | Ternoir et al. | |
| 5,338,427 A | 8/1994 | Shartle et al. | |
| 5,364,759 A | 11/1994 | Caskey et al. | |
| 5,376,252 A | 12/1994 | Ekstroem et al. | |
| 5,387,505 A | 2/1995 | Wu | |
| 5,453,163 A | 9/1995 | Yan | |
| 5,482,836 A | 1/1996 | Cantor et al. | |
| 5,523,231 A | 6/1996 | Reeve | |
| 5,571,410 A | 11/1996 | Swedberg et al. | |
| 5,587,128 A | 12/1996 | Wilding et al. | |
| 5,589,136 A | 12/1996 | Northrup et al. | |
| 5,635,358 A | 6/1997 | Wilding et al. | |
| 5,639,428 A | 6/1997 | Cottingham | |
| 5,675,155 A | 10/1997 | Pentoney, Jr. et al. | |
| 5,681,946 A | 10/1997 | Reeve | |
| 5,705,628 A | 1/1998 | Hawkins | |
| 5,705,813 A | 1/1998 | Apffel et al. | |
| 5,726,026 A | 3/1998 | Wilding et al. | |
| 5,741,462 A | 4/1998 | Nova et al. | |
| 5,750,015 A | 5/1998 | Soane et al. | |
| 5,770,029 A | 6/1998 | Nelson et al. | |
| 5,775,371 A | 7/1998 | Pan et al. | |
| 5,776,748 A | 7/1998 | Singhvi et al. | |
| 5,830,662 A | 11/1998 | Soares et al. | |
| 5,842,787 A | 12/1998 | Kopf-Sill et al. | |
| 5,856,174 A | 1/1999 | Lipshutz et al. | |
| 5,863,502 A | 1/1999 | Southgate et al. | |
| 5,872,010 A | 2/1999 | Karger et al. | |
| 5,885,470 A | 3/1999 | Parce et al. | |
| 5,898,071 A | 4/1999 | Hawkins | |
| 5,900,130 A | 5/1999 | Benvegnu et al. | |
| 5,908,552 A | 6/1999 | Dittmann et al. | |
| 5,922,591 A | 7/1999 | Anderson et al. | |
| 5,942,443 A | 8/1999 | Parce et al. | |
| 5,948,684 A | 9/1999 | Weigl et al. | |
| 5,951,262 A * | 9/1999 | Hartman | F04D 1/06 417/356 |
| 5,971,158 A | 10/1999 | Yager et al. | |
| 5,994,064 A | 11/1999 | Staub et al. | |
| 6,001,229 A | 12/1999 | Ramsey | |
| 6,007,690 A | 12/1999 | Nelson et al. | |
| 6,007,775 A | 12/1999 | Yager | |
| 6,010,607 A | 1/2000 | Ramsey | |
| 6,048,100 A | 4/2000 | Thrall et al. | |
| 6,056,860 A | 5/2000 | Amigo et al. | |
| 6,073,482 A | 6/2000 | Moles | |
| 6,074,827 A | 6/2000 | Nelson et al. | |
| 6,103,199 A | 8/2000 | Bjornson et al. | |
| 6,110,343 A | 8/2000 | Ramsey et al. | |
| 6,120,184 A | 9/2000 | Laurence et al. | |
| 6,136,212 A | 10/2000 | Mastrangelo et al. | |
| 6,153,389 A | 11/2000 | Haarer et al. | |
| 6,168,948 B1 | 1/2001 | Anderson et al. | |
| 6,176,962 B1 | 1/2001 | Soane et al. | |
| 6,190,616 B1 | 2/2001 | Jovanovich et al. | |
| 6,197,595 B1 | 3/2001 | Anderson et al. | |
| 6,207,031 B1 | 3/2001 | Adourian et al. | |
| 6,235,471 B1 | 5/2001 | Knapp et al. | |
| 6,238,538 B1 | 5/2001 | Parce et al. | |
| 6,251,343 B1 | 6/2001 | Dubrow et al. | |
| 6,280,589 B1 | 8/2001 | Manz et al. | |
| 6,319,476 B1 | 11/2001 | Victor, Jr. et al. | |
| 6,321,791 B1 | 11/2001 | Chow | |
| 6,322,683 B1 | 11/2001 | Wolk et al. | |
| 6,326,068 B1 | 12/2001 | Kong et al. | |
| 6,342,142 B1 | 1/2002 | Ramsey | |
| 6,348,318 B1 | 2/2002 | Valkirs | |
| 6,379,929 B1 | 4/2002 | Burns et al. | |

(56) References Cited

U.S. PATENT DOCUMENTS

| | | |
|---|---|---|
| 6,387,234 B1 | 5/2002 | Yeung et al. |
| 6,387,707 B1 | 5/2002 | Seul et al. |
| 6,391,622 B1 | 5/2002 | Knapp et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,461,492 B1 | 10/2002 | Hayashizaki et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | McKernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,620,584 B1 | 9/2003 | Chee et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,660,148 B2 | 12/2003 | Shoji et al. |
| 6,663,833 B1 | 12/2003 | Stave et al. |
| 6,685,442 B2 | 2/2004 | Chinn et al. |
| 6,685,678 B2 | 2/2004 | Evans et al. |
| 6,685,809 B1 | 2/2004 | Jacobson et al. |
| 6,705,345 B1 | 3/2004 | Bifano |
| 6,740,219 B2 | 5/2004 | Imai et al. |
| 6,752,922 B2 | 6/2004 | Huang et al. |
| 6,764,648 B1 | 7/2004 | Roach et al. |
| 6,782,746 B1 | 8/2004 | Hasselbrink, Jr. et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,883,774 B2 | 4/2005 | Nielsen et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,052 B2 | 2/2006 | Shimizu et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,063,304 B2 | 6/2006 | Leys |
| 7,081,191 B2 | 7/2006 | Shoji et al. |
| 7,087,380 B2 | 8/2006 | Griffiths et al. |
| 7,097,809 B2 | 8/2006 | Van Dam et al. |
| 7,105,300 B2 | 9/2006 | Parce et al. |
| 7,118,910 B2 | 10/2006 | Unger et al. |
| 7,142,987 B2 | 11/2006 | Eggers |
| 7,157,228 B2 | 1/2007 | Hashmi et al. |
| 7,169,557 B2 | 1/2007 | Rosenblum et al. |
| 7,170,050 B2 | 1/2007 | Turner et al. |
| 7,198,759 B2 | 4/2007 | Bryning et al. |
| 7,211,388 B2 | 5/2007 | Cash et al |
| 7,217,367 B2 | 5/2007 | Huang et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,244,961 B2 | 7/2007 | Jovanovich et al. |
| 7,258,744 B2 | 8/2007 | Sakurada et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,318,912 B2 | 1/2008 | Pezzuto et al. |
| 7,323,305 B2 | 1/2008 | Leamon et al. |
| 7,329,388 B2 | 2/2008 | Guzman |
| 7,361,471 B2 | 4/2008 | Gerdes et al. |
| 7,377,483 B2 | 5/2008 | Iwabuchi et al. |
| 7,416,165 B2 | 8/2008 | Ohmi et al. |
| 7,419,578 B2 | 9/2008 | Sakai et al. |
| 7,438,856 B2 | 10/2008 | Jedrzejewski et al. |
| 7,445,926 B2 | 11/2008 | Mathies et al. |
| 7,473,342 B2 | 1/2009 | Ugai et al. |
| 7,486,865 B2 | 2/2009 | Foquet et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,531,076 B2 | 5/2009 | Hayashizaki et al. |
| 7,537,886 B1 | 5/2009 | Nazarenko et al. |
| 7,575,865 B2 | 8/2009 | Leamon et al. |
| 7,584,240 B2 | 9/2009 | Eggers |
| 7,589,184 B2 | 9/2009 | Hogan et al. |
| 7,645,580 B2 | 1/2010 | Barber et al. |
| 7,691,614 B2 | 4/2010 | Senapathy |
| 7,704,735 B2 | 4/2010 | Facer et al. |
| 7,718,442 B2 | 5/2010 | Davis et al. |
| 7,744,737 B1 | 6/2010 | James et al. |
| 7,745,207 B2 | 6/2010 | Jovanovich et al. |
| 7,749,365 B2 | 7/2010 | Nguyen et al. |
| 7,749,737 B2 | 7/2010 | McBride et al. |
| 7,763,453 B2 | 7/2010 | Clemmens et al. |
| 7,766,033 B2 | 8/2010 | Mathies et al. |
| 7,785,458 B2 | 8/2010 | Shimizu et al. |
| 7,790,368 B1 | 9/2010 | Fukuzono |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,972,561 B2 | 7/2011 | Viovy et al. |
| 7,976,789 B2 | 7/2011 | Kenis et al. |
| 7,976,795 B2 | 7/2011 | Zhou et al. |
| 7,998,708 B2 | 8/2011 | Handique et al. |
| 8,007,746 B2 | 8/2011 | Unger et al. |
| 8,018,593 B2 | 9/2011 | Tan et al. |
| 8,034,628 B2 | 10/2011 | Harrison et al. |
| 8,037,903 B2 | 10/2011 | Wang et al. |
| 8,053,192 B2 | 11/2011 | Bignell et al. |
| RE43,122 E | 1/2012 | Harrison et al. |
| 8,142,635 B2 | 3/2012 | Shimizu et al. |
| 8,221,990 B2 | 7/2012 | Mori et al. |
| 8,222,023 B2 | 7/2012 | Battrell et al. |
| 8,268,263 B2 | 9/2012 | Campbell et al. |
| 8,283,165 B2 | 10/2012 | Hogan et al. |
| 8,313,941 B2 | 11/2012 | Takayama et al. |
| 8,337,777 B2 | 12/2012 | Nurse et al. |
| 8,388,908 B2 | 3/2013 | Blaga et al. |

(56) References Cited

U.S. PATENT DOCUMENTS

| | | |
|---|---|---|
| 8,394,642 B2 | 3/2013 | Jovanovich et al. |
| 8,398,642 B2 | 3/2013 | Weekes |
| 8,420,318 B2 | 4/2013 | Mathies et al. |
| 8,431,340 B2 | 4/2013 | Jovanovich et al. |
| 8,431,384 B2 | 4/2013 | Hogan et al. |
| 8,431,390 B2 | 4/2013 | Jovanovich et al. |
| 8,476,063 B2 | 7/2013 | Jovanovich et al. |
| 8,501,305 B2 | 8/2013 | Barlow |
| 8,512,538 B2 | 8/2013 | Majlof et al. |
| 8,551,714 B2 | 10/2013 | Jovanovich et al. |
| 8,557,518 B2 | 10/2013 | Jovanovich et al. |
| 8,562,918 B2 | 10/2013 | Jovanovich et al. |
| 8,584,703 B2 | 11/2013 | Kobrin et al. |
| 8,672,532 B2 | 3/2014 | Jovanovich et al. |
| 8,748,165 B2 | 6/2014 | Vangbo et al. |
| 8,763,642 B2 | 7/2014 | Vangbo |
| 8,841,116 B2 | 9/2014 | Mathies et al. |
| 8,894,946 B2 | 11/2014 | Nielsen et al. |
| 9,012,236 B2 | 4/2015 | Jovanovich et al. |
| 9,121,058 B2 | 9/2015 | Jovanovich et al. |
| 9,341,284 B2 | 5/2016 | Vangbo |
| 9,592,501 B2 | 3/2017 | Jarvius et al. |
| 9,663,819 B2 | 5/2017 | Jovanovich et al. |
| 2001/0012612 A1 | 8/2001 | Petersen et al. |
| 2001/0041357 A1 | 11/2001 | Fouillet et al. |
| 2002/0003895 A1 | 1/2002 | Some |
| 2002/0022261 A1 | 2/2002 | Anderson et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0042125 A1 | 4/2002 | Petersen et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0055167 A1 | 5/2002 | Pourahmadi et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0115201 A1 | 8/2002 | Barenburg et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0137039 A1 | 9/2002 | Gessner |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0151089 A1 | 10/2002 | Chapman et al. |
| 2002/0157951 A1 | 10/2002 | Foret et al. |
| 2002/0160361 A1 | 10/2002 | Loehrlein et al. |
| 2002/0187560 A1 | 12/2002 | Pezzuto et al. |
| 2003/0008308 A1 | 1/2003 | Enzelberger et al. |
| 2003/0019753 A1 | 1/2003 | Ogle et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0077839 A1 | 4/2003 | Takei |
| 2003/0087425 A1 | 5/2003 | Eggers |
| 2003/0087446 A1 | 5/2003 | Eggers |
| 2003/0087455 A1 | 5/2003 | Eggers et al. |
| 2003/0088657 A1 | 5/2003 | Eggers |
| 2003/0095897 A1 | 5/2003 | Grate et al. |
| 2003/0104466 A1 | 6/2003 | Knapp et al. |
| 2003/0129755 A1 | 7/2003 | Sadler et al. |
| 2003/0162304 A1 | 8/2003 | Dority et al. |
| 2003/0175706 A1 | 9/2003 | Zhang |
| 2003/0197139 A1 | 10/2003 | Williams |
| 2003/0198573 A1 | 10/2003 | Forood et al. |
| 2003/0215369 A1 | 11/2003 | Eggers et al. |
| 2003/0217923 A1 | 11/2003 | Harrison et al. |
| 2004/0003997 A1 | 1/2004 | Anazawa et al. |
| 2004/0013536 A1 | 1/2004 | Hower et al. |
| 2004/0014091 A1 | 1/2004 | Duck et al. |
| 2004/0018611 A1 | 1/2004 | Ward et al. |
| 2004/0021068 A1 | 2/2004 | Staats |
| 2004/0022676 A1 | 2/2004 | Hamilton et al. |
| 2004/0037739 A1 | 2/2004 | McNeely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086427 A1 | 5/2004 | Childers et al. |
| 2004/0086870 A1 | 5/2004 | Tyvoll et al. |
| 2004/0086872 A1 | 5/2004 | Childers et al. |
| 2004/0101966 A1 | 5/2004 | Davis et al. |
| 2004/0132170 A1 | 7/2004 | Storek et al. |
| 2004/0146452 A1 | 7/2004 | Fujieda et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0217004 A1 | 11/2004 | Hayashizaki et al. |
| 2004/0219533 A1 | 11/2004 | Davis et al. |
| 2004/0224380 A1 | 11/2004 | Chou et al. |
| 2005/0026181 A1 | 2/2005 | Davis et al. |
| 2005/0026300 A1 | 2/2005 | Samper et al. |
| 2005/0042656 A1 | 2/2005 | Davis et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0181394 A1 | 8/2005 | Steemers et al. |
| 2005/0201901 A1 | 9/2005 | Grossman et al. |
| 2005/0221373 A1 | 10/2005 | Enzelberger et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0250199 A1 | 11/2005 | Anderson et al. |
| 2005/0255000 A1 | 11/2005 | Yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0014177 A1 | 1/2006 | Hogan et al. |
| 2006/0027456 A1 | 2/2006 | Harrison et al. |
| 2006/0040300 A1 | 2/2006 | Dapprich et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0177832 A1 | 8/2006 | Brenner |
| 2006/0186043 A1 | 8/2006 | Covey et al. |
| 2006/0210994 A1 | 9/2006 | Joyce |
| 2006/0210998 A1 | 9/2006 | Kettlitz et al. |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0020654 A1 | 1/2007 | Blume et al. |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0113908 A1 | 5/2007 | Lee et al. |
| 2007/0122819 A1 | 5/2007 | Wu et al. |
| 2007/0175756 A1 | 8/2007 | Nguyen et al. |
| 2007/0183935 A1 | 8/2007 | Clemmens et al. |
| 2007/0184463 A1 | 8/2007 | Molho et al. |
| 2007/0184547 A1 | 8/2007 | Handique et al. |
| 2007/0202531 A1 | 8/2007 | Grover et al. |
| 2007/0218485 A1 | 9/2007 | Davis et al. |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0263049 A1 | 11/2007 | Preckel et al. |
| 2007/0289941 A1 | 12/2007 | Davies et al. |
| 2007/0292941 A1 | 12/2007 | Handique et al. |
| 2007/0297947 A1 | 12/2007 | Sommers et al. |
| 2008/0014576 A1 | 1/2008 | Jovanovich et al. |
| 2008/0014589 A1 | 1/2008 | Link et al. |

(56) References Cited

U.S. PATENT DOCUMENTS

| | | |
|---|---|---|
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0131904 A1 | 6/2008 | Parce et al. |
| 2008/0138809 A1 | 6/2008 | Kapur et al. |
| 2008/0160630 A1 | 7/2008 | Liu et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0217178 A1 | 9/2008 | Ben-Asouli et al. |
| 2008/0237146 A1 | 10/2008 | Harrison et al. |
| 2008/0241844 A1 | 10/2008 | Kellogg |
| 2008/0242560 A1 | 10/2008 | Gunderson et al. |
| 2008/0257437 A1 | 10/2008 | Fernandes et al. |
| 2008/0262747 A1 | 10/2008 | Kain et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0020427 A1 | 1/2009 | Tan et al. |
| 2009/0023603 A1 | 1/2009 | Selden et al. |
| 2009/0026082 A1 | 1/2009 | Rothberg et al. |
| 2009/0035770 A1 | 2/2009 | Mathies et al. |
| 2009/0053799 A1 | 2/2009 | Chang-Yen et al. |
| 2009/0056822 A1 | 3/2009 | Young et al. |
| 2009/0059222 A1 | 3/2009 | Tan et al. |
| 2009/0060797 A1 | 3/2009 | Mathies et al. |
| 2009/0084679 A1 | 4/2009 | Harrison et al. |
| 2009/0087850 A1 | 4/2009 | Eid et al. |
| 2009/0092970 A1 | 4/2009 | Williams |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1 | 7/2009 | Jarvius et al. |
| 2009/0181411 A1 | 7/2009 | Battrell et al. |
| 2009/0183990 A1 | 7/2009 | Shoji et al. |
| 2009/0233325 A1 | 9/2009 | Mori et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | McBrady et al. |
| 2009/0314970 A1 | 12/2009 | McAvoy et al. |
| 2009/0314972 A1 | 12/2009 | McAvoy et al. |
| 2009/0325183 A1 | 12/2009 | Lao et al. |
| 2009/0325276 A1 | 12/2009 | Battrell et al. |
| 2009/0325277 A1 | 12/2009 | Shigeura et al. |
| 2010/0010472 A1 | 1/2010 | Moore |
| 2010/0035252 A1 | 2/2010 | Rothberg et al. |
| 2010/0068723 A1 | 3/2010 | Jovanovich et al. |
| 2010/0075858 A1 | 3/2010 | Davis et al. |
| 2010/0092948 A1 | 4/2010 | Davis et al. |
| 2010/0093068 A1 | 4/2010 | Williams et al. |
| 2010/0111770 A1 | 5/2010 | Hwang et al. |
| 2010/0129810 A1 | 5/2010 | Greiner et al. |
| 2010/0137143 A1 | 6/2010 | Rothberg et al. |
| 2010/0165784 A1 | 7/2010 | Jovanovich et al. |
| 2010/0172898 A1 | 7/2010 | Doyle et al. |
| 2010/0173392 A1 | 7/2010 | Davis et al. |
| 2010/0173398 A1 | 7/2010 | Peterman |
| 2010/0178210 A1 | 7/2010 | Hogan et al. |
| 2010/0197507 A1 | 8/2010 | Rothberg et al. |
| 2010/0209957 A1 | 8/2010 | Hogan et al. |
| 2010/0210008 A1 | 8/2010 | Strand et al. |
| 2010/0218623 A1 | 9/2010 | Eggers et al. |
| 2010/0221726 A1 | 9/2010 | Zenhausern et al. |
| 2010/0224255 A1 | 9/2010 | Mathies et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0248363 A1 | 9/2010 | Hogan et al. |
| 2010/0252123 A1 | 10/2010 | Mathies et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0304986 A1 | 12/2010 | Chen et al. |
| 2010/0326826 A1 | 12/2010 | Harrison et al. |
| 2011/0003301 A1 | 1/2011 | Raymond et al. |
| 2011/0005932 A1 | 1/2011 | Jovanovich et al. |
| 2011/0008785 A1 | 1/2011 | Tan et al. |
| 2011/0008813 A1 | 1/2011 | Dilleen et al. |
| 2011/0020920 A1 | 1/2011 | Mathies et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0041935 A1 | 2/2011 | Zhou et al. |
| 2011/0045505 A1 | 2/2011 | Warthoe et al. |
| 2011/0048945 A1 | 3/2011 | Harrison et al. |
| 2011/0053784 A1 | 3/2011 | Unger et al. |
| 2011/0070578 A1 | 3/2011 | Bell et al. |
| 2011/0076735 A1 | 3/2011 | Jovanovich et al. |
| 2011/0124049 A1 | 5/2011 | Li et al. |
| 2011/0126910 A1 | 6/2011 | May |
| 2011/0126911 A1 | 6/2011 | Kobrin et al. |
| 2011/0127222 A1 | 6/2011 | Chang-Yen et al. |
| 2011/0136179 A1 | 6/2011 | Bin/Lee et al. |
| 2011/0137018 A1 | 6/2011 | Chang-Yen et al. |
| 2011/0171086 A1 | 7/2011 | Prins et al. |
| 2011/0172403 A1 | 7/2011 | Harrold |
| 2011/0186466 A1 | 8/2011 | Kurowski et al. |
| 2011/0189678 A1 | 8/2011 | McBride et al. |
| 2011/0195495 A1 | 8/2011 | Selden et al. |
| 2011/0206576 A1 | 8/2011 | Woudenberg et al. |
| 2011/0207140 A1 | 8/2011 | Handique et al. |
| 2011/0212440 A1 | 9/2011 | Viovy et al. |
| 2011/0212446 A1 | 9/2011 | Wang et al. |
| 2011/0220502 A1 | 9/2011 | Selden et al. |
| 2011/0223605 A1 | 9/2011 | Bienvenue et al. |
| 2011/0229897 A1 | 9/2011 | Bell et al. |
| 2011/0229898 A1 | 9/2011 | Bell et al. |
| 2011/0240127 A1 | 10/2011 | Eberhart et al. |
| 2011/0256530 A1 | 10/2011 | Hogan |
| 2011/0290648 A1 | 12/2011 | Majlof et al. |
| 2011/0312614 A1 | 12/2011 | Selden et al. |
| 2012/0055798 A1 | 3/2012 | Selden et al. |
| 2012/0088249 A1 | 4/2012 | Jovanovich et al. |
| 2012/0100522 A1 | 4/2012 | Saghbini et al. |
| 2012/0115189 A1 | 5/2012 | Jovanovich et al. |
| 2012/0164036 A1 | 6/2012 | Stern et al. |
| 2012/0181460 A1 | 7/2012 | Eberhart et al. |
| 2012/0240127 A1 | 9/2012 | Brittenham et al. |
| 2012/0267247 A1 | 10/2012 | Tan et al. |
| 2012/0279638 A1 | 11/2012 | Zhou et al. |
| 2012/0290648 A1 | 11/2012 | Sharkey |
| 2012/0308987 A1 | 12/2012 | Hogan et al. |
| 2012/0309637 A1 | 12/2012 | Schumm et al. |
| 2012/0315635 A1 | 12/2012 | Vangbo et al. |
| 2012/0322666 A1 | 12/2012 | Pham et al. |
| 2013/0029338 A1 | 1/2013 | Jovanovich et al. |
| 2013/0053255 A1 | 2/2013 | Vangbo et al. |
| 2013/0074944 A1 | 3/2013 | Van Gelder |
| 2013/0084565 A1 | 4/2013 | Landers et al. |
| 2013/0105017 A1 | 5/2013 | Zhou et al. |
| 2013/0115607 A1 | 5/2013 | Nielsen et al. |
| 2013/0139895 A1 | 6/2013 | Vangbo |
| 2013/0203634 A1 | 8/2013 | Jovanovich et al. |
| 2013/0210129 A1 | 8/2013 | Selden et al. |
| 2013/0213810 A1 | 8/2013 | Tan et al. |
| 2013/0217026 A1 | 8/2013 | Egan et al. |
| 2013/0224846 A1 | 8/2013 | Jovanovich et al. |
| 2013/0240140 A1 | 9/2013 | Kurowski et al. |
| 2013/0260380 A1 | 10/2013 | Hall et al. |
| 2013/0344475 A1 | 12/2013 | Jovanovich et al. |
| 2014/0045704 A1 | 2/2014 | Jovanovich et al. |
| 2014/0065628 A1 | 3/2014 | Van Gelder et al. |
| 2014/0065689 A1 | 3/2014 | Hogan et al. |
| 2014/0073043 A1 | 3/2014 | Holmes |
| 2014/0161686 A1 | 6/2014 | Bort et al. |
| 2014/0170645 A1 | 6/2014 | Jovanovich et al. |
| 2014/0246618 A1 | 9/2014 | Zhou et al. |

(56) References Cited

U.S. PATENT DOCUMENTS

| | | |
|---|---|---|
| 2014/0370519 A1 | 12/2014 | Vangbo et al. |
| 2015/0021502 A1 | 1/2015 | Vangbo |
| 2015/0024436 A1 | 1/2015 | Eberhart et al. |
| 2015/0136602 A1 | 5/2015 | Jovanovich et al. |
| 2015/0136604 A1 | 5/2015 | Nielsen et al. |
| 2016/0016140 A1 | 1/2016 | Jovanovich et al. |
| 2016/0096176 A1 | 4/2016 | Jarvius et al. |
| 2016/0116439 A1 | 4/2016 | Kindwall et al. |
| 2016/0305972 A1 | 10/2016 | Ogg et al. |
| 2016/0367981 A1 | 12/2016 | Wunderle et al. |
| 2017/0002399 A1 | 1/2017 | Eberhart et al. |

FOREIGN PATENT DOCUMENTS

| | | |
|---|---|---|
| CN | 1146017 A | 3/1997 |
| CN | 1354692 A | 6/2002 |
| CN | 1593338 A | 3/2005 |
| CN | 101004423 A | 7/2007 |
| CN | 101312759 A | 11/2008 |
| EP | 0459241 B1 | 10/1994 |
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1345697 B1 | 6/2007 |
| EP | 1658890 B1 | 5/2008 |
| EP | 1345551 B1 | 4/2009 |
| EP | 2345739 A2 | 7/2011 |
| EP | 2345739 A3 | 10/2011 |
| JP | H08327594 A | 12/1996 |
| JP | H10206384 A | 8/1998 |
| JP | 2001500966 A | 1/2001 |
| JP | 2001521818 A | 11/2001 |
| JP | 2002370200 A | 12/2002 |
| JP | 2003074462 A | 3/2003 |
| JP | 2003536058 A | 12/2003 |
| JP | 2004025159 A | 1/2004 |
| JP | 2004108285 A | 4/2004 |
| JP | 2004180594 A | 7/2004 |
| JP | 2005323519 A | 11/2005 |
| JP | 2005337415 A | 12/2005 |
| JP | 2005345463 A | 12/2005 |
| JP | 2007506430 A | 3/2007 |
| JP | 2007155491 A | 6/2007 |
| JP | 2007198765 A | 8/2007 |
| JP | 2008513022 A | 5/2008 |
| WO | WO-9322053 A1 | 11/1993 |
| WO | WO-9604547 A1 | 2/1996 |
| WO | WO-9614934 A1 | 5/1996 |
| WO | WO-9810277 A1 | 3/1998 |
| WO | WO-9852691 A1 | 11/1998 |
| WO | WO-9853300 A2 | 11/1998 |
| WO | WO-9853300 A3 | 2/1999 |
| WO | WO-9922868 A1 | 5/1999 |
| WO | WO-9933559 A1 | 7/1999 |
| WO | WO-9936766 A1 | 7/1999 |
| WO | WO-9940174 A1 | 8/1999 |
| WO | WO-0040712 A1 | 7/2000 |
| WO | WO-0060362 A1 | 10/2000 |
| WO | WO-0061198 A1 | 10/2000 |
| WO | WO-0101025 A2 | 1/2001 |
| WO | WO-0132930 A1 | 5/2001 |
| WO | WO-0138865 A1 | 5/2001 |
| WO | WO-0101025 A3 | 7/2001 |
| WO | WO-0185341 A1 | 11/2001 |
| WO | WO-0192575 A1 | 12/2001 |
| WO | WO-0224949 A1 | 3/2002 |
| WO | WO-0241995 A1 | 5/2002 |
| WO | WO-0243615 A2 | 6/2002 |
| WO | WO-0243864 A2 | 6/2002 |
| WO | WO-0243864 A3 | 8/2002 |
| WO | WO-0243615 A3 | 3/2003 |
| WO | WO-03044528 A2 | 5/2003 |
| WO | WO-03062462 A2 | 7/2003 |
| WO | WO-03085379 A2 | 10/2003 |
| WO | WO-03085379 A3 | 12/2003 |
| WO | WO-2004038363 A2 | 5/2004 |
| WO | WO-03044528 A3 | 6/2004 |
| WO | WO-2004061085 A2 | 7/2004 |
| WO | WO-2004062804 A1 | 7/2004 |
| WO | WO-2004080597 A2 | 9/2004 |
| WO | WO-2004061085 A3 | 10/2004 |
| WO | WO-2004098757 A2 | 11/2004 |
| WO | WO-2004038363 A3 | 12/2004 |
| WO | WO-2005072858 A1 | 8/2005 |
| WO | WO-2005075081 A1 | 8/2005 |
| WO | WO-2005091820 A2 | 10/2005 |
| WO | WO-2005108620 A2 | 11/2005 |
| WO | WO-2005118867 A2 | 12/2005 |
| WO | WO-2005121308 A1 | 12/2005 |
| WO | WO-2005123950 A2 | 12/2005 |
| WO | WO-2006032044 A2 | 3/2006 |
| WO | WO-2005108620 A3 | 4/2006 |
| WO | WO-2004098757 A3 | 5/2006 |
| WO | WO-2005091820 A3 | 10/2006 |
| WO | WO-2006032044 A3 | 1/2007 |
| WO | WO-2007002579 A2 | 1/2007 |
| WO | WO-2007064635 A1 | 6/2007 |
| WO | WO-2007082480 A1 | 7/2007 |
| WO | WO-2007109375 A2 | 9/2007 |
| WO | WO-2005118867 A3 | 12/2007 |
| WO | WO-2008012104 A2 | 1/2008 |
| WO | WO-2008024319 A2 | 2/2008 |
| WO | WO-2008030631 A2 | 3/2008 |
| WO | WO-2008024319 A3 | 4/2008 |
| WO | WO-2008039875 A1 | 4/2008 |
| WO | WO-2008012104 A3 | 5/2008 |
| WO | WO-2008115626 A2 | 9/2008 |
| WO | WO-2007109375 A3 | 10/2008 |
| WO | WO-2008115626 A3 | 11/2008 |
| WO | WO-2009008236 A1 | 1/2009 |
| WO | WO-2009015296 A1 | 1/2009 |
| WO | WO-2007002579 A3 | 9/2009 |
| WO | WO-2009108260 A2 | 9/2009 |
| WO | WO-2009129415 A1 | 10/2009 |
| WO | WO-2009108260 A3 | 12/2009 |
| WO | WO-2010041174 A1 | 4/2010 |
| WO | WO-2010041231 A2 | 4/2010 |
| WO | WO-2010042784 A3 | 7/2010 |
| WO | WO-2010041231 A3 | 9/2010 |
| WO | WO-2010109392 A1 | 9/2010 |
| WO | WO-2010130762 A2 | 11/2010 |
| WO | WO-2010141921 A1 | 12/2010 |
| WO | WO-2011003941 A1 | 1/2011 |
| WO | WO-2011011172 A1 | 1/2011 |
| WO | WO-2010130762 A3 | 2/2011 |
| WO | WO-2011012621 A1 | 2/2011 |
| WO | WO-2011034621 A2 | 3/2011 |
| WO | WO-2011056215 A1 | 5/2011 |
| WO | WO-2011084703 A2 | 7/2011 |
| WO | WO-2011094577 A2 | 8/2011 |
| WO | WO-2011034621 A3 | 11/2011 |
| WO | WO-2011084703 A3 | 12/2011 |
| WO | WO-2012024657 A1 | 2/2012 |
| WO | WO-2012024658 A2 | 2/2012 |
| WO | WO-2012136333 A2 | 10/2012 |
| WO | WO-2013130910 A1 | 9/2013 |
| WO | WO-2014014587 A2 | 1/2014 |
| WO | WO-2014055936 A1 | 4/2014 |

OTHER PUBLICATIONS

Allowed Claims dated May 6, 2010 for U.S. Appl. No. 11/726,701.
Allowed Claims dated Jul. 1, 2010 for U.S. Appl. No. 11/139,018.
Allowed Claims dated Aug. 13, 2008 for U.S. Appl. No. 10/750,533.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Armani, et al. Re-configurable fluid circuits by PDMS elastomer micromachining. Proceedings of IEEE Micro Electro Mechanical Systems: MEMS. 1999; 222-227.

(56) References Cited

OTHER PUBLICATIONS

Auroux, et al. Micro Total Analysis Systems 2. Analytical Standard Operations and Applications. Anal. Chem. 2002; 2637-2652.
Belgrader, et al. A Minisonicator to Rapidly Disrupt Bacterial Spores for DNA Analysis. Anal. Che. 1999; 4232-4236.
Belgrader, et al. PCR Detection of Bacteria in Seven Minutes. Science Magazin. 1999; 284(5413):449-450.
Belgrader, et al. Rapid PCR for Identity Testing Using a Battery-Powered Miniature Thermal Cycler. J Forensic Sci. 1998; 315-319.
Bennett, et al. Toward the 1,000 dollars human genome. Pharmacogenomics, 6 (4) 373-382. (Jun. 2005).
Bianco, et al. Teflon-like coatings for micro devices. CPAC Satellite Workshops. Rome, Italy. Mar. 23, 2009.
Bings, et al. Microfluidic Devices Connected to Fused-Silica Capillaries with Minimal Dead Dead Volume. Analytical Chemistry. 1999;71(15):3292-3296.
Birnboim. A Rapid Alkaline Extraction Method for the Isolation of Plasmid DNA. Methods of Enzymology. 1983; 100:243-255.
Blaga, et al. Microfluidic device for automated sample preparation. Poster. MSB Conference. Dalian, China. Oct. 2009.
Blaga, et al. Plastic chips with valves and pumps. MSB Conference. Berlin, Germany. Mar. 2008. Abstract only.
Blazej, et al. Inline injection microdevice for attomole-scale sanger DNA sequencing. Anal Chem. Jun. 15, 2007;79(12):4499-506. Epub May 12, 2007.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Brenner, et al. Gene expression analysis by massively parallel signature sequencing (MPSS) on microbead arrays. Nature Biotechnology, 18: 630-634 (2000).
Buchholz, et al. The use of light scattering for precise characterization of polymers for DNA sequencing by capillary electrophoresis. Electrophoresis. 2001;22:4118-4128.
Burns, et al. An Integrated Nanoliter DBA Analysis Device. Science Magazine. 1998; 484-487.
Call, et al. Detecting and genotyping *Escherichia coli* 0157:H7 using multiplexed PCR and nucleic acid microarrays. International Journal of Food Microbiology. 2001; 67:71-80.
Cameron, et al. High Internal Phase Emulsions (HIPEs) Structure, Properties and Use in Polymer Preparation. University of Strathclyde. 1995; 163-214.
Canadian Office Action dated Jun. 10, 2011 for CA Application No. 2512071.
Capanu, et al. Design Fabrication and Testing of a Bistable Electromagnetically Actuated Microvalve. Journal of Microeclectromechanical System. 2000; 9:181-189.
CAPLUS abstract of Krohkin et al. Modified silica as a stationary phase for ion chromatography. Journal of Chromatography A. 1995;706:93-8.
Chan, et al. Microfabricated Polymer Devices for Automated Sample Delivery of Peptides for Analysis by Electrospray Ionization Tandem Mass Spectrometry. Analytical Chemistry. 1999;71(20):4437-4444.
Chandler, et al. Automated immunomagnetic separation and microarray detection of *E. coli* 0157:H7 from poultry carcass rinse. International Journal of Food Microbiology. 2001; 70:143-154.
Charlieu, et al. 3' Alu PCR: a simple and rapid method to isolate human polymorphic markers. Nucleic Acids Res. Mar. 25, 1992;20(6):1333-7.
Chiem, et al. Microchip systems for immunoassay: an integrated immunoreactor with electrophoretic separation for serum theophylline determination. Clinical Chemistry.1998;44(3):591-598.
Chiem, et al. Room temperature bonding of micromachined glass devices for capillary electrophoresis. Sensors and Actuators. 2000;B63(3):147-152.

Chinese office action dated Jan. 18, 2012 for CN 200980108368.7. (in Chinese with English translation).
Chinese Office Action dated Jan. 25, 2008 for Application No. 2003801100666.
Chinese office action dated Jan. 31, 2011 for CN 200580035911.7. (in Chinese with English translation).
Chinese office action dated Feb. 24, 2010 for CN Application No. 200780018073.1.
Chinese office action dated Jul. 8, 2011 for CN 200580035911.7. (in Chinese with English translation).
Coleman, et al. A sequential injection microfluidic mixing strategy. Microfluidics and Nanofluidics. 2005;319-327.
Co-pending U.S. Appl. No. 14/659,108, filed Mar. 16, 2015.
Co-pending U.S. Appl. No. 14/919,620, filed Oct. 21, 2015.
Co-pending U.S. Appl. No. 15/037,039, filed May 16, 2016.
Co-pending U.S. Appl. No. 15/117,053, filed Aug. 5, 2016.
Co-pending U.S. Appl. No. 15/154,086, filed May 13, 2016.
Curcio, et al. Continuous Segmented-Flow Polymerase Chain Reaction for High-Throughput Miniaturized DNA Amplification. Analytical Chemistry. 2003;75(1):1-7.
Datasheet Cycle Sequencing, Retrieved from the internet, URL:http//answers.com/topic/cyclesequencing. Printed Sep. 3, 2010, pp. 1-2.
Delehanty, et al. A Microarray Immunoassay for Simultaneous Detection of Proteins and Bacteria. Anal. Chem. 2002; 74:5681-5687.
Diehl et al. BEAMing: single-molecule PCR on microparticles in water-in-oil emulsions. Nature Methods 3(7):551-559 (2006).
Dodson, et al. Fluidics Cube for Biosensor Miniaturization. Anal. Chem. 2001; 3776-3780.
Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.
Doherty, et al. Sparsely cross-linked "nanogels" for microchannel DNA sequencing. Electrophoresis. 2003;24(24):4170-4180.
Dorfman, et al. Contamination-Free Continuous Flow Microfluidic Polymerase Chain Reaction for Quantitative and Clinical Applications. Analytical Chemistry. 2005;77(11):3700-3704.
Doyle, et al. Self-Assembled Magnetic Matrices for DNA Separation Chips. Science. 2000;295:2237.
Dressman, et al. Transforming single DNA molecules into fluorescent magnetic particles for detection and enumeration of genetic variations. Proc Natl Acad Sci USA. 2003;100(15):8817-8822.
Duffy, et al. Rapid Prototyping of Microfluidic Systems in Poly(dimethylsiloxane). Anal. Chem. 1998; 4974-4984.
Emrich, et al. Microfabricated 384-Lane Capillary Array Electrophoresis Bioanalyzer for Ultrahigh-Throughput Genetic Analysis. Analytical Chemistry. 2002;74(19):5076-5083.
Ericson, et al. Electroosmosis- and Pressure-Driven Chromatography in Chips Using Continuous Beds. Analytical Chemistry. 2000;72(1):81-87.
Erratum for Margulies, et al. Genome sequencing in microfabricated high-density picolitre reactors. Nature. 2005;437(7057):376-80.
European office action dated Apr. 7, 2011 for EP Application No. 05804847.1.
European search report and search opinion dated Jun. 6, 2011 for Application No. 10011511.2.
European search report and search opinion dated Aug. 17, 2011 for Application No. 08799648.4.
European search report dated Oct. 29, 2012 for EP Application No. 07853470.8.
European search report dated Dec. 18, 2009 for Application No. 03808583.3.
European search report dated Sep. 1, 2010 for Application No. 5804847.1.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.

(56) References Cited

OTHER PUBLICATIONS

Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Franklin, et al. Apollo 200: an integrated platform for DNA profiling. Poster. MCB Conference. Prague, Czech Republic. Mar. 2010.
Fuentes, et al. Detecting minimal traces of DNA using DNA covalently attached to superparamagnetic nanoparticles and direct PCR-ELISA. Biosens Bioelectron. Feb. 15, 2006;21(8):1574-80. Epub Aug. 29, 2005.
Gau, et al. A MEMS based amperometric detector for E. coli bacteria using self-assembled monolayers. Biosensors & Bioelectronic. 2001; 16:745-755.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;689:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Hansen, et al. Polymerase chain reaction assay for the detection of Bacillus cereus group cells. Fems Microbology Letters. 2001; 202:209-213.
Harrison, et al. Micromachining a Miniaturized Capillary Electrophoresis-Based Chemical Analysis System on a Chip. Science. 1993;261(5123):895-897.
Hartmann, et al. Direct immobilization of antibodies on phthalocyaninato-polysiloxane photopolymers. Thin Solid Films. 1994; 245:206-210.
Hartmann, et al. One-step immobilization of immunoglobulin G and potential of the method for application in immunosensors. Sensors and Actuators. 1995; 28 (2):143-149.
Hayes, et al. EDGE: A Centralized Resource for the Comparison, Analysis, and Distribution of Toxicogenomic Information. Molecular Pharmacology. 2005;67(4):1360-1368.
He, et al. Fabrication of Nanocolumns for Liquid Chromatography. Anal. Chem. 1998; 3790-3797.
Heath, et al. PCR primed with VNTR core sequences yields species specific patterns and hypervariable probes. Nucleic Acids Res. Dec. 11, 1993;21(24):5782-5.
Hjerten. High-performance electrophoresis : Elimination of electroendosmosis and solute adsorption. J. Chromotography. 1985; 347:191-198.
Hosokawa, et al. A Pneumatically-Actuated Three-Way Microvalve Fabricated with Polydimcthylsiloxanc Using the Membrane Transfer Technique. J. Micinicch. Microcng. 2000; 10:415-420.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/02721 dated Aug. 5, 2008.
International Preliminary Report for corresponding PCT Application No. PCT/US2007/061573 dated Aug. 26, 2008.
International search report and written opinion dated Oct. 29, 2007 for PCT/US2005/018678.
International search report and written opinion dated Jan. 5, 2012 for PCT Application No. US2011/048527.
International search report and written opinion dated Mar. 16, 2012 for PCT/US2011/048528.
International search report and written opinion dated Mar. 24, 2011 for PCT Application No. US2010/58227.
International search report and written opinion dated Apr. 30, 2012 for PCT/US2012/021217.
International search report and written opinion dated Jun. 9, 2011 for PCT Application No. US2011/30973.
International search report and written opinion dated Jul. 15, 2008 for PCT/US2007/007381.
International search report and written opinion dated Sep. 1, 2010 for PCT Application No. US2010/040490.
International search report and written opinion dated Oct. 26, 2011 for PCT Application No. US11/38180.
International search report dated Sep. 1, 2010 for PCT/US2010/040490.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.
International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 23, 2006 for PCT Application No. US2005/033347.
International search report dated Aug. 26, 2004 PCT Application No. US2003/41466.
International search report dated Sep. 25, 2007 for PCT Application No. US2007/02721.
International Search Report for PCT/US2005/033347.
International written opinion dated Oct. 6, 2010 for PCT Application No. US10/37545.
International written opinion report dated Jul. 30, 2010 for PCT Application No. US2010/36464.
Jacobson, et al. Electrokinetic Focusing in Microfabricated Channel Structures. Anal. Chem., 1997, 69 (16), pp. 3212-3217.
Jacobson, et al. High-Speed Separations on a Microchip. Anal. Chem. 1994; 1114-1118.
Jacobson, et al. Integrated Microdevice for DNA Restriction Fragment Analysis Anal. Chem. 1996; 720-723.
Japanese office action dated Jan. 5, 2012 for Application No. 2007-532553 (in Japanese with English translation).
Japanese Office Action dated Jan. 13, 2010 for JP Application No. 2005-508628.

(56) References Cited

OTHER PUBLICATIONS

Japanese office action dated Mar. 1, 2011 for JP Application. No. 2007-515379.
Japanese office action dated May 11, 2012 for Application No. 2008-553535 (English translation).
Japanese office action dated May 27, 2011 for Application No. 2007-532553 (in Japanese with English translation).
Japanese office action dated Jul. 28, 2011 for Application No. 2008-553535 (in Japanese with English translation).
Japanese Office Action dated Aug. 10, 2010 for JP Application No. 2005-508628.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
Ju, et al. Fluorescence energy transfer dye-labeled primers for DNA sequencing and analysis. Proc. Natl. Acad. Sci. USA. 1995;92:4347-4351.
Kamei, et al. Integrated Amorphous Silicon Photodiode Detector for Microfabricaqted Capillary Electrophoresis Devices. Micro Total Analysis Systems. 2002; 257-259.
Kamei, et al. Integrated hydrogenated amorphous Si photodiode detector for microfluidic bioanalytical devices. Anal Chem. Oct. 15, 2003;75(20):5300-5.
Kan, et al. A novel thermogelling matrix for microchannel DNA sequencing based on poly-N-alkoxyalkylaclylamide copolymers. Electrophoresis. 2003;24(24):4161-4169.
Kimura, et al. Restriction-Site-Specific PCR as a Rapid Test to Detect Enterohemorrhagic *Escherichia coli* 0157:H7 Strains in Environmental Samples. Applied and Environmental Microbiology. Jun. 2000; 2513-2519.
Koch, et al. Optical flow-cell multichannel immunosensor for the detection of biological warfare agents. Biosens Bioelectron. Jan. 2000;14(10-11):779-84.
Koh, et al. Integrating Polymerase Chain Reaction, Valving, and Electrophoresis in a Plastic Device for Bacterial Detection. Analytical Chemistry. 2003;75(17):4591-4598.
Kong, et al. Rapid detection of six types of bacterial pathogens in marine waters by multiplex PCR. Water Research. 2002; 36: 2802-2812.
Kopp, et al. Chemical Amplification Continuous-Flow PCR on a Chip. Science. 1998;280:1046-1048.
Korean office action dated Mar. 5, 2012 for KR 10-2007-7008423. (in Korean with English translation).
Kourentzi, et al. Microbial identification by immunohybridization assay of artificial RNA labels. Journal of Microbiological Methods. 2002; 49:301-306.
Kuhnert, et al. Detection System for *Escherichia coli*-Specific Virulence Genes: Absence of Virulence Determinants in B and C Strains. applied and Environmental Microbiology. 1997:703-709.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;663(3)138-146.
Lagally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Lee, et al. Polymer nanoengineering for biomedical applications. Annals Biomed. Eng. 2006; 34:75-88.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole-time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Ligler, et al. Integrating Waveguide Biosensor. Anal Chem. Feb. 1, 2002;74(3):713-9.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Lu, et al. New valve and bonding designs for microfluidic biochips containing proteins. Anal. Chem. 2007; 79:994-1001.
Manz, et al. Miniaturized Total Chemical Analysis Systems: A Novel Concept for Chemical Sensing. Sensors & Actuators. 1990; 244-248.
McLaughlin, et al. Molecular Approaches to the Identification of Streptococci. Methods in Molecular Medicine. 1998; 15:117-139.
Medintz, et al. Genotyping Energy-Transfer Cassette Labeled Short Tandem Repeat Amplicons with Capillary Array Electrophoresis Microchannel Plates. Clinical Chemistry. 2001; 1614-1621.
Medintz, et al. High-Performance Genetic Analysis Using Microfabricated Capillary Array Electroporesis Microplates. Electrophoresis. 2001; 3845-3856.
Medintz, et al. High-Performance Multiplex SNP Analysis of Three Hemochmromatosis-Related Mutations with Capillary Array Electrophoresis Microplates. Genome Research. 2001; 413-421.
Medintz, et al. Novel Energy Transfer Fluorescence Labeling Cassette. BioTechniques. 2002; 32(2):270.
Melin, et al. A Passive 2-Dimensional Liquid Sample Micromixer. 7th International Conference on Miniaturized Chemical and Biochemical Analysis Systems. 2003;167-170.
MillGat pump user manual, version 2.12, published 2005, pp. 1-28.
Mitra, et al. Digital genotyping and haplotyping with polymerase colonies. Proc Natl Acad Sci USA. 2003.100(10):15926-5931.
Nataro, et al. Diarrheagenic *Escherichia coli*. Clinical MicroBiology Reviews. Jan. 1998;142-201.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.
Notice of allowance dated Apr. 25, 2013 for U.S. Appl. No. 12/815,685.
Notice of allowance dated May 3, 2010 for U.S. Appl. No. 11/670,866.
Notice of Allowance dated May 6, 2010 for U.S. Appl. No. 11/726,701.
Notice of allowance dated Jun. 9, 2011 for U.S. Appl. No. 12/831,949.
Notice of Allowance dated Jul. 1, 2010 for U.S. Appl. No. 11/139,018.
Notice of Allowance dated Aug. 13, 2008 for U.S. Appl. No. 10/750,533.
Notice of allowance dated Sep. 8, 2011 for U.S. Appl. No. 12/820,390.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.

(56) References Cited

OTHER PUBLICATIONS

Office action dated Jan. 7, 2011 for U.S. Appl. No. 12/844,544.
Office action dated Jan. 20, 2010 for U.S. Appl. No. 11/978,224.
Office action dated Feb. 22, 2010 for U.S. Appl. No. 11/139,018.
Office action dated Mar. 2, 2008 for U.S. Appl. No. 10/540,658.
Office action dated Mar. 19, 2009 for U.S. Appl. No. 11/670,866.
Office action dated Mar. 24, 2010 for U.S. Appl. No. 11/670,866.
Office action dated Mar. 29, 2012 for U.S. Appl. No. 12/789,186.
Office action dated Mar. 30, 2012 for U.S. Appl. No. 12/795,515.
Office action dated Apr. 11, 2012 for U.S. Appl. No. 11/139,018.
Office action dated Apr. 15, 2015 for U.S. Appl. No. 13/896,581.
Office action dated Apr. 29, 2009 for U.S. Appl. No. 11/139,018.
Office action dated May 22, 2012 for U.S. Appl. No. 12/526,015.
Office action dated Jun. 18, 2012 for U.S. Appl. No. 12/815,685.
Office action dated Aug. 23, 2012 for U.S. Appl. No. 13/287,398.
Office action dated Aug. 27, 2008 for U.S. Appl. No. 11/139,018.
Office action dated Aug. 29, 2012 for U.S. Appl. No. 12/605,217.
Office action dated Oct. 8, 2008 for U.S. Appl. No. 10/540,658.
Office action dated Oct. 25, 2010 for U.S. Appl. No. 11/978,224.
Office action dated Nov. 6, 2009 for U.S. Appl. No. 11/139,018.
Office action dated Dec. 11, 2009 for U.S. Appl. No. 11/726,701.
Office Action Final dated Feb. 6, 2008 issued in U.S. Appl. No. 11/139,018.
Office Action mailed Apr. 27, 2007 in U.S. Appl. No. 11/139,018, filed May 25, 2005.
Office Action mailed Jul. 2, 2007 in U.S. Appl. No. 10/540,658, filed Jun. 23, 2005.
Office Action mailed Jul. 12, 2007 in U.S. Appl. No. 10/750,533, filed Dec. 29, 2003.
Oh, et al. A review of microvalves. J. Micromech. Microeng. 2006; 16:R13-R39.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
O'Mahony, et al. A real time PCR assay for the detection and quantitation of *Mycobacterium avium* subsp. *paratuberculosis* using SyBR Green and the Light Cycler. Journal of Microbiological Methods. 2002; 51:283-293.
Paegel, et al. High-throughput DNA sequencing with a 96-lane capillary array electrophoresis bioprocessor. Proc Natl Acad Sci USA. 2002;99:574-579.
Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
Papadelli, et al. Rapid detection and identification of *Streptococcus macedonicus* by species-specific PCR and DNA hybridisation. International Journal of Food Microbiology. 2003; 81:231-239.
PCT Notification of Transmittal of the International Search Report and the Written Opinion of the International Searching Authority, or the Declaration, mailed Jun. 17, 2008, Application No. PCT/US2007/082568.
Peng, et al. Immuno-capture PCR for detection of Aeromonas hydrophila Journal of Microbiological Methods. 2002; 49:335-338.
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.

Press, et al., An Integrated Microfluidic Processor for Single Nucleotide Polymorphism-based DNA Computing, Lab on a Chip. 2005, 5:10, 8 pages.
Press, et al., The Art of Scientific Computing, Numerical Recipes in C, 2nd Edition, Cambridge University Press, 1992, (table of Contents).
Quake, et al. From Micro-to Nanofabrication with Soft Materials. Science Magazine. 2000; 1536-1540.
Ramsey, et al. Generating Electrospray from Microchip Devices Using Electroosmotic Pumping. Analytical Chemistry. 1997;69(6):1174-1178.
Reyes, et al. Micro Total Analysis Systems. 1. Introduction Theory and Technology. Anal Chem. 2002; 2623-2636.
Rohr, et al. Porous polymer monoliths: Simple and efficient mixers prepared by direct polymerization in the channels of microfluidic chips. Electrophoresis. 2001;22:3959-3967.
Roth, et al. Fundamentals of Logic Design, 3rd Edition, West Publishing Company, 1985 (Table of Content).
Rowe, et al. Array Biosensor for Simultaneous Identification of Bacterial, Viral and Protein Analytes. Anal. Chem. 1999; 71:3846-3852.
Rowe-Taitt, et al., Simultaneous detection of six biohazardous agents using a planar waveguide array biosensor. Biosensors & Bioelectronics. 2000; 15:579-589.
Ruan, et al. Immunobiosensor Chips for Detection of *Escherichia coli* 0157:H7 Using Electrochemical Impedance Spectroscopy. Anal. Chem. 2002; 74:4814-4820.
Rye, et al. High-sensitivity two-color detection of double-stranded DNA with a confocal fluorescence gel scanner using ethidium homodimer and thiazole orange. Nucleic Acids Research. 1991;19(2):327-333.
Samel. Novel Microfluidic devices based on a thermally responsive PDMS composite. KTH Royal Institute of Technology, Stockholm, Sweden. 2007; 1-80.
Sanford, et al. Photoactivatable Cross-Linked Polyacrylamide for the Site-Selective Immobilization of Antigens and Antibodies Chem Mater. 1998; 10(6): 1510-1520.
Scherer, et al. High-Pressure Gel Loader for Capillary Array Electrophoresis Microchannel Plates. Biotechniques. 2001;31(5):1150-1154.
Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Shaikh, et al. A modular microfluidic architecture for integrated biochemical analysis. Proc Natl Acad Sci U S A. Jul. 12, 2005;102(28):9745-50. Epub Jun. 28, 2005.
Shi, et al. Radial Capillary Array Electrophoresis Microplate and Scanner for High Performance Nucleic Acid Analysis. Anal. Chem. 1999; 5354-5361.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Polymeric Microelectro-mechanical Systems. Anal. Chem 2000; 643-651.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Stumpfle, et al. Absence of DNA sequence homology with genes of the *Excherichia coli* hemB locus in Shiga-toxin producing *E. coli* (STEC) 0157 Strains. FEMS Microbiology Letters. 1999; 174:97-103.
Sun, et al. A Heater-Integrated Transparent Microchannel Chip for Continuous Flow PCR. Sensors and Actuators B. 2002; 84:283-289.

(56) References Cited

OTHER PUBLICATIONS

Tajima, et al. Physiochemical properties and morphology of fluorocarbon films synthesized on crosslinked polyethylene by capacitively coupled octafluorocyclobutane plasma. J. Phys. Chem. C. 2007; 111(11):4358-4367.
Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Tian, et al. Evaluation of Silica Resins for Direct and Efficient Extraction of DNA from Complex Biological Matrices in a Miniaturized Format. Analytical Biochemistry. 2000; 283:175-191.
Tice, et al. Formation of Droplets and Mixing in Multiphase Microfluidics at Low Values of the Reynolds and the Capillary Numbers. Langmuir. 2003;19:9127-9133.
Todd Thorsen, et al., "Microfluidic Large-Scale Integration", www.sciencemag.org, Science, vol. 298, Oct. 18, 2002, pp. 580-584.
U.S. Appl. No. 10/540,658 Office Action Final dated Feb. 19, 2008.
Reissue U.S. Appl. No. 90/011,453, filed Jan. 21, 2011.
Unpublished U.S. Appl. No. 13/367,326, filed Feb. 6, 2012.
Unpublished U.S. Appl. No. 13/384,753, filed Mar. 15, 2012.
Unpublished U.S. Appl. No. 13/896,581, filed May 17, 2013.
Unpublished U.S. Appl. No. 14/032,173, filed Sep. 10, 2013.
Unpublished U.S. Appl. No. 14/474,047, filed Aug. 29, 2014.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Vazquez, et al. Electrophoretic Injection within Microdevices. Analytical Chemistry. 2002;74:1952-1961.
Veenstra, et al. The design of an in-plane compliance structure for microfluidical systems. Sensors and Actuators. 2002;681:377-383.
Verlee, et al. .Fluid Circuit Technology: Integrated Interconnect Technology for Miniature Fluidic Devices. Abbott Laboratories Hospital Division, Abbott Park, IL. 1996; 9-14.
Waller, et al. Quantitative Immunocapture PCR Assay for Detection of Campylobacter jejuni in Foods. Applied Environmental Microbiology. 2000; 66(9):4115-4118.
Walt, et al. Biological Warefare Detection. Analytical Chemistry 2000; 739-746.
Waters, et al. Microchip Device for Cell Lysis, Multiplex PCR Amplification, and Electrophoretic Sizing. Anal. Chem. 1999; 158-162.
Webster, et al. Monolithic Capillary Electrophoresis Device with Integrated Flurorescence Detector. Anal. Chem. 2001;1622-1626.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
White, et al. Flash detection/identification of pathogens, bacterial spores and bioterrorism agent biomarker from clinical and environmental matrices. Journal of Microbiological Methods. 2002; 48:139-147.
Wikipedia brochure for defining stocahstic process. Sep. 2, 2009.
Williams, et al. Amplification of complex gene libraries by emulsion PCR. Nature Methods. 2006;3(7):545-50.
Willis, et al. Monolithic teflon membrane valves and pumps for harsh chemical and low-temperature use. Lab Chip. 2007; 7:1469-1474.
Woolley, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yacoub-George, et al. Chemiluminescence multichannel immunosensor for biodetection Analytica Chimica Acta. 2002; 457:3-12.
Yang, et al. A MEMS thermopneumatic silicone rubber membrane valve. Sensors and Actuators. 1998;A64(1):101-108.
Yang, et al. An Integrated Stacked Microlaboratory for Biological Agent Detection with DNA and Immunoassays. Biosensors & Bioelectronics. 2002; 17:605-618.
Yu, et al. Preparation of Monolithic Polymers with Controlled Porous Properties for Microfluidic Chip Applications Using Photoinitiated Free Radial Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
Zhang, et al. PMMA/PDMS valves and pumps for disposable microfluidics. Lap Chip. 2009; 9:3088-3094.
Zhu, et al. High-Sensitivity Capillary Electrophoresis of Double-Stranded DNA Fragments Using Monomeric and Dimeric Fluorescent Intercalating Dyes. Anal Chem. 1994; 1941-1948.
Co-pending U.S. Appl. No. 15/342,914, filed Nov. 3, 2016.
Office action dates Sep. 19, 2012 for U.S. Appl. No. 12/321,594.
Office action dates Dec. 7, 2012 for U.S. Appl. No. 13/590,051.
Office action dates Feb. 27, 2013 for U.S. Appl. No. 13/590,965.
Erratum for Margulies, et al. Genome sequencing in microfabricated high-density picolitre reactors. Nature. 2005;437(7057):376-80.: Margulies, et al. Nature. 441(7089):120. (May 4, 2006).
European search report dated Jul. 13, 2016 for EP Application No. 09714332.5.
Notice of allowance dated Feb. 19, 2013 for U.S. Appl. No. 12/845,650.
Notice of allowance dates Nov. 22, 2013 for U.S. Appl. No. 13/590,965.
Office action dated Jan. 13, 2017 for U.S. Appl. No. 14/253,622.
Office action dated Jan. 22, 2013 for U.S. Appl. No. 12/845,650.
Office action dated Jul. 1, 2016 for U.S. Appl. No. 14/253,622.
Office action dated Jul. 26, 2012 for U.S. Appl. No. 12/845,650.
Office action dated Aug. 24, 2012 for U.S. Appl. No. 12/026,510.
Office action dated Sep. 15, 2014 for U.S. Appl. No. 13/886,068.
Office action dated Nov. 14, 2012 for U.S. Appl. No. 12/526,015.
Office action dated Jan. 15, 2014 for U.S. Appl. No. 12/321,594.
Branton, et al. The potential and challenges of nanopore sequencing. Nat Biotechnol. Oct. 2008;26(10):1146-53. doi: 10.1038/nbt.1495.
Eid, et al. Real-time DNA sequencing from single polymerase molecules. Science. Jan. 2, 2009;323(5910):133-8. doi: 10.1126/science.1162986. Epub Nov. 20, 2008.
European search report and search opinion dated Jun. 22, 2016 for EP Application No. 11818879.6.
European search report and search opinion dated Sep. 11, 2013 for EP Application No. 10784213.

(56) References Cited

OTHER PUBLICATIONS

Fuller, et al. The challenges of sequencing by synthesis. Nat Biotechnol. Nov. 2009;27(11):1013-23. doi: 10.1038/nbt.1585. Epub Nov. 6, 2009.
Grodzinski, et al. Microfluidic System Integration in Sample Preparation Chip-Sets—a Summary. Conf. Proc. IEEE Eng. Med. Biol. Soc. 2004;4:2615-2618.
Holland, et al. Point-of-care molecular diagnostic systems—past, present and future. Curr Opin Microbiol. Oct. 2005;8(5):504-9.
International search report and written opinion dated Jan. 29, 2016 for PCT Application No. PCT/US2015/056764.
International search report and written opinion dated Mar. 3, 2015 for PCT Application No. PCT/US2014/066008.
International search report and written opinion dated Mar. 8, 2013 for PCT/US2012/061223.
International search report and written opinion dated Jul. 22, 2013 for PCT Application No. PCT/US2013/028462.
International search report and written opinion dated Oct. 26, 2015 for PCT/US2015/028510.
Lund-Olesen, et al. Capture of DNA in microfluidic channel using magnetic beads: Increasing capture efficiency with integrated microfluidic mixer. Journal of Magnetism and Magnetic Materials 311 (2007): 396-400.
Mamanova, et al. FRT-seq: amplification-free, strand-specific transcriptome sequencing. Nat Methods. Feb. 2010;7(2):130-2. doi: 10.1038/nmeth.1417. Epub Jan. 17, 2010.
Metzker, M. Sequencing technologies—the next generation. Nat Rev Genet. Jan. 2010;11(1):31-46. doi: 10.1038/nrg2626. Epub Dec. 8, 2009.
Notice of allowance dated Jan. 31, 2017 for U.S. Appl. No. 14/552,389.
Notice of allowance dated May 5, 2015 for U.S. Appl. No. 13/202,884.
Notice of allowance dated Jun. 25, 2014 for U.S. Appl. No. 13/656,503.
Notice of allowance dated Jul. 8, 2013 for U.S. Appl. No. 13/717,585.
Notice of allowance dated Nov. 12, 2014 for U.S. Appl. No. 13/967,957.
Notice of allowance dated Dec. 7, 2012 for U.S. Appl. No. 12/795,515.
Office action dated Jan. 17, 2014 for U.S. Appl. No. 13/656,503.
Office action dated Feb. 14, 2017 for U.S. Appl. No. 14/804,675.
Office action dated Feb. 28, 2013 for U.S. Appl. No. 13/113,968.
Office action dated Mar. 24, 2015 for U.S. Appl. No. 13/202,884.
Office action dated Apr. 1, 2014 for U.S. Appl. No. 13/202,884.
Office action dated May 30, 2014 for U.S. Appl. No. 13/656,503.
Office action dated Aug. 9, 2016 for U.S. Appl. No. 14/500,846.
Office action dated Sep. 11, 2014 for U.S. Appl. No. 13/967,957.
Office action dated Oct. 29, 2013 for U.S. Appl. No. 13/202,884.
Peoples, et al. Microfluidic Immunoaffinity Separations for Bioanalysis. J. Chromat. B. 2008;866:14-25 (available online Aug. 30, 2007).
Shendure, et al. Next-generation DNA sequencing. Nat Biotechnol. Oct. 2008;26(10):1135-45. doi: 10.1038/nbt1486.
Stevens, et al. Bacterial Separation and Concentration from Complex Sample Matrices: a Review. Crit. Rev. Microbiol. 2004;30(1):7-24.
Unger, et al. Monolithic microfabricated valves and pumps by multilayer soft lithography. Science. Apr. 7, 2000;288(5463):113-6.
U.S. Appl. No. 61/709,417, filed Oct. 4, 2012.
Van Ness, et al. Isothermal Reactions for the Amplification of Oligonucleotides. Proc. Nat. Acad. Sci. USA. 2003;100 (8):4504-4509.
Notice of allowance dated Jun. 12, 2017 for U.S. Appl. No. 14/804,675.

* cited by examiner

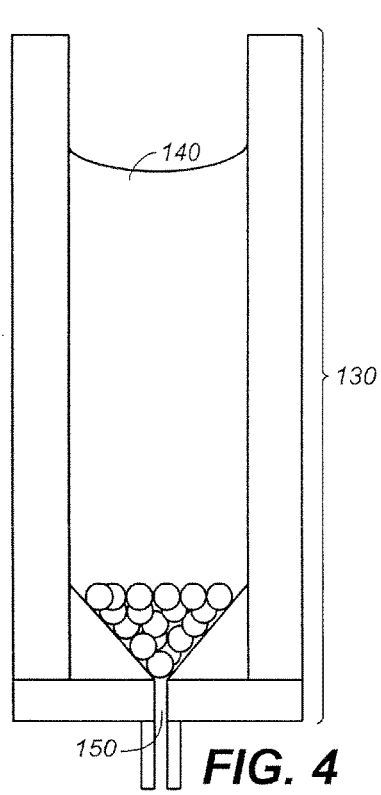
FIG. 4
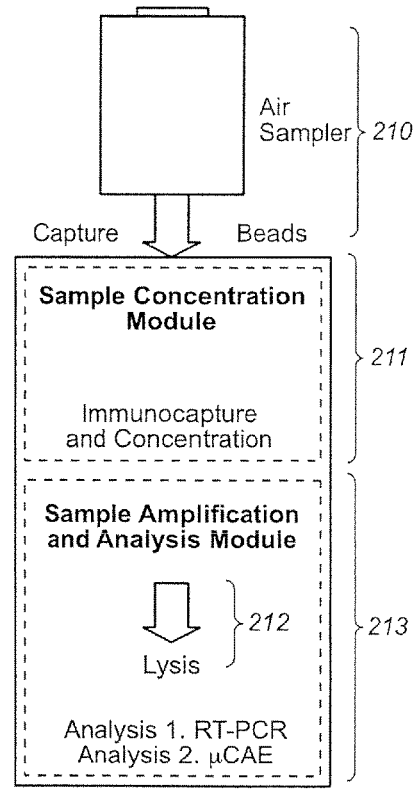
FIG. 8
FIG. 5
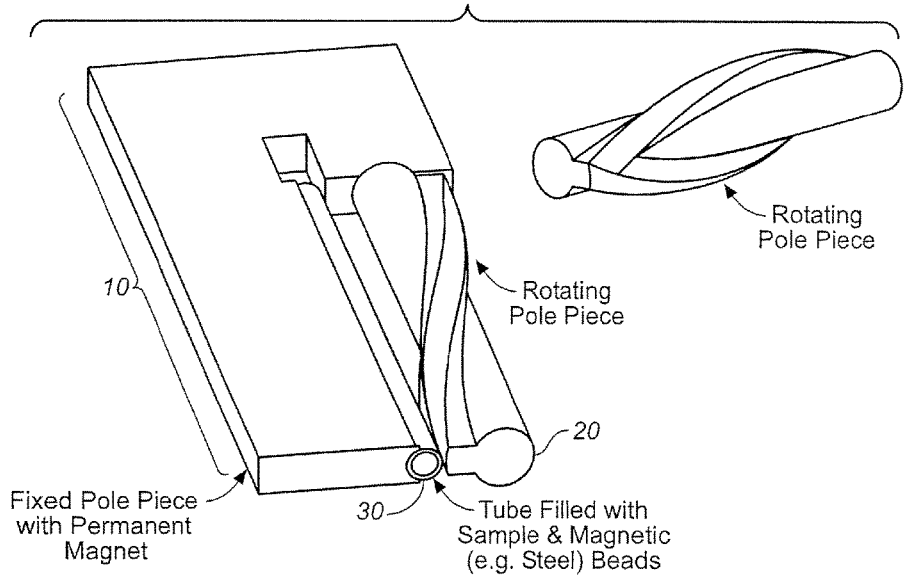

4-layer Topology
Valve Closed

Valve Open

MICROFLUIDIC DEVICES

CROSS REFERENCE TO RELATED APPLICATION

This application is a continuation of U.S. application Ser. No. 13/896,581, filed May 17, 2013; which is a continuation of U.S. application Ser. No. 12/815,685, filed Jun. 15, 2010 (U.S. Pat. No. 8,476,063); which is a continuation of U.S. application Ser. No. 11/670,866, filed Feb. 2, 2007 (U.S. Pat. No. 7,745,207); which is a non-provisional of U.S. provisional application No. 60/764,980, filed Feb. 3, 2006. U.S. application Ser. No. 12/815,685 is also a continuation-in-part of U.S. application Ser. No. 11/229,065, filed Sep. 15, 2005, which is a non-provisional of U.S. provisional application No. 60/609,970, filed Sep. 15, 2004. The disclosures of all of the foregoing are incorporated herein by reference in their entirety.

STATEMENT REGARDING FEDERALLY SPONSORED RESEARCH OR DEVELOPMENT

This invention was made with government support under Grant No. 5R01HG003583-01 awarded by the NIH; Project No. W911 SR-04-P-0047 awarded by the Department of Defense; Contract No. NBCHC050133 awarded by HSARPA; and Order No. TTA-1-0014 (Agreement No. W81XWH-04-9-0012) awarded by HSARPA. The government has certain rights in the invention.

BACKGROUND

A wide variety of microfluidic devices of disparate, and often incompatible, design have been developed over the past 10-20 years, often with the goal of reducing sample volume requirements in bioanalytical methods. In the absence of standards controlling external dimensional form factors, the nature of the upstream and downstream external interface, and the length, cross-sectional geometry, and diameter of the internal microfluidic pathways, such microfluidic devices often prove incompatible with one another and with existing upstream purification and downstream analytical devices.

Despite advances in microfabrication, making possible analysis at microliter, even nanoliter or picoliter, scale, many biological and environmental samples are first acquired in volumes far greater than, and incompatible with, the scale of existing microfluidic analytical devices.

There is thus a need in the art for modular microfluidic components that can be used as components of integrated fluidic systems, and that can interface microfluidic components having different external dimensional form factors, external interfaces, and/or internal fluidic geometries, into effective fluidic communication, and that can interface preparative modules, or methods, that operate at larger scale with microfluidic preparative and/or analytical components.

SUMMARY

The present invention solves these and other needs in the art.

BRIEF DESCRIPTION OF THE DRAWINGS

The skilled artisan will understand that the drawings, described below, are for illustration purposes only and are not intended to limit the scope of the present disclosure in any way.

FIG. 4 illustrates an embodiment of an off-chip flow-through cartridge.

FIG. 5 illustrates an embodiment of a traveling wave flowthrough bead beater.

FIG. 8 illustrates an embodiment of a nanobioprocessor modular system that can be used for biodefense applications comprising an air sampler, sample concentration module, and a microfluidic sample amplification and analysis module.

FIG. 19A shows the mask design which shows the fluidic layer in blue and the actuation layer in red. FIG. 19B shows the sub-assembly which has two each input and output reservoirs, a reaction chamber and an archive chamber, and a three-way router. The eight pneumatic control lines for the valves terminate in a standard connector to the pneumatics. FIG. 19C shows an etched microfluidic wafer. FIG. 19D shows an assembled MBI-11 three layer microchip with a lab marking pen shown for scale.

DETAILED DESCRIPTION

Figure 1:
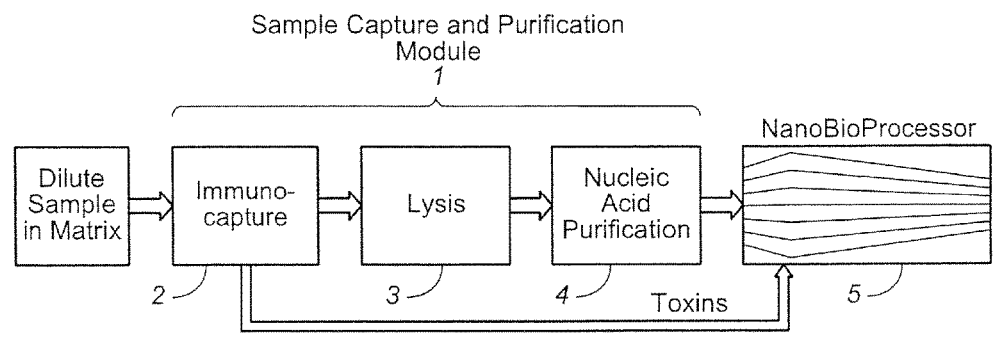
FIG. 1 illustrates an embodiment of a sample capture and purification module (SCPM) and bioprocessor module (BPM) workflow.

It is to be understood that both the foregoing general description, including the drawings, and the following detailed description are exemplary and explanatory only and are not restrictive of this disclosure. In this disclosure, the use of the singular includes the plural unless specifically stated otherwise. Also, the use of "or" means "and/or" unless stated otherwise. Similarly, "comprise," "comprises," "comprising" "include," "includes," and "including" are not intended to be limiting. Terms such as "element" or "component" encompass both elements and components comprising one unit and elements or components that comprise more than one unit unless specifically stated otherwise. The sectional headings used herein are for organizational purposes only and are not to be construed as limiting the subject matter described. All references and portions of references cited, including but not limited to patents, patent applications, articles, books, and treatises are hereby expressly incorporated by reference in their entireties for all purposes. In the event that one or more of the incorporated references contradicts this disclosure, this disclosure controls.

The present disclosure provides integrated modular systems having complementary functionalities for the preparation and analysis of target analytes from various samples. The systems disclosed herein find use in the preparation and analysis of various target analytes, including but not limited to, molecules (e.g. toxins, pharmaceuticals), biomolecules (e.g., nucleic acids, polypeptides, lipids), cells (e.g., eukaryotic and prokaryotic cells (e.g., $Bacillus,$ $Escherichia$)), spores (e.g., $B.$ $anthracia$), viruses (e.g., influenza, smallpox), and other materials, which can be selected at the discretion of the practitioner. In various exemplary embodiments, sample preparation and analysis can be performed by one or more of the system modules, as described below.

In some embodiments, the systems disclosed herein comprise a front-end module for sample capture or purification (SCPM), which in typical embodiments is further capable of introducing the captured and/or purified sample into a bioprocessor module (BPM), which can comprise one or microfluidic devices (e.g., micro-scale, nano-scale, or pico-scale devices), for further preparation and/or analysis. Thus, disclosed herein are modular systems and methods of use for capturing, concentrating, or purifying target analytes from samples and introducing the target analytes thereafter into one or more microfluidic devices. In some embodiments, microfluidic devices can feed to off-chip platforms.

In various exemplary embodiments, the SCPM can capture, purify, or concentrate target analytes by various methods, such as by lysis, emulsification, sonication, centrifugation, chromatography, Solid Phase Extraction (SPE), immunocapture (e.g., immunomagnetic separations (IMS)), bead-based capture, and combinations thereof. In some embodiments, the SCPM can reduce macroscale sample solutions to microscale volumes, for example by concentrating milliliters to microliters or smaller volumes for introduction into one or more microfluidic devices. These SCPM embodiments are capable of acting as modular scale interfaces, permitting microscale and/or nanoscale devices to be integrated into fluidic systems that comprise operational modules that operate at larger scale. These SCPM embodiments usefully permit modules having different dimensional form factors to be integrated into a fluidically communicating system. In some embodiments, the SCPM can purify a sample by removing one or more agents that may be present in crude samples, and that act as inhibitors of downstream processing or analysis. By capturing, purifying, or concentrating target analytes in samples, a SCPM can increase sensitivity of the systems disclosed herein in comparison to conventional methodologies.

A BPM typically comprises one or more microfluidic devices. "Microfluidic device" as used herein refers to a device suitable for manipulating, storing, processing, or analyzing sub-milliliter quantities of fluid, such as microliter (µL), nanoliter (nL), and/or picoliter (pL) volumes. In various exemplary embodiments, a microfluidic device can comprise one or more microchips (e.g., micro-scale, nano-scale, pico-scale devices), capillaries, and combinations thereof. The microchips disclosed herein can be manufactured by microfabrication techniques known in the art and can comprise valves, pumps, chambers, channels, reservoirs etc. and can be suitable for processing or analyzing one or more target analytes. In various exemplary embodiments, a microfluidic device can be a microchip-based cartridge, and can be non-replaceable/reusable or disposable. The microchips disclosed herein can have any shape or dimension. For example, a microchip can be a circular cartridge with one or more radial sample preparation or analysis units and can be used with an instrument that operates the microchip. In some embodiments, a microfluidic device can be automated. For example, microchips can be stored in a "CD changer" and automatically inserted, manipulated to perform one or more functions, and stored as needed by a programmable instrument. Thus, an instrument can provide microchip handling, external pneumatics, temperature control, reagent solutions and the like to operate one or more microchips either simultaneously or sequentially.

In some embodiments, the SCPM is capable of introducing suspensions, colloids (e.g., emulsions), or capture-beads, which can comprise one or more attached target analytes, into a BPM, and in various such embodiments, into one or more microfluidic devices of the BPM. In such embodiments, the one or more microfluidic devices of the BPM is suited for movement of one or more such solids, such as beads, through the device's microfluidic pathways without clogging.

The passage of beads or other solids from SCPM into BPM can serve to effect a downscaling of analyte-containing sample volume, thus interfacing a macroscale module to a microscale device. Such SCPM and BPM embodiments are thus capable of modularly interfacing devices of different scale and/or dimensional form factor, permitting microscale and/or nanoscale devices to be integrated into fluidic systems that comprise operational modules that operate at larger scale.

In various exemplary embodiments suitable for bead-based microfluidic device processing, beads can be reversibly immobilized at various points of the microfluidic passage or circuit by a weir or other physical impediment interposed within the fluidic circuit, by magnetic fields, by affinity capture of the bead, by electrical capture or other mechanisms. In various embodiments, beads can be moved through the fluidic passages or circuit, and can be subjected physical or chemical processing. Analytes that are adherent, or affixed, or adsorbed, or absorbed or otherwise attached to the beads can be subsequently moved into a downstream reaction chamber for further on-chip (that is, within microfluidic device) processing or analysis. In some embodiments, material, such as target analytes, can be eluted off the beads as desired. In some embodiments, series of beads with different affinities can be linked into more complex biomolecular processes with high specificity and sensitivity, e.g., one step can bind cells onto beads, the next can immobilize specific DNA sequences onto beads for cleanup prior to reaction, and a third bead can be used to bind reaction products for purification before introduction into a mass spectrometer and the like. In some embodiments, gels with affinity capture reagents also can be used at various steps selected at the discretion of the skilled artisan.

In some embodiments, a BPM can be used as a stand-alone sample preparation system. Therefore, in various exemplary embodiments, a BPM can connect to various upstream sample collection devices (e.g., an aerosol sampler) or feed downstream analytical platforms or methodologies (e.g., mass spectroscopy (MS), nuclear magnetic resonance (NMR), capillary array electrophoresis (CAE), reverse transcription-PCR (RT-PCR), single molecule detection systems, etc.). However, in some embodiments, one or more analytical methodologies can be performed on a microchip in a channel, reservoir, reaction chamber, etc. or combinations thereof.

The systems disclosed herein have widespread applications in biodefense monitoring, infectious diseases diagnostics, forensics, genomics, proteomics and other fields. For biodefense, the technology provides compact units that may be deployed in the field to serve, for example, as pathogen monitoring devices for buildings, planes, or airports or used in laboratories to cope with surges in testing demand. The systems can prepare and analyze sample from air, biological fluids, agricultural products, or other sources to detect target pathogens. The combination of low consumable costs with automated preparation and analysis have a significant impact on molecular diagnostics. For clinical diagnostics, the technology can be adapted to produce PCR diagnostic instrumentation using disposable devices that are seamlessly integrated to configure additional analyses as desired. The systems disclosed herein also can be applied to pharmacogenetics, human medical genetics, biomedical research, animal and plant typing, and human identification.

Additional applications of the disclosed systems include molecular diagnostics, such as detecting microorganisms, genotyping organisms, sequencing, and forensics; creating sample preparation and analysis platforms for various methodologies, such as RT-PCR, resequencing, and protein analysis; creating sample preparation stations for most analytical platforms, such as mass spectrometry, capillary array electrophoresis, differential display, and single molecule detection; and for biodefense applications.

The systems disclosed herein can be automated in whole or in part, for example by the use of robotics, and can be scaleable from hand-held devices to field monitors to laboratory instrumentation.

1. Concentration of Target Analytes

Figure 2:
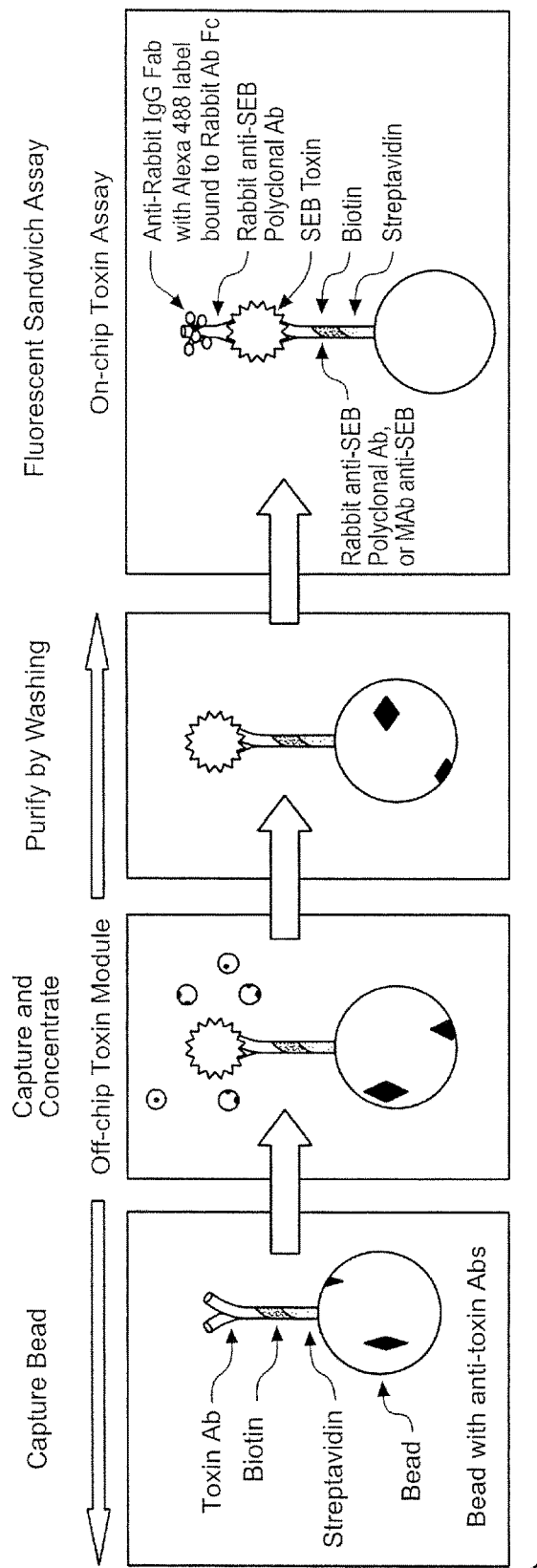
FIG. 2 illustrates an embodiment of a toxin assay workflow.

In some embodiments, target analytes in a sample can be concentrated prior to introduction into a microfluidic device for further processing or analysis. In some embodiments, one or more target analytes can be concentrated using one or more off-chip flowthrough devices that can hold macroscale volumes (e.g., milliliter to liter volumes) and concentrate one or more target analytes onto a small surface (e.g., a microbead). In some embodiments, one or more target analytes can be concentrated using an on-chip flowthrough device that can be fed by an off-chip reservoir holding macroscale volumes. In some embodiments, on- and off-chip devices can be used in combination. In some embodiments, captured target analytes can be selectively eluted into a volume suitable for downstream processing or analysis. As shown in FIG. 1, an SCPM 1 can comprise modules for immunocapture 2, lysis 3, nucleic acid purification 4, and can be integrated with a nanobioprocessor 5. In some embodiments, a molecule, such as a toxin can be immunocaptured and fed directly to a nanobioprocessor 5 (FIG. 2).

Materials suitable for capturing target analytes onto a surface include various types of extraction matrix materials that can be comprised of beads, monoliths, modified polymers, and the like. In some embodiments, extraction matrix materials can comprise various attached functional groups (e.g., $C_4$, $C_{18}$, carboxy, and amino groups), mixed beds of various beads or chemistries, or affinity capture moieties (e.g., antibodies, lectins, haptens, ligands (e.g., biotin), receptors, nucleic acids, etc.). In some embodiments, nucleic acids can be captured using carboxylated beads, such as SPRI or unmodified silica beads, and eluted into a suitable volume of a polar solvent, such as water. In some embodiments, a nanoscale capture method can be used that employs silica capillaries in which chaotrops, such as thiocyanate, force nucleic acids onto the capillary surfaces and after washing, concentrated and purified nucleic acids can be eluted into a buffer for further processing or analysis (see U.S. Pat. No. 6,489,112). Other methods of solid phase capture of various target analytes are described, for example, in Weimer et al. 2001 *Appl. Environ. Microbiology*, 67:1300-1307.

a) Off-Chip Flowthrough Device

Figure 3:
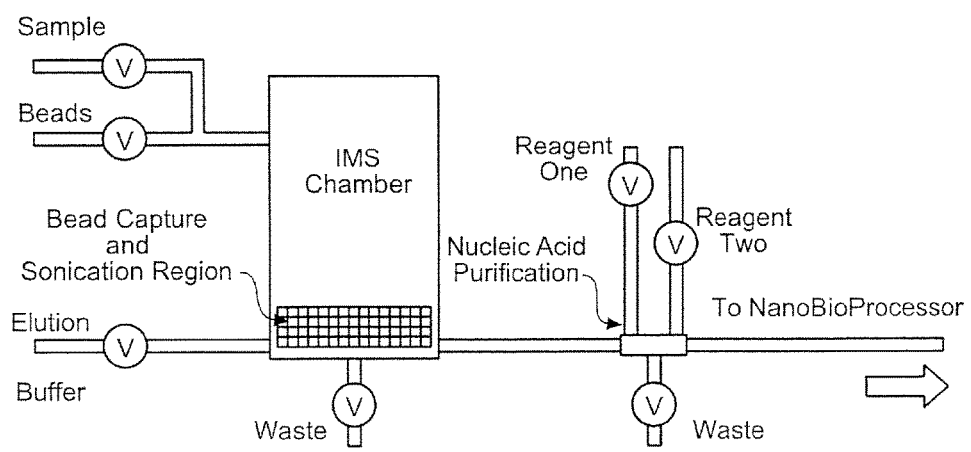
FIG. 3 illustrates an embodiment of a sample capture and purification module (SCPM) integrated with a bioprocessor module (BPM).

In some embodiments, target analytes can be concentrated using an off-chip flowthrough device 130 that channels macroscale sample volumes through a concentration matrix 140 (FIG. 4). In some embodiments, the concentration matrix retains the target analytes while the bulk solution and interfering compounds pass through the device. In some embodiments, interfering or unwanted compounds are retained on the matrix 140 and the target analytes pass through the device. Depending on the sample form (surface, water, soil, aerosol, biomaterials) coarse filtration (ca. 20 μm) may serve to remove bulk contaminants and particulates. In some embodiments, an off-chip flowthrough device can include a flitted opening 150 in the bottom with matrix loaded therein and can include a bore (≤1 mm) port for elution (FIG. 4). The concentration matrix can use non-affinity media or affinity capture media, as described herein. An example of an off-chip flowthrough device integrated with a BPM microfluidic device is illustrated in FIG. 3.

i) Non-Affinity Capture

"Non-affinity capture" as used herein refers to the non-specific capture of a target analyte on a medium by hydrophobic, hydrophilic, or ionic interactions.

In some embodiments, non-affinity capture of target analytes can employ the Extract-Clean™ Solid Phase Extraction (SPE) Kit (Alltech) which includes 1.5 mL (or 4 mL) columns pre-packed with an assortment of SPE media with 20 μm polyethylene frits. The media can either capture the target analytes for future elution or can allow the target analytes to pass through while undesired material is retained on the media. For example, cells, virus, or proteins in cell lysates at ranges from about 1 to $10^4$ CFU/mL, about $10^2$ to $10^3$ PFU/mL, and 0.1 to $10^2$ ng/mL, respectively can be applied to the media. The sample can be loaded manually or via robotics and flowthrough the media with vacuum applied as needed. In some embodiments, the target analytes are bound to the packing material which can be washed and the target analytes can be concentrated by elution from the media. In various exemplary embodiments, a 3 mL syringe barrel SPEC (ANSYS Technologies) with a silica microfiber disk to prevent channeling for flow properties and retention characteristics or Big Beads can be used. Standard or specialty chromatography media can also be used to provide concentration or purification of the desired material. For any selected media, the bed volume, different media formulations, wash, and elution conditions can be optimized for maximum retention to enhance sensitivity by persons of ordinary skill in the art.

Various methodologies can be used to monitor sample flowthrough the device, such as immunotagging and fluorescent detection using, for example, an Avalanche fluorescent scanner (GE), capillary electrophoresis using, for example, the MegaBACE 1000 (GE), by growth assays for cells, or other methods well known to one skilled in the art.

ii) Affinity Capture

"Affinity-capture" as used herein refers to the capture of target analytes using a medium comprising a molecule (e.g., antibody, ligand, receptor, lectin, hapten, epitope, oligonucleotide etc.) that is substantially specific for a target analyte. In some embodiments, magnetic beads modified with a monoclonal antibody to a surface epitope of target analyte (e.g., a cell, organism, spore, or toxin) can be added to a sample. In some embodiments, mixtures or sets of beads coated with antibodies to specific organisms, cell types, subtypes, species, nucleic acids, proteins, etc. can be applied to a sample sequentially or in various combinations, selected at the discretion of the practitioner. The antibody-coated beads bind to the target analytes thereby capturing them from solution. The beads can be collected by a magnet and undesired contaminants and potential inhibitors can be removed by washing.

In various exemplary embodiments, the collected, washed beads can be resuspended for further processing either in a flowthrough device or another device or moved onto a microchip of a BPM. As described herein, for embodiments relating to biodefense applications, the collected and washed beads can be resuspended in 10 μL of buffer and a small sonication horn inserted. In some embodiments, flowthrough sonication using a device as described in FIG. 6 can be used. After sonication, the sonicated material can be passed through a filter and onto a BPM microfluidic device.

b) On-Chip Flowthrough Device

In some embodiments, a BMP microfluidic device can be used to concentrate a target analyte. In some embodiments, target analyte concentration on-chip can facilitate module integration, the use of microfabrication technology, and the ability to perform various methodologies, such as PCR, in the same chamber. In some embodiments, this may necessitate the use of relatively large diameter channels to yield appropriate flow rates. In some embodiments, immunoaffinity capture provides a rapid and specific method for concentrating and purifying pathogenic organisms or viruses, proteins, or other target analytes from sample. For example, to concentrate target analytes, a bead-based sample preparation can be adapted from batch process to an on-chip process. For example, antibody-coated beads can be placed into an integrated, microfabricated capture chamber using electrokinetic bead bed packing and weir bead trapping methodologies (Oleschuk et al. 2000. *Analytical Chemistry* 72:585-5909).

In some embodiments, carboxylated beads in packed beds in a flowthrough mode can be used in microfabricated glass devices to post-process polynucleotides, such as DNA sequencing mixtures. Glass chips with dams for trapping beads can be microfabricated from Borofloat glass. The dam gap between the top of the dam and the opposite channel can be designed for carboxylated beads or other types of beads such as silica beads, beads with affinity capture using antibodies, lectins, or nucleic acids, etc. The deep channels can be first etched with HF and then a second shallow etching can define the dam height to 0.5 µm or more depending upon the specific bead and application. In some embodiments, beads can be packed by pressure and removed by vacuum aspiration. In some embodiments, immuno-functionalized or other magnetic beads may be introduced into a chamber without a weir. Upon application of a small magnetic field perpendicular to the plane of the chamber, the beads self-assemble into a quasi-regular series of vertical posts with ~5-mm spacing (Doyle et al. 2002. *Science* 295:2237).

In various exemplary embodiments, matrices such as chromatography media, gels with attached antibodies or other affinity capture material, gels with or without chemical modifications, solid phase extraction media, monoliths, or other separation or binding matrices well known to one skilled in the art can be used.

2. Lysis Module

In some embodiments, target analytes can be disrupted and lysed on-chip or off-chip. Non-limiting examples of target analytes that can be disrupted or lysed are (e.g., prokaryotic, eukaryotic, archaea), spores (e.g., bacterial (e.g., *B. anthracia, Clostridium*) or fungal (e.g., *C. immitis*)), organelles (e.g., mitochondria, nuclei, etc.), nucleic acids, chromosomes, plasmids, ribosomes, proteosomes, viruses (such as smallpox, influenza, West Nile, polio, hepatitis, and retroviruses). In some embodiments, target analytes can be disrupted or lysed by sonication. In some embodiments, target analytes captured onto beads can be sonicated before introduction onto a microchip.

Figure 6:
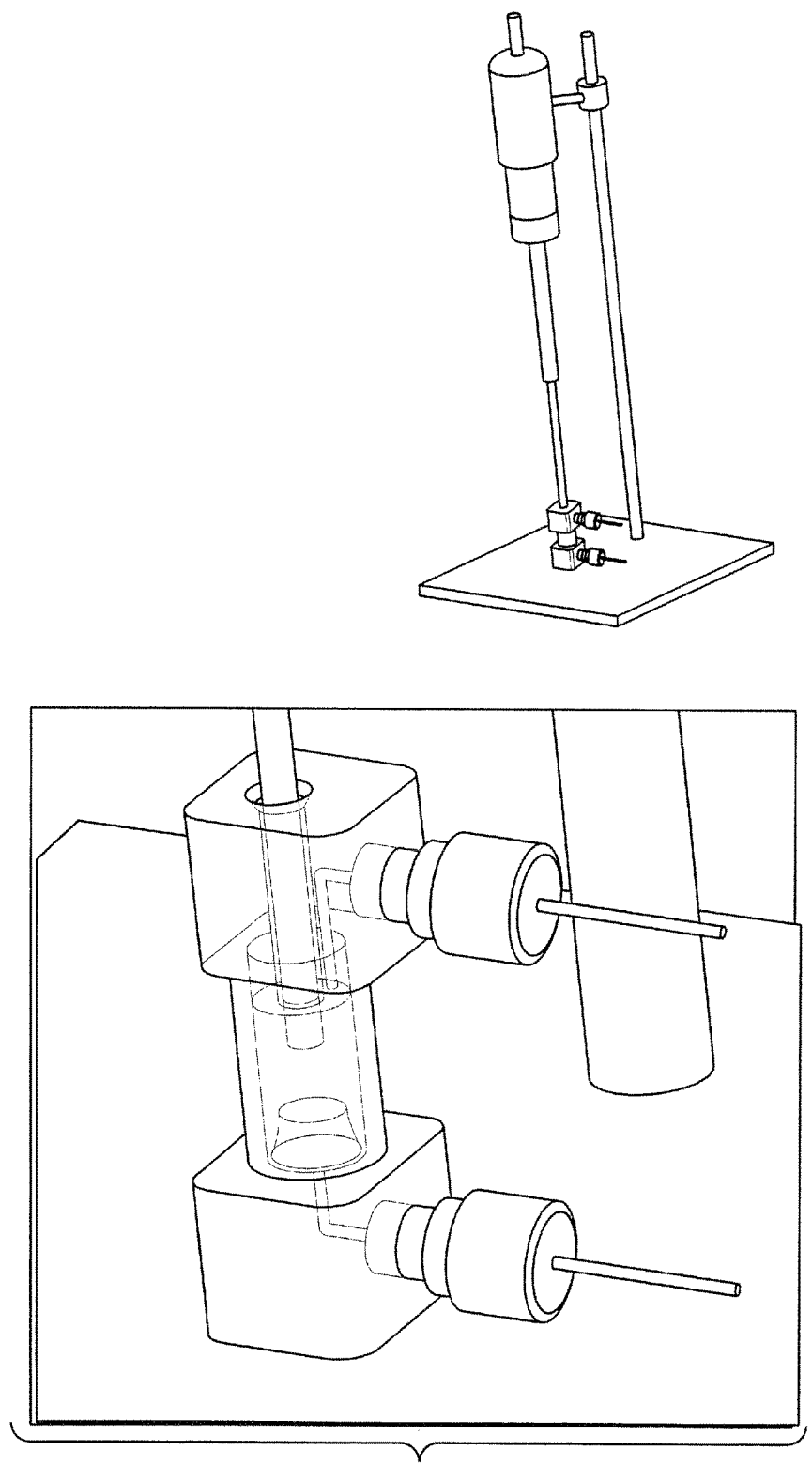
FIG. 6 illustrates an embodiment of flowthrough sonication in which a probe is inserted directly into a collector effluent.

Ultrasonic disruption can be performed using a horn that is immersed into a solution comprising a crude target analyte solution or target analytes that have been captured onto beads, concentrated, and purified. A sonicator also can be a flowthrough sonication device having a probe that can be inserted directly into a collector effluent (FIG. 6). The chamber also can be designed to contain or trap aerosols and can be automated as described herein.

In some embodiments, disruption or lysis can be achieved by bead beating. The beads can be the same or different from capture beads, described herein. In some embodiments, differential properties of the beads used for lysis and/or capture such as magnetic versus non-magnetic, different densities, etc. may be used to separate the various types of beads to simplify downstream processing or analysis. In some embodiments, flowthrough, traveling-wave, bead-beating device 10 can be used (FIG. 5). For example, as shown in FIG. 5, rotating magnetic pole piece 20 creates a magnetic wave down flowthrough tube 30 as the pole piece is rotated. The rotation can be up to about 100 Hz and can produce sufficient acceleration of beads through the adjacent tube to break spores and other types of target analytes flowing-through the tube. Beads in some embodiments have a plurality of shapes to facilitate lysis.

To assess disruption or lysis, the loss of viability vs. time can be used to determine desired power settings, exposure times, volumes, and geometries; setting such parameters is within the abilities of the skilled artisan. In some embodiments, selected samples can be used to test release of DNA or RNA in TaqMan assays. Disruption can be optimized for spores and for shearing macromolecules to lower their viscosity and cross-sectional area without rendering them unsuitable for downstream processing or analysis. In some embodiments, lysates can be passed through filters having a pore size of at least about 10 µm, even at least about 20 µm, 30 µm, or even higher, to remove clumps that could clog the microchannels of a microfluidic device.

In some embodiments, the disrupted or lysed material can be used as a feedstock for further purification, either on-chip or off-chip. For example, for assaying a nucleic acid, a purification step of nucleic acid hybridization onto a bead with selective oligonucleotides can purify the target sequence from the background. For a protein, capture onto a solid surface such as hydrophobic, carboxylated, or other chemistry can provide non-specific purification of a class of proteins, while affinity capture can provide enhanced specificity when needed. Similarly, multiple steps of purification can be performed, with a mix and match of on-chip and off-chip, and bead based and other matrices as required.

In some embodiments, lysis can be performed after introduction into a microchip. In such embodiments, the microchip receives the samples with cells to be lysed.

3. Nucleic Acid Purification Module

In some embodiments, a system of the present invention can include a Nucleic Acid Purification Module (NAPM). The NAPM can be designed to accept a solution or samples in other physical forms, such as one or more beads, colloids, multiple-phase (nonhomogeneous or heterogeneous) solutions, or other compositions. In some embodiments, the NAP can be designed to receive input from a lysis module. The volumes received by the NAPM can range from milliliters to sub-picoliter volumes. In some embodiments, the NAP output can be delivered to a BPM microchip or other microfluidic device for further processing or analysis.

Figure 7:
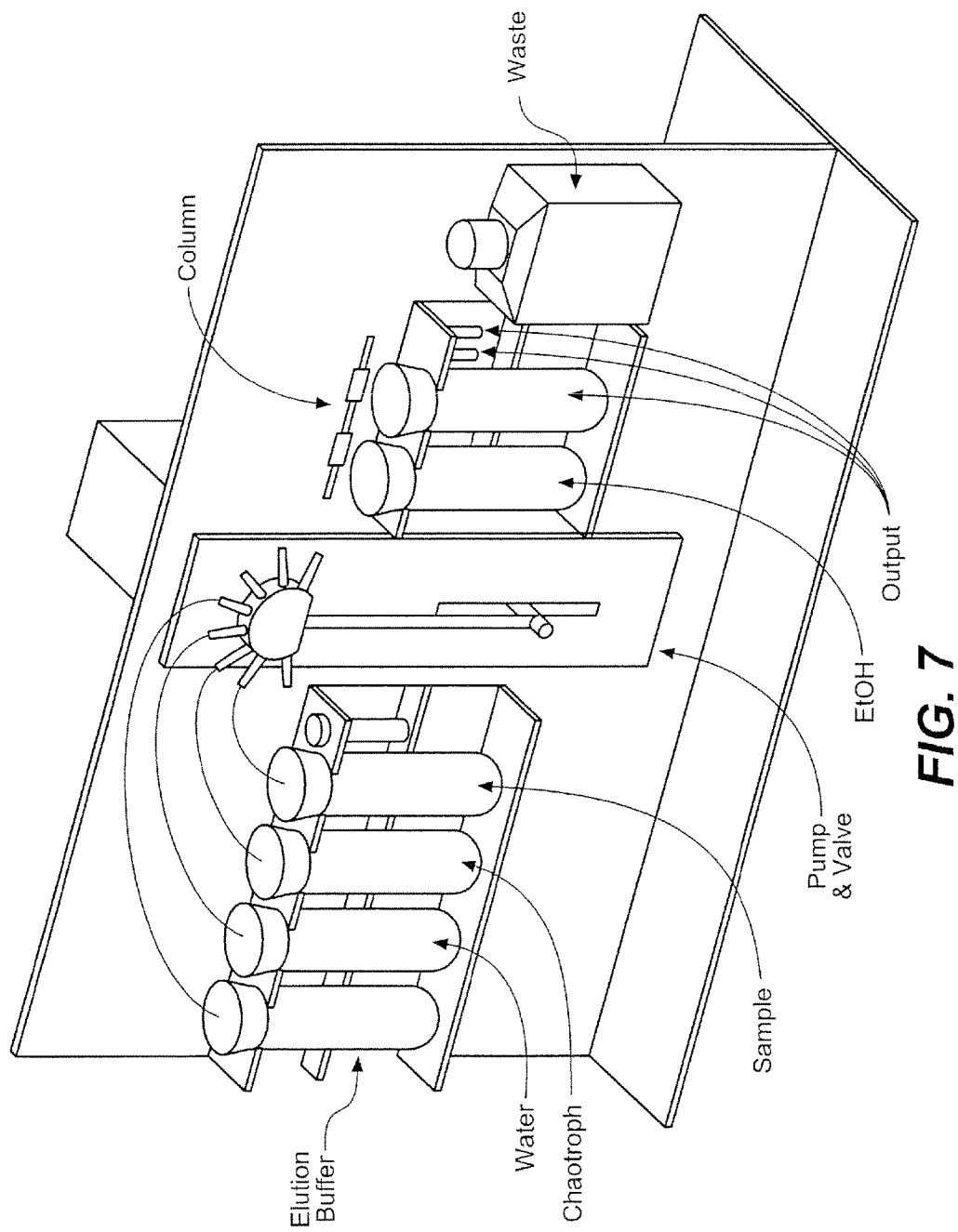
FIG. 7 illustrates an embodiment of a nucleic acid purification module.

Various chemistries can be adapted for use by a NAPM. In various exemplary embodiments, a NAPM can be designed to perform total nucleic acid purification by various methods, such as purification by surface adsorption/desorption using chaotrophs; selective nucleic acid purification by, for example, electrophoretic capture on oligonucleotide-containing gels; or selective nucleic acid purification by hybridization onto oligonucleotide-containing beads. An example of a NAPM is illustrated in FIG. 7.

a) Total Nucleic Acid Purification

Total nucleic acids in a sample can be purified using a non-specific capture method that employs chaotropes (chaotrophs) to force nucleic acids from solution onto surfaces. For example, U.S. Pat. No. 6,489,112 describes a quantitative nanoscale "template capture" method using chaotrophs such as thiocyanate or guanidinium to force nucleic acids onto the surface of silica capillaries. After washing, concentrated and purified nucleic acids can be eluted into buffer for nanoscale sample processing or analysis, such as cycle sequencing. This method also can be used to purify nucleic acids from lysates.

In some embodiments, the input sample can be mixed with a chaotroph in the presence of glass beads, or other appropriate surfaces, such as the walls of a channel. The chaotroph forces the nucleic acids out of solution, causing them to adsorb to the glass beads or other surfaces. The chaotroph also inactivates nucleases which can be present in a sample which substantially inhibits nucleic acid degradation. After an incubation period, cell debris, denatured proteins, and other components soluble in the chaotrophs can be removed by aspiration using, for example, a vacuum and discarded into a waste stream. The purified sample can be further washed to remove additional contaminants and the nucleic acids can be eluted into a buffer for recovery and introduction into a microchip or other fluidic system.

In some embodiments, conditions for nucleic acid purification include 5 M sodium thiocyanate, 95° C. for 90 sec to denature, 30° C. for 5 min to bind to a surface (e.g., glass beads) and an 80% EtOH for 2 sec. In some embodiments, nucleic acids can be purified onto modified beads, such as SPRI carboxylated beads, using several different chaotrophs and elution recovery chemistries.

b) Selective Nucleic Acid Purification

In some embodiments, target nucleic acids can be selectively purified using off-chip hybridization to oligonucleotide capture sequences.

In some embodiments, samples can be moved by electrophoresis, hydrodynamic pressure, centrifugation, or other forces onto fixed or moveable matrices, comprised of unmodified beads, modified beads, replaceable affinity capture gels, monoliths, colloids, two phase solutions, and other materials. In various exemplary embodiments, a matrix may be unmodified and bind a target nucleic acid based upon the surface properties of the material, a matrix can be modified to enhance or retard the binding of components of the sample, or a matrix can have attached oligonucleotide sequences complementary to target sequences, bound antibodies, or other affinity capture materials. In some embodiments, a biotin label on an oligonucleotide can be hybridized with the target DNA. A streptavidin moiety on a bead can be bound to the biotin to purify the desired target nucleic acid.

For example, a sample comprising a target nucleic acid may be applied to beads containing bound oligonucleotide sequences complementary to the target nucleic acid. The bound target nucleic acid can be washed in low ionic strength buffer to remove salts, contaminants, and mispaired fragments, and eluted by heat and voltage in nanoliter volumes. In some embodiments, affinity capture can be rapid ($\leq 7$ min) with a high efficiency ($\geq 90\%$ for cycle sequencing products). This approach can be scalable to off-chip configurations. Output volumes can be varied from about 10 nL to about 1 mL depending on the physical configuration.

In some embodiments, the above-described compositions and methods can also be used to remove nucleic acids from samples, which can be assayed for protein, lipid, carbohydrate or non-cognate nucleic acids.

4. Introduction of Beads or Solutions into Microchips

Samples can be introduced into various microfluidic devices or other fluidic system directly or after processing, for example, by capture and nucleic acid purification as described herein. In some embodiments, beads from an affinity capture step can be introduced into a microchip in a small volume, such as microliter or nanoliter volumes. The beads can be pumped into a reservoir on the microchip, such as with a syringe pump or pipetting device, and on-microchip pumps can be used to move the beads into a portion of the microchip where the beads can be trapped or retained.

In some embodiments, single beads can be moved on the microchip for processing or analysis, such as DNA sequencing, single molecule analysis, MS analysis of proteins, including matrix-assisted laser desorption/ionization (MALDI) scanning and peptide fingerprinting. The single beads may be routed on-microchip to individual chambers by, for example, the application of flow cytometric techniques. Alternatively, a single bead can be placed into a chamber by stochastic distributive processes in which, on average, only a single bead is predicted to arrive in a chamber.

In some embodiments, samples can be further processed in various types of fluidic systems, such as a batch mode, or a flowthrough system, or a combination thereof. The system can be based on microchips, capillary(s), tubing, wells, or other vessels and microfluidic devices. The introduced samples can be processed biochemically or chemically to separate components, tag components, or analyzed on-microchip, or prepared for downstream analysis.

5. BPM

A BPM typically comprises one or more microfluidic devices that optionally can be operated by instrumentation and programmable software as described below. In some embodiments, a microfluidic device can be a microchip, nanochip, or picochip held in a cartridge that inputs samples from the SCPM, routes liquids between fluidic circuits and reaction chambers, adds reagents, and performs assays for various target analytes, such nucleic acids and toxins. In some embodiments, the various types of chips can process samples in individual bioprocessor modules using MOV valves, pumps, and routers as system control elements to thereby control reaction times and sequences. In some embodiments, the chips disclosed herein can be integrated with an SCPM.

a) Micro-robotic on-chip Valve and Pump (MOV™) Technology

MOV micro-valves, micro-pumps, and micro-routers combine two glass microfluidic layers with a deformable membrane layer, such as polydimethyl siloxane (PDMS), that opens and closes the valve, and a pneumatic layer to deform the membrane and actuate the valve. The fluidic channel etched in the top glass layer (FIG. 9) is discontinuous and leads to vias that act as valve seats. PDMS membrane 40 sits against the valve seat and normally closes the fluidic path between the two vias. On the opposite side of PDMS membrane 40, a pneumatic displacement chamber, formed by etching, is connected to a full-scale vacuum or pressure source. By controlling a miniaturized off-chip solenoid, vacuum or pressure (approximately one-half atmosphere) can be applied to PDMS membrane 40 to open 50 or close 60 the valve by simple deformation of the flexible membrane.

Figure 10:
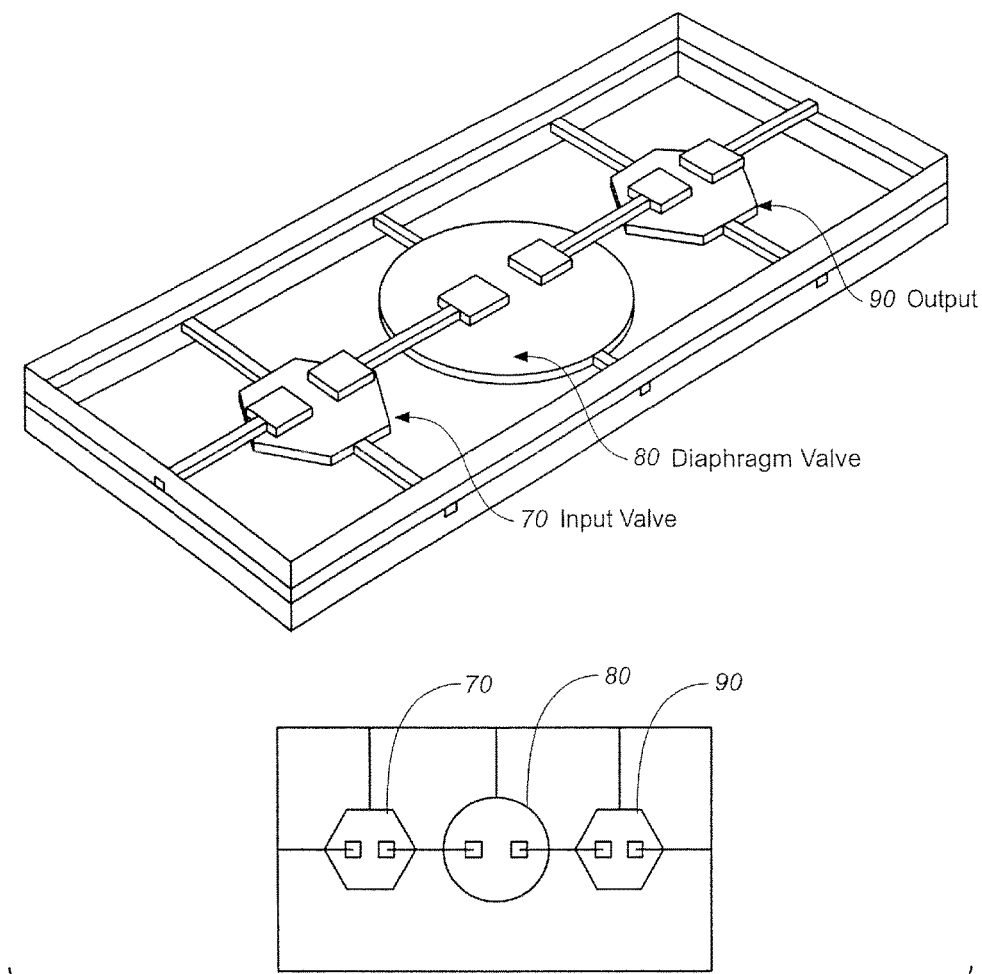
FIG. 10 illustrates an embodiment of a microfabricated pump.
Figure 11:
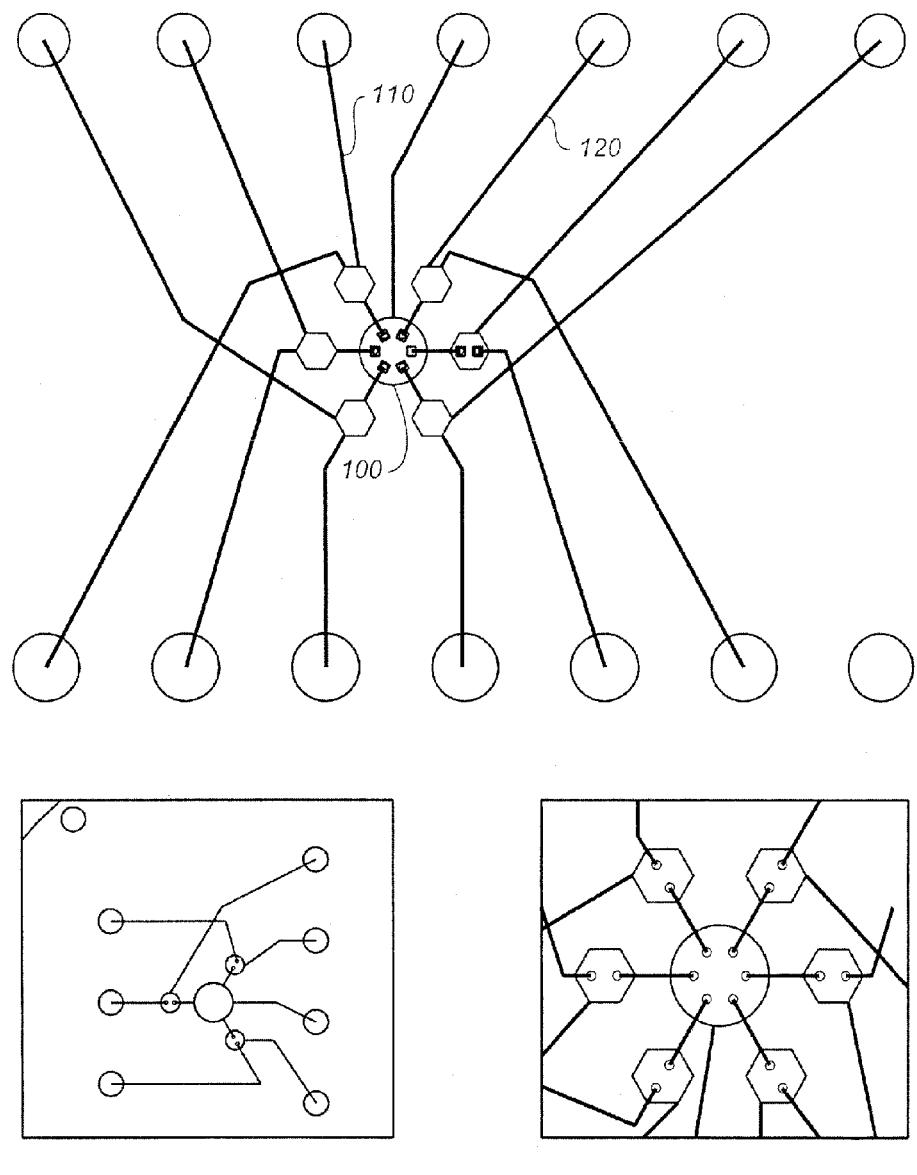
FIG. 11 illustrates an embodiment of a microfabricated router.

Self-priming MOV pumps (FIG. 10) can be made by coordinating the operation of three valves 70, 80, 90, and can create flow in either direction. A variety of flow rates can be achieved by the timing of the actuation sequence, diaphragm size, altering channel widths, and other on-chip dimensions. Routers (FIG. 11) can similarly be formed from these valves and pumps. The routers can be formed using three or more valves each on a separate channel 110, 120 connecting to central diaphragm valve 100. By actuating the proper combinations of valves, liquids from one of the channels can be drawn into the central diaphragm valve and expelled into a different channel to rout the liquid. Bus structures can also be created.

The MOV valves and pumps can be created at the same time in one manufacturing process using a single sheet of PDMS membrane, i.e., it costs the same to make 5 MOV pumps on a chip as it does to create 500. Thus, the disclosure herein provides methods to create complex micro-, nano-, and pico-fluidic circuits on chips, and allows the porting of virtually any reaction or assay onto a chip. In general, this technology can be at least substantially insensitive to variations in solution ionic strength and surface contamination, and does not require applied electric fields.

b) Microfluidic Devices

Figure 31:
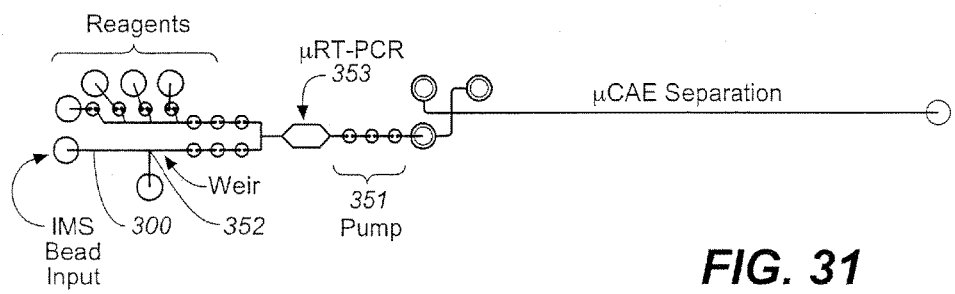
FIG. 31 illustrates an embodiment of a mask design for bioprocessor module that can be used for nucleic acid analysis (RT-PCR and µCAE).

FIG. 31 shows an example of single bioprocessor module that can be used for nucleic acid analysis. In this design, captured beads with bound purified nucleic acids from IMS and nucleic acid purification can be input into the lower channel 350. The on-chip MOV pumps 351 move the beads to a weir 352 where the nucleic acids can be released by the local application of heat and pumped into the µRT-PCR chamber 353 as Real-Time PCR reagents and internal standards can be added from the reagent inputs. The valves surrounding the chamber close for thermal cycling.

Figure 32:
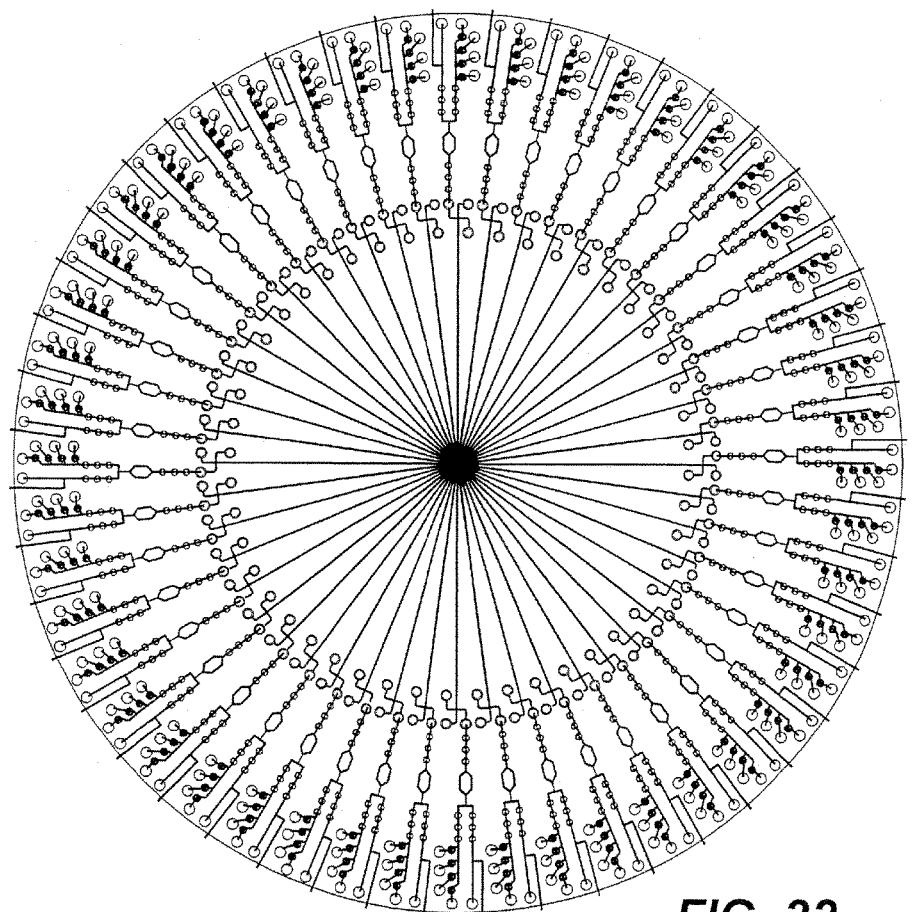
FIG. 32 illustrates an embodiment of a wafer scale design for a bioprocessor microchip with 48 units on a 6" wafer, each with RT-PCR and µCAE capabilities.

FIG. 32 shows an example of a 48-unit design for a 6" microchip using the design from FIG. 31. In some embodiments, 96 or more units can be placed radially on a 6" chip. In some embodiments, 384 separation channels can be placed on an 8" chips. A 96-channel microchip can operate for about 30 days if the channels are reused only about 3 times. In some embodiments, 240 units can be placed radially on a 12" microchip depending on the requirements of the final specifications, the number of target analytes tested, and the degree of multiplexing.

In some embodiments, the various chips can comprise drilled via holes that form valve chambers as reaction chambers (FIG. 29) that can be used, for example, in RT-PCR. By using a 3 mm thick drilled wafer and a 300 µm dia drill, a 212 nL chamber with a 3 mm detection pathlength down the long axis (rather than transverse to the channel) can be produced. In some embodiments, these chamber can have an excellent surface-to-volume ratio. In some embodiments, larger volumes can have better surface-to-volume ratios and longer pathlengths. In general, detection on a chip can be done transverse to the channel and has a pathlength equal to the channel depth, about 30 µm; similarly, in capillary systems, pathlengths are about 50 to 200 µm. The excellent volume-to-surface ratio and approximately 100-fold longer pathlength benefit both the sample preparation biochemistry (by the higher volume-to-surface ratio) and the fluorescence detection respectively with this single design. The same detection design can be used to detect toxins.

Figure 33:
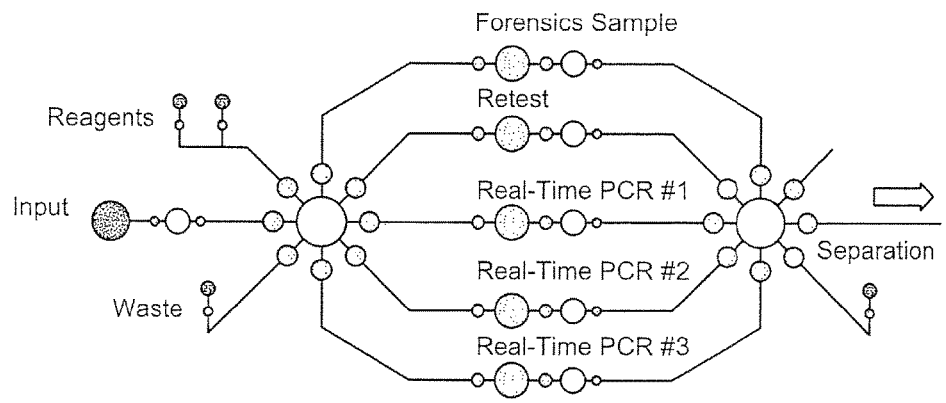
FIG. 33 illustrates an embodiment of a multiplexed bioprocessor circuit. MOV routers split samples to three multiplexed RT-PCR reactions, create forensics and retest samples, and can select samples for µCAE confirmation.

In some embodiments, the various chips can split input samples into the appropriate number of reactions (dependent upon the degree of multiplexing achieved) using the MOV routers and adding reagents, such as PCR master mix containing internal standards. As shown in FIG. 33, samples for forensic archiving and retesting can be aliquoted using an input MOV router and then samples from any positive Real-Time PCR reactions can be selected for µCAE. FIG. 33 illustrates that in some embodiments a µCAE channel is not needed for each bioprocessor unit or reaction. In some embodiments, two to four µCAE channels on a complete 6" microchip can be used since they can be used for confirmation and can be deeply nested to connect to tens of Real-Time PCR chambers and other types of assay chambers (e.g., toxin assay chambers).

Figure 17:
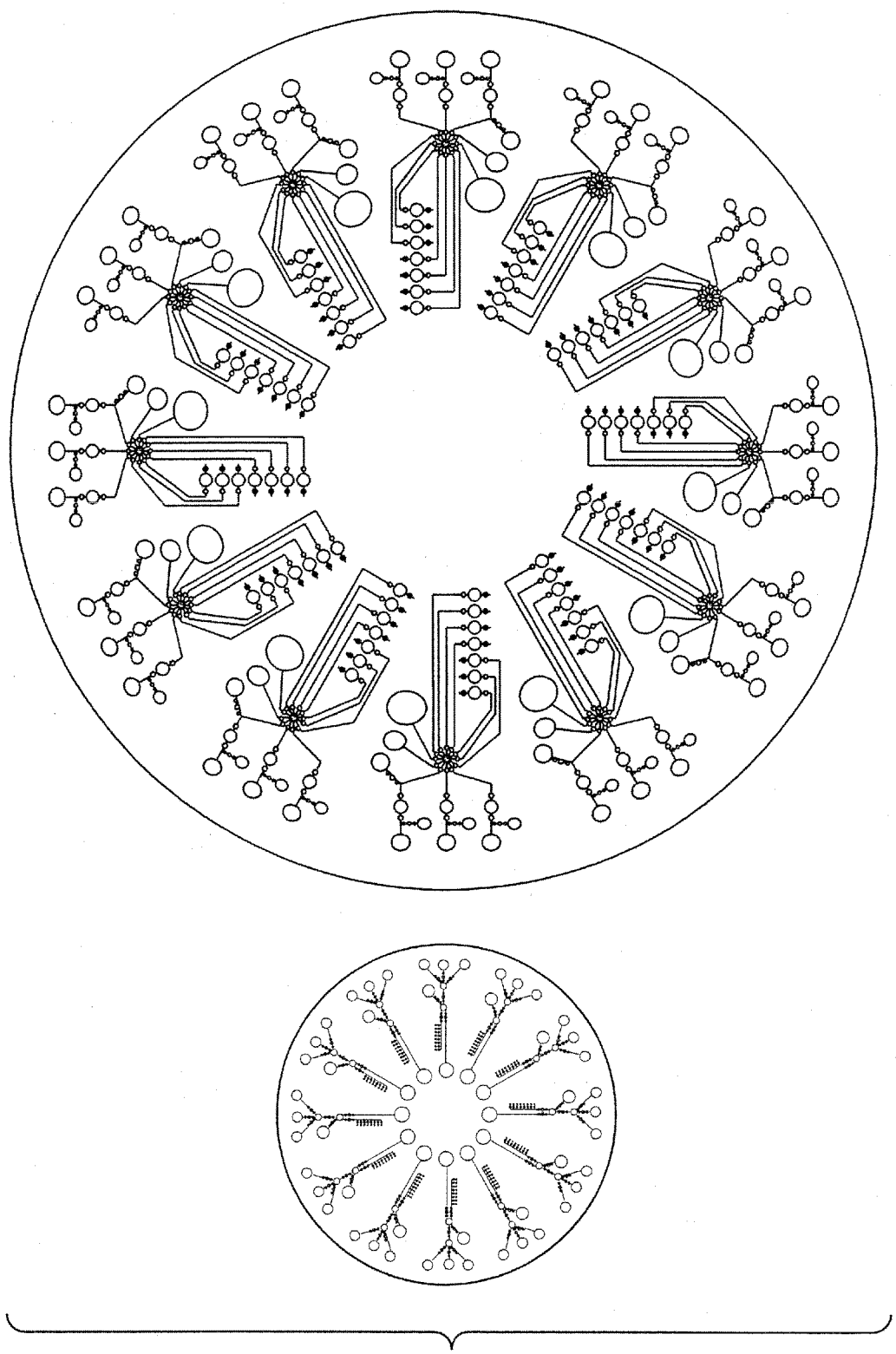
FIG. 17 illustrates an embodiment of a 12 unit bioprocessor cartridge.
Figure 25:
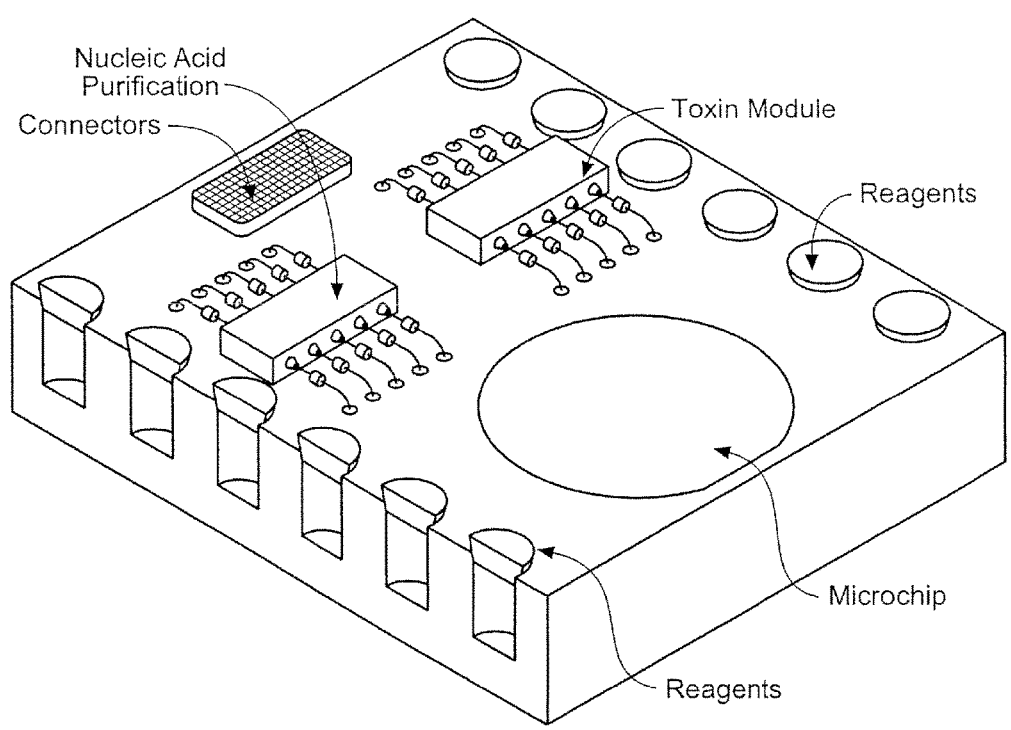
FIG. 25 illustrates an embodiment of a microchip that is designed as a disposable cartridge which includes on-board reagents, the nucleic acid purification, and the toxin module.

FIG. 25 illustrates an example of a microchip for biodefense applications that is designed as a disposable cartridge and a platform that operates the microchip for sample preparation of pathogens. The chip comprises MOV valves, pumps, and reaction chambers, sample ports for the injection of reagents, and inlet and outlet ports for interfacing with upstream concentration and downstream analysis modules. FIG. 17 illustrates a microchip using a circular substrate with 12 units of bioprocessors laid out radially. In some embodiments, one unit at a time can be used, and the microchip rotated between uses. Alternatively, embodiments with different geometries of substrates and different fluidic layouts can be used.

The bioprocessor module containing the fluidics, in this example on a microchip, can receive samples from the upstream SCPM, create aliquots for archiving and retesting, lyse samples on-chip, prepare and label samples, and output them to a detector for analysis. In this example, BPM comprises microchip cartridges that contain the fluidics and an instrument that operates the cartridges. The cartridges can be in a "CD" format and have 12 bioprocessor units per cartridge in sectors with each unit used for single samples or for multiple samples (FIG. 17). For example, the cartridge can process one sample and then be rotated to receive the next sample. The cartridges can be adapted to different sampling regimes and changed as needed. In some embodiments, sets of cartridges can be stored in mini-carousels, analogous to a CD changer. The instrument can provide the mechanics to store, load reagents, run, and change cartridges and control the processes.

In some embodiments, a nano-bioprocessor cartridge designed to process samples using nanofluidics with on-cartridge MOV valves and pumps as control elements can be used. The MOV valves are normally closed, rugged, easily fabricated, can be operated in dense arrays, and have low dead volume. The valves can be made following the design of Grover et al. (2003), *Sensors and Actuators* B89:315-323, by combining glass layers with a polydimethyl silane (PDMS) layer as a deformable membrane.

Figure 9:
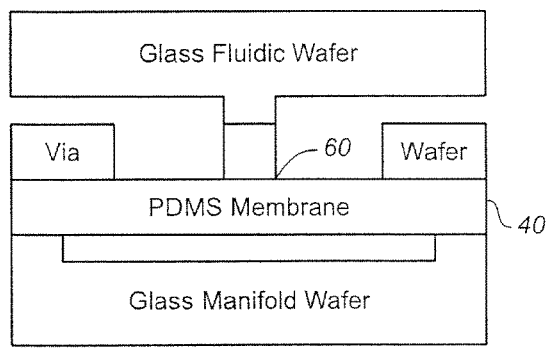
FIG. 9 illustrates an embodiment of a MOV™ valve.
Figure 9:
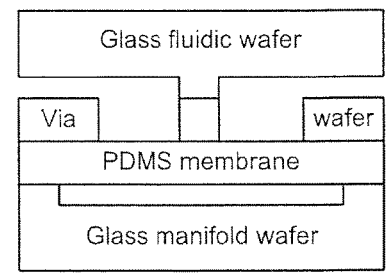
Figure 9:
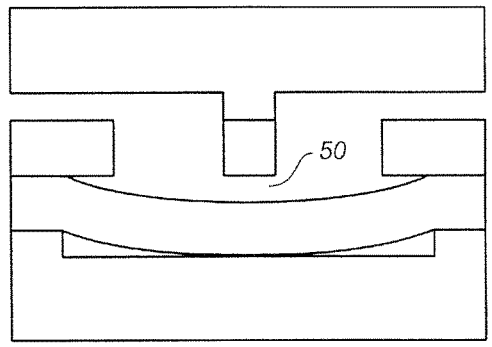
Figure 9:
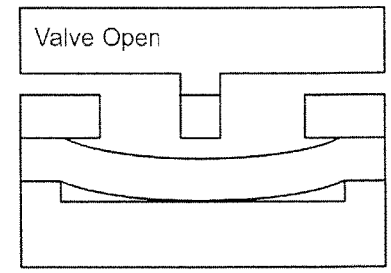
Figure 9:
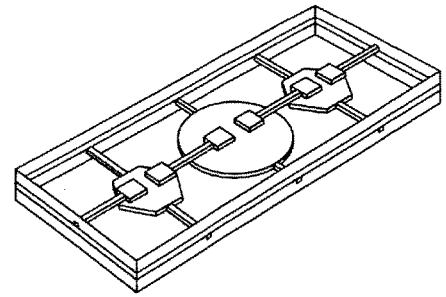
Figure 9:
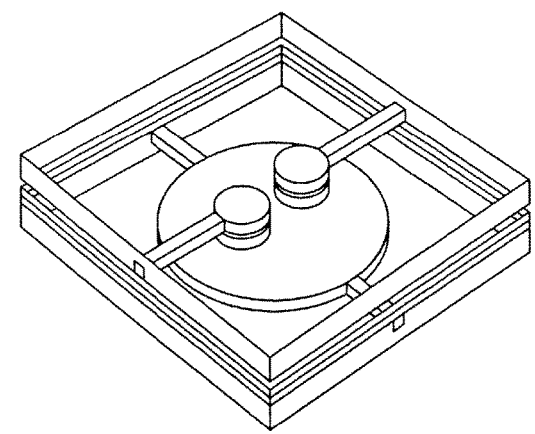

In some embodiments, self-priming pumps (FIG. 10) can be made by combining three of the valves shown in FIG. 9. The central diaphragm valve can be larger than the flanking valves which function to control the direction of flow. In addition, the central valve can function as a reaction chamber or mixer: the PDMS can be deformed up to 2 mm, creating reaction chambers that can contain as much as hundreds of microliters or as few as tens of nanoliters (Grover et al. 2003. Sensors and Actuators B89:315-323). These chambers can expand and contract dynamically.

In the present disclosure, the MOV valves and pumps can be combined into processors to prepare and process micro- and nano-scale samples.

Figure 29:
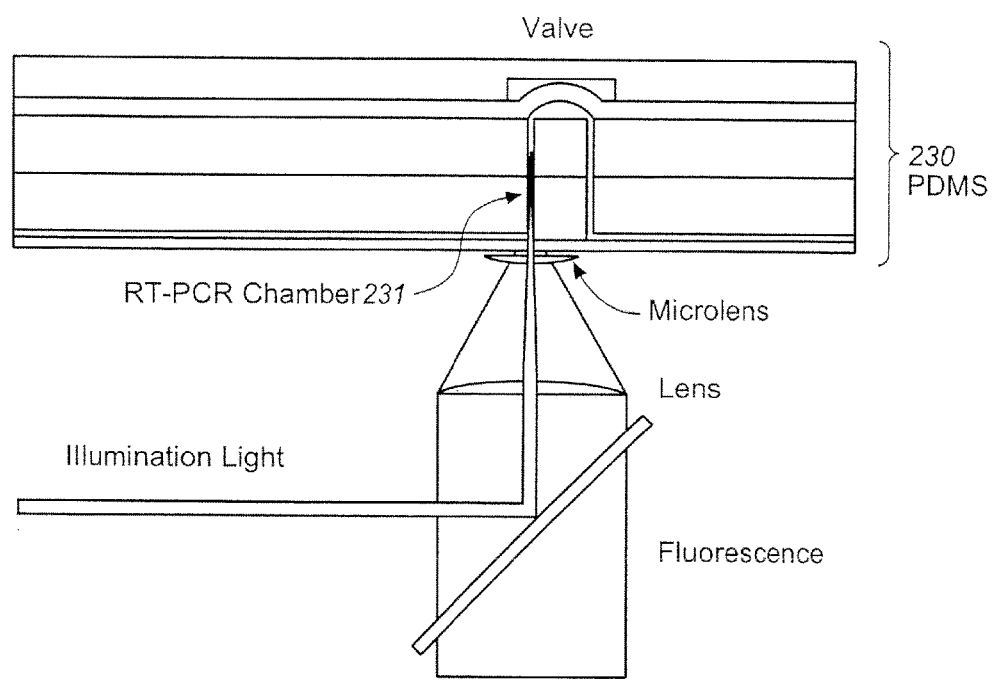
FIG. 29 illustrates an embodiment of a RT-PCR chamber with increased pathlength.

In the present disclosure, the size of the via hole can be varied to create a reaction chamber in the via hole. By combining variations in the width of the via hole and the thickness of the wafer(s) through which the via hole passes, a wide range of chambers can be fashioned. In addition to functioning as reaction chambers, the via holes can also be used to provide increased pathlengths for optical and other detection. For example, FIG. 29 shows a microchip 230 where the via hole 231 is being used both to perform real-time PCR and as a detection cell. The detection can also be enhanced by using internally reflecting materials for the coating of the via hole or for the wafer substrate.

6. Applications, Instrumentation, and Software

In some embodiments, a microchip can be held in a fixed position on a vacuum chuck. A microchip interface device can dock with the microchip to provide the external control elements including external pneumatics, thermal cycling temperature control elements, temperature control, and reagent introduction lines.

Figure 16:
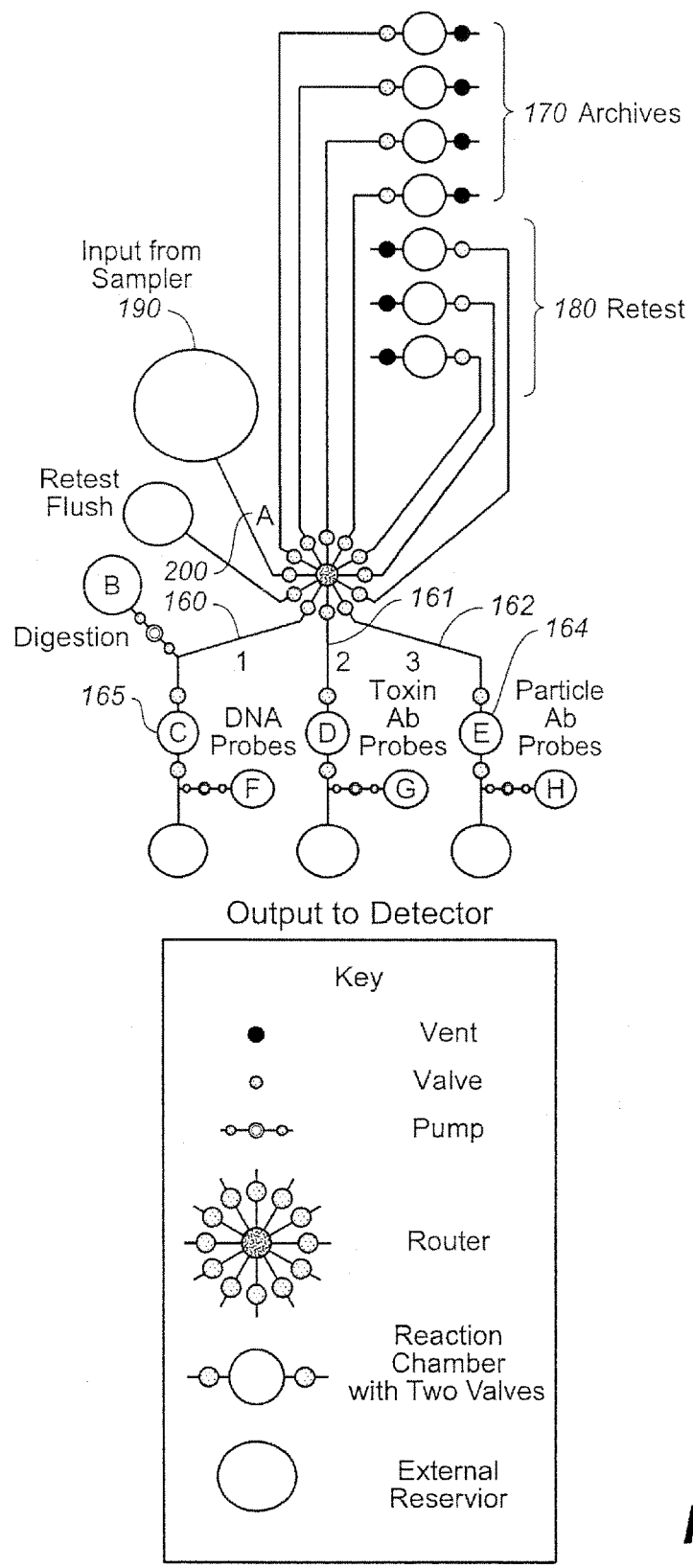
FIG. 16 illustrates an embodiment of a microchip cartridge using externally actuated MOV valves and pumps.

FIG. 16 shows an embodiment of a microchip cartridge designed using externally actuated MOV valves and pumps to control flows, with the larger central diaphragm valves also functioning as reaction chambers. The cartridge contains three main channels for bioprocessing 160-162, a storage area 170, and reservoirs 180. One of these channels can be dedicated to processing for DNA-based analysis and the second and third channel to processing toxins and particles respectively by immunoassay analysis. The layout shown in FIG. 16 is one of many possible layouts and is designed to interface with a downstream single molecule detector for biodefense applications.

In some embodiments, the cartridge can function as follows. A 100 µL sample is delivered into an input reservoir 190 on the cartridge by an off-chip sample concentrator after addition of internal controls. Seven unprocessed 10 µL aliquots are pumped by the router labeled "A" 200 from the reservoir into on-cartridge storage chambers held at 4° C.

Three of these aliquots are for retesting 180 and possible confirmation if analyzed samples test positive; the additional four aliquots 170 are for later retrieval and forensic analysis in the event that initial positive detection is confirmed by the retesting. All aliquots are be stored cooled on the cartridge by an external cooler such as the TEC Peltier cooler; stabilization reagents, if needed, may be stored dry in these reservoirs. After use of a cartridge, the used cartridges will be stored in a refrigerated mini-carousel.

The aliquots for immediate processing are then formed and processed. A 10 µL test aliquot is moved via router A 200 into bioprocessing channel 2 161 to chamber D 163 for immunolabeling for detection of toxins, as described below. A second 10 µL test aliquot is moved via router A 120 into bioprocessing channel 3 160 to chamber E 164 for immunolabeling for detection of intact bacterial or viral particles, as described below. The input reservoir is then capped from above and the remaining sample sonicated using an external sonicator horn coupled through the bottom of the cartridge. The ultrasonic waves generated disrupt vegetative cells, spores, and viruses, and shear DNA to reduce the viscosity for improved hybridization kinetics and flow properties. The lysed sample is moved via router A 200 into bioprocessing channel 1 162 to chamber C 165 for hybridization with labeled probes for DNA analysis.

The bioprocessing of the three channels can occur simultaneously. A sample digestion step to degrade RNA, proteins, and lipids may be desirable to reduce the background of the sample for DNA-based single molecule detection and decrease the demands on the downstream detector. If this processing is performed (such as for single molecule detection), the DNA analysis sample can have a cocktail of RNAse, proteases, and lipases in buffer added to degrade non-DNA material. The addition can be by pumping the material from reservoir B into chamber C with the sample. If necessary, the sample and digestion reagents can be pumped back and forth between the adjacent chambers to mix. The aliquot in chamber C can be labeled for DNA analysis by hybridization with DNA probes from reservoir F. Hybridization or antibody probes can be stored cold in reagent cartridges and added to the cartridge using external pumps immediately before use of individual bioprocessor units. The probes can be pumped into the chamber using the on-cartridge pumps to mix the reagents. Again samples and reagents can be pumped back and forth between the probe chamber and reaction chamber C to further mix, as needed. The fixture can contain heating elements beneath the chambers. For hybridization, the flanking valves can be closed and the chamber heated to 95° C. to denature the DNA and then cooled to the hybridization optimum to hybridize the DNA probes to any targets present. These valves seal sufficiently to perform PCR in these chambers, therefore, evaporation can be substantially eliminated.

The above-described BPM can be applied to any PCR-based assays, such as individual or multiplexed PCR, variable number tandem repeats (VNTR), multi-locus VNTR analysis (MLVA), or other assays. The hybridization probes can be replaced with the appropriate PCR primers and the external heat source cycled. The digestion step can be replaced by a restriction digestion to implement amplified fragment length polymorphism (AFLP). For toxin detection, the aliquot in chamber D can be mixed with antibody probes to toxin from reservoir G, while for particle detection the aliquot in chamber E can be mixed with antibody probes to microbial surface coats from reservoir H and the samples held at 37° C.

Following labeling, the bioprocessed samples can be pumped into three external reservoirs where they can be picked up by suction for analysis by the detector. Alternatively, capillary electrophoresis or optical detection can be performed on a modified version of the microchip.

If the detector only detects the internal controls, the cartridge can be rotated and the next bioprocessor unit prepared. If the samples test positive, the bioprocessor unit is not rotated, but instead flushed from the retest flush reservoir and fresh reagents loaded. The three samples in storage for retest can be pumped back via the router, one directly to chamber D for toxic detection, a second to chamber C for particle detection, and the third into the input reservoir for sonication and DNA analysis. The retest samples can be processed as above and output to the detector for confirmation as possible presumptive positive detection events.

The instrumentation to operate the microchip can be contained in Microchip Interface Device which is the external instrumentation. The microchip can be developed with the microchip cartridge held on-top of a vacuum chuck and a microchip interface device that docks with the microchip having pneumatics, heating and cooling, and syringe pumps to move reagents into reservoirs. The computer-controlled microchip interface device can control solenoids to open and close external full scale valves that in turn control microchip valves and pumps to move samples on the microchip.

The microchip interface device can include a heater, such as a resistive heater like nichrome, a Peltier heater, an air-based heater, a infrared heater, or other embodiments well known to one skilled in the art and thermocouple or other temperature measurement device and associated control circuitry and software to control the temperature and heating and cooling rates of a region of the microchip. Cooling can be by radiant cooling, active cooling from a fan, cooling by a Peltier, cooling by water or other methods well known to one skilled in the art. The temperature of the entire microchip can also be set by heating the vacuum chuck.

Syringe pumps can be controlled to deliver reagents to reservoirs on the mounted microchip or pressurized chambers containing reagents can have a valve that is opened to allow reagent to flowthrough a tube into a reservoir on the microchip. In some embodiments, gravity flow can be used. In some embodiments, electric forces to move reagents, and magnetic delivery of reagents attached to beads or particles is within the scope of the present disclosure. All of the above mentioned hardware and the NanoPrep software can be controlled using the Laboratory Rapid Automation Toolkit software or other software.

Figure 26:
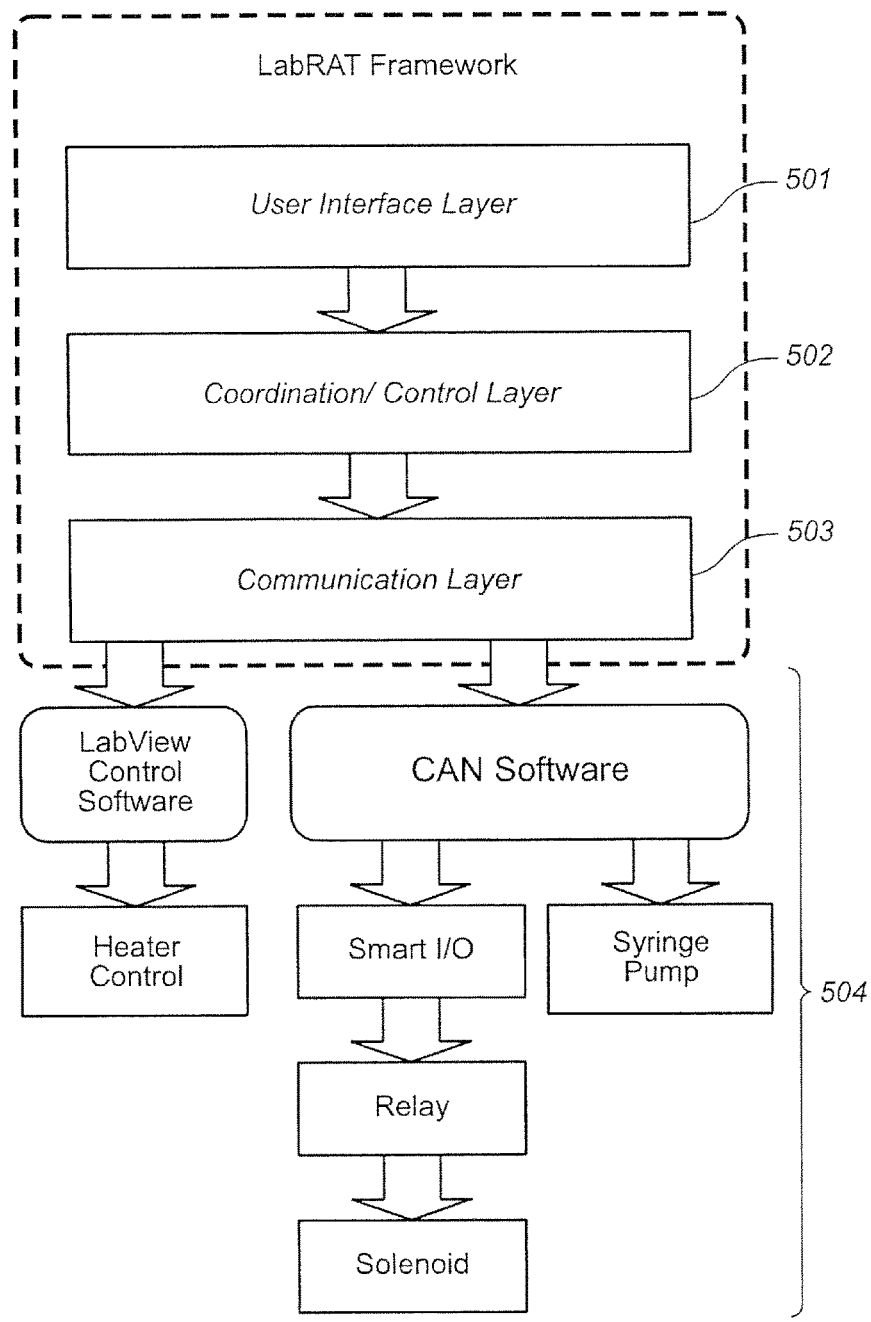
FIG. 26 illustrates an embodiment of instrument control of a microchip interface device.

The Laboratory Rapid Automation Toolkit (LabRAT™) software platform 500 (FIG. 26) is an instrumentation software development kit to allow the rapid creation of robust, commercial grade software platform to drive instrumentation and automate processes. LabRAT defines a set of communication and command protocols 501-503 and has a standardized automation architecture and framework that is simpler, more flexible, and more efficient than anything commercially available. The LabRAT framework is based on a core set of technologies that can span multiple operating systems, development languages, and communication media 504.

At the heart of the LabRAT automation architecture is an instrument communication and control interface protocol based upon XML-RPC (extensible markup language-remote procedure calls), the core of SOAP (simple object access protocol) standards. XML-RPC is an excellent mechanism for inter-process communication: it is simple, fast, robust, has widely available implementations for nearly every current software development system, operates over TCP/IP and HTTP, and is easy to implement. XML-RPC operates as a very high level "meta-mechanism" and can tie disparate components together into a tightly ordered instrumentation system. In addition to the core communication and command protocols, a set of interfaces suitable for laboratory instrumentation have been defined and implemented to exchange of "lab services" between components.

LabRAT or similar software has been adapted to control the microchip interface device. The existing LabRAT software provides the functionality for all layers once drivers for the individual components are "wrapped." The NanoPrep thermal cycler software to control localized thermal cycling is already incorporated into LabRAT. Pneumatic solenoids, syringe pumps, and other elements including detectors can also be controlled by LabRAT software. In addition, the interaction of different hardware components can be coordinated through LabRAT scripting commands In some embodiments, three hardware devices can be controlled: 1) heating and thermal cycling, 2) on-chip valves and pumps (operated pneumatically), and 3) syringe pumps to deliver reagents. The thermal cycling can be accomplished using nichrome heating coils located directly under reaction chambers and controlled by existing NanoPrep software and hardware. A MiniPrep Cartesian robot (Tecan) can be used to drive a "Smart I/O" board (Tecan) to operate up to 32 ttl output lines that control the mini-robotic valves and pumps on the microchip, and the full scale robotics used to load and unload samples on the microchip; the LabRAT CAN interface can also operate a high precision syringe pump to dispense fluid into the chip.

A Smart I/O board can drive Crydom solid state relay modules (one for each line, MODC-5 SSR Module, DigiKey #CC1226-ND and MS-4 4-Pos Mounting Board, DigiKey #CC1230-ND), which can in turn operate 24V DC solenoid valves (ARO, P251 SS-024-0)). These valves are 3-way, direct drive units with a common port and one each normally open and normally closed port (connected to vacuum and pressurized air lines respectively). The solenoids will control 8 full-scale vacuum and pressure lines that will operate via 8 manifolds (M1-M8 on the microchip). The control software can sequentially operate these solenoids in such a way as to create the pumping action that drives fluid within the channels on the chip. The robot control software can be in the form of an ASCII encoded script that is executed by the Express Script Engine (Tecan) in turn under control of LabRAT software. The existing LabRAT software provides complete functionality to operate an instrument using an advanced XML-RPC-based based framework.

The hardware to operate a microchip can be developed into a stand-alone instrument or combined with existing instruments. For example, a Tecan MiniPrep instrument can be used to pipette solutions on and off-chip as needed and a Tecan Smart I/O card to control the hardware that in turn controls the MOV valves and pumps.

Figure 27:
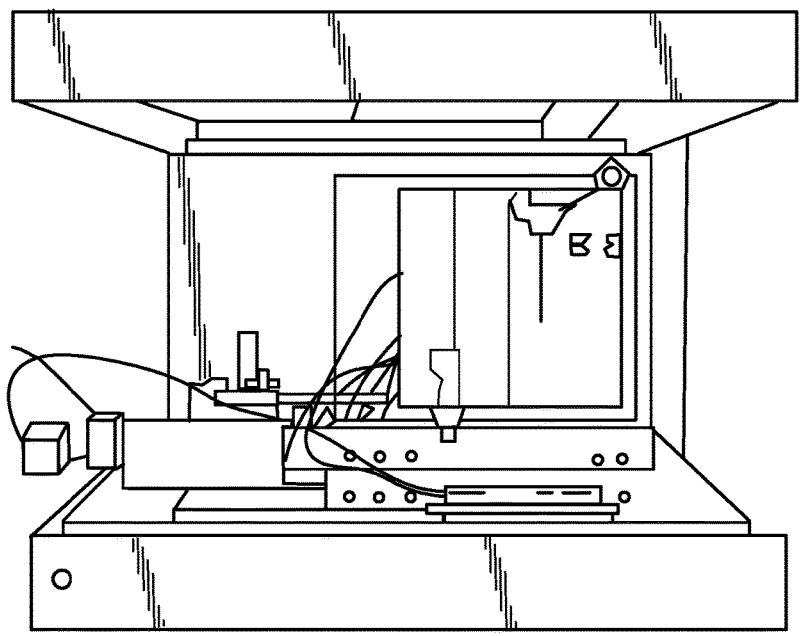
FIG. 27 illustrates an embodiment of a microchip vacuum chuck with tubing mounted in a MiniPrep instrument.

FIG. 27 shows an embodiment of a front view of a system using a MiniPrep robot with a microchip. In the foreground (right) of the stage, is the aluminum-alloy vacuum chucks. The chuck has a resistive heating element embedded in its "sandwich-type" structure that allows for global heating of the chip. The temperature controller is visible on the top of the leftmost black panel. From the left side of the chuck, the eight vacuum lines that drive the on-chip valves and pumps are connected via tubing to the vacuum manifold installed behind one of the Tecan panels (not visible in this photo). On the left side of the stage is a syringe pump (with attached syringe) to dispense "reservoir" reagents onto the chip.

Figure 28:
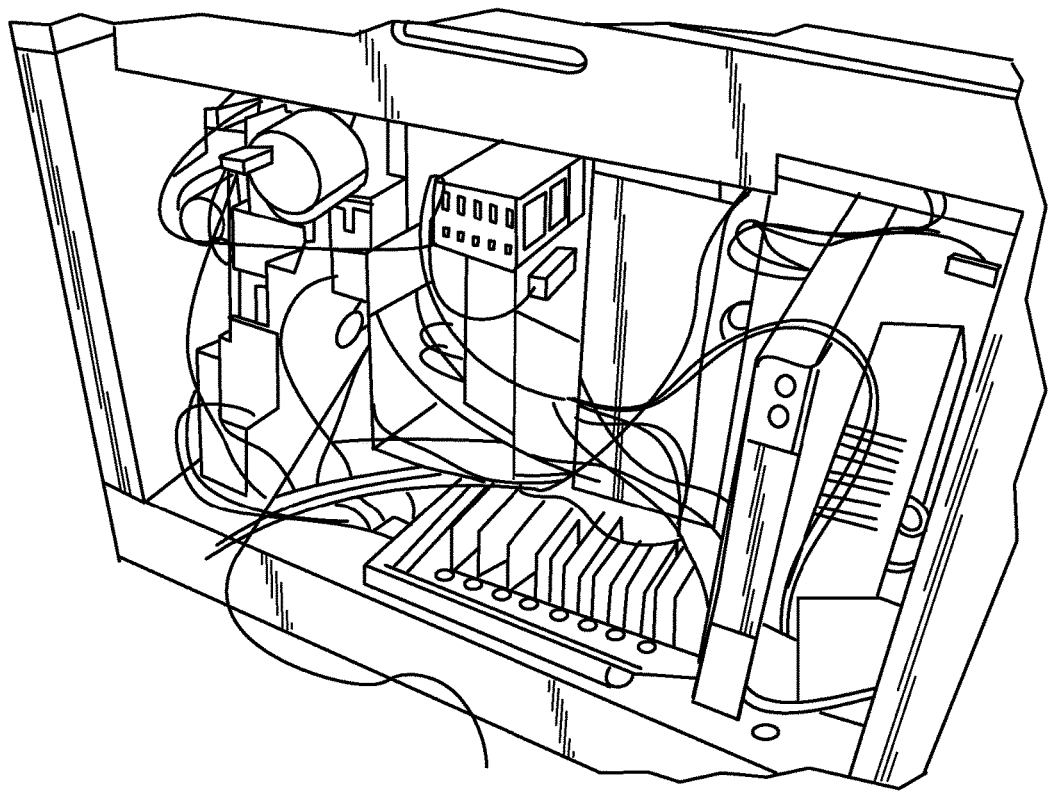
FIG. 28 illustrates an embodiment of associated hardware to operate a bioprocessor microchip inside a MiniPrep instrument.

FIG. 28 shows the inside of the MiniPrep (after removing the rear panel) containing many of the installed components including the temperature controller, the eight 24V DC solenoids, and the relay. The air pump and Smart I/O board are also mounted inside the MiniPrep, but are not visible.

Figure 15:
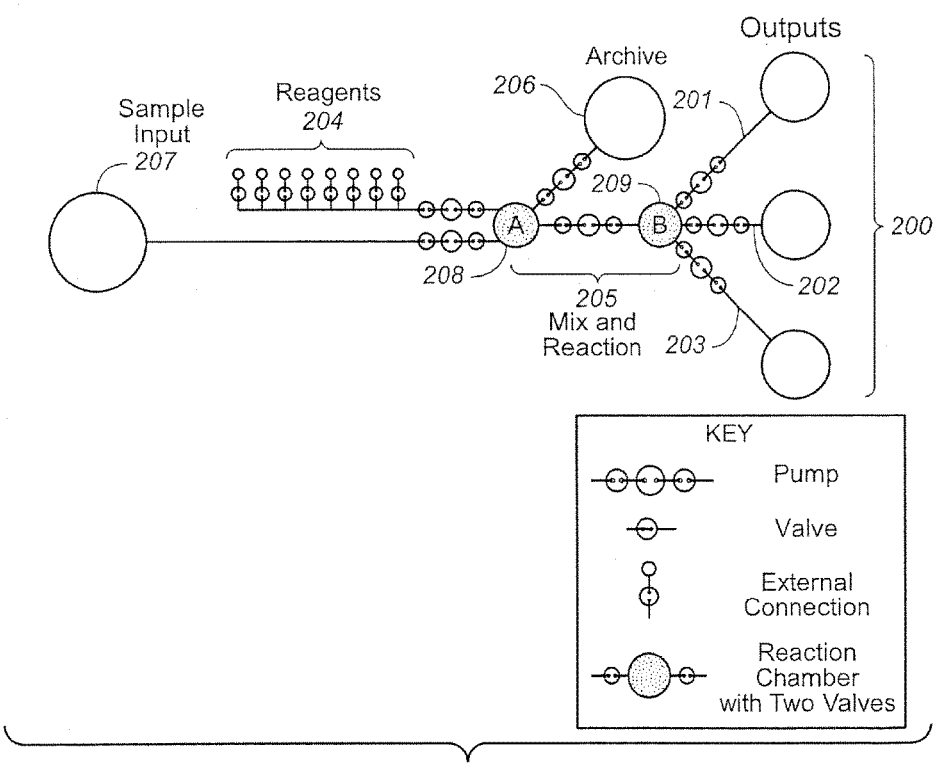
FIG. 15 illustrates an embodiment of a single bioprocessor unit.

The bioprocessor cartridges described herein can be designed to process the samples using microfluidic on-cartridge valves and pumps as control elements. The cartridge can be designed to employ these externally actuated valves and pumps to control flows, with the larger central diaphragm valves also functioning as reaction chambers. FIG. 15 shows one of the 12 identical bioprocessor units 200 on the cartridge. Each unit inputs a sample and prepares three bioprocessed output samples 201-203: 1) DNA analysis with DNA hybridization labeling, 2) toxin analysis with immunolabeling, and 3) particle analysis with immunolabeling. In addition, each unit can have areas for reagent addition 204, mixing and reaction 205, and archiving samples 206 for retest.

In some embodiments, a 1 mL sample can be delivered into an input reservoir 207 on the cartridge by an air sampler after addition of internal controls. The input reservoir may have a coarse filter incorporated to remove "large particulates" that might obstruct the channels. An unprocessed 700 µL aliquot can be pumped into the chamber labeled "A" 208 from the input reservoir into on-cartridge archive chamber 206 held at 4° C. The archive sample can be for 1) retesting and possible confirmation if any analyzed samples test positive and 2) later retrieval and forensics analysis in the event that initial positive detection is confirmed by the retesting. The archive sample can be stored cooled on the cartridge by an external cooler such as the TEC Peltier cooler; stabilization reagents, if needed, may be stored dry in these reservoirs. After use of a cartridge, the used cartridges can be stored in a refrigerated mini-carousel.

In some embodiments, 3 aliquots for immediate processing for DNA, toxins, and particles can be formed and processed. A 100 µL test aliquot for toxin labeling can be first pumped into chamber A 208 and reagents for immunolabeling and detection of toxins can be pumped in. The sample can be pumped back and forth to chamber B 209 if needed to mix the sample and reagents. The sample can be pumped into the output reservoir 201-203 for incubation and transfer to the detector. A second 100 µL test aliquot can be moved into chamber A 208 for immunolabeling for detection of intact bacterial or viral particles. Antibody probes to microbial or viral surface coats can be pumped into chamber A 208 and the samples can be held at 37° C. The antibody probes can be complex mixtures of antibodies that can be then discriminated in the detector. Following labeling, the bioprocessed particle sample can be pumped into the reservoir to be picked up by suction into a capillary for analysis by the detector.

For DNA sample preparation, after processing the aliquots and samples for toxin and particle detection, the input reservoir can be capped from above and the remaining sample sonicated using an external sonicator horn coupled through the bottom of the cartridge. The ultrasonic waves generated disrupt vegetative cells, spores, and viruses, and shear DNA to reduce the viscosity for improved hybridization kinetics and flow properties. The lysed sample can be moved into chamber A 208 for hybridization with labeled probes for DNA analysis from the reagent input 204. For hybridization, the fixture can contain heating elements beneath chamber A 208. The flanking valves can be closed and the chamber heated to 95° C. to denature the DNA and cooled to the optimum temperature to hybridize the DNA probes to any targets present. These valves seal sufficiently to perform PCR in these chambers, therefore, evaporation can be substantially eliminated.

A sample digestion step to degrade RNA, proteins, and lipids may be desirable to reduce the background of the sample for DNA-based detection and decrease the demands on the downstream detector. If this desirable, the DNA analysis sample can have a cocktail of RNAse, proteases, and lipases in buffer added from the reagent inputs 208 to degrade non-DNA material. The addition can be by pumping the material into chamber A 208 with the sample. If necessary, the sample and digestion reagents can be pumped back and forth between the adjacent chambers A 208 and B 209 to mix. In the event that digestion is desirable, the digested aliquot in chamber A 208 can be labeled for DNA analysis by hybridization with DNA probes as herein.

Hybridization or antibody probes can be stored cold in reagent cartridges and added to the cartridge using external pumps immediately before use of individual bioprocessor units. The probes can be pumped into the chamber using the on-cartridge pumps to mix the reagents. Again samples and reagents can be pumped back and forth between chambers A and B to further mix if necessary. Future implementations may have reagents preloaded in the bioprocessor cartridges.

In some embodiments, if the detector only detects the added internal controls, the cartridge can be rotated and the next bioprocessor unit can be prepared. If the samples test positive, the bioprocessor unit is not rotated, but instead flushed with buffer from the reagent input. A 100 µL sample in storage can be pumped back into chamber A for retest starting with the process that tested positive. The retest samples can be processed as above and output to the detector for confirmation as possible presumptive positive detection events. LabRAT™ software can be used to control the syringe pumps, thermal cycling heating element for Chamber A, and the full scale solenoids to actuate the on-chip valves.

Chemistry for hybridization and antibody binding can be individually optimized in the cartridge based on the full volume or macroscale volume results. The concentration of reactants, reaction times, and temperature can be re-optimized for the cartridge format and the impact of a range of input microorganisms tested in reconstruction experiments using spiked air samples. Determining the storage conditions for reagents is within the abilities of the skilled artisan. All reagents can be stored at 4° C. in reagent cartridges; additional stabilizers such as osmoprotectants (trehalose, glycine betaine) or other agents may be added to extend the shelf life.

In some embodiments, the strategy for mixing can be to place the two streams to be mixed in a channel with one stream on top of the other in the thin etched dimension. The short path between the streams enhances the mixing. An alternative mixing strategy can exploit the presence of beads, such as magnetic beads, in the reaction chamber or their addition to disrupt laminar flow by magnetically manipulating the beads. In some embodiments, this can force the target analytes in one stream to enter the "other" stream, which can be used to initiate processing or analytical reactions. In some embodiments, weirs can be used to trap beads as needed. In some embodiments, the beads can be flushed out into waste after use.

Reagent stabilization can be a critical issue for various embodiments of the disclosed systems, e.g., field devices. Therefore, in some embodiments, the reagent reservoirs can be temperature controlled using Peltiers to cool to 4° C. In some embodiments, reagents can be stabilized with Ready-To-Go™ chemistries or other freeze-drying methods using osmoprotectants, such as trehalose or glycine betaine, and then rehydrated before use. The concept with rehydration can be daily or weekly aliquots of stabilized reagents in ampoules with breakable seals. Water or buffer can be pumped into the ampoules in the instrument to hydrate the stabilized reagents to provide daily or weekly working stocks. The working stocks can be moved into the syringe pumps or loaded directly in a bioprocessor depending on the stability.

a) Microbead Integrated DNA Sequencing (MINDS) System

In some embodiments, MINDS system can prepare and analyze sequencing samples with ultra-low consumable costs using automated, unattended preparation and analysis of Sanger samples. The sequencing templates can be prepared on beads starting from sheared chromosomal or BAC DNA in a bulk emulsion PCR reaction with each bead carrying DNA derived from a single DNA fragment. Following sorting to eliminate beads without fragments, individual beads can be delivered to a low volume (e.g., 25 nL) cycle sequencing reaction chamber integrated on a 400 channel microchip together with cleanup and µCAE analysis. In some embodiments, the bead can be trapped by a weir, cycle sequencing can be performed for both forward and reverse paired-end reads and the products electrophoresed into dual sample cleanup chambers, containing an affinity gel capture matrix for either the forward or reverse read. The affinity gel can be washed to remove ions and unincorporated nucleotides. The purified cycle sequencing fragments can be eluted from the affinity matrix by increasing the temperature, and then injected into a folded CE channel for electrophoretic analysis. This approach can drive reagent volumes and costs down by orders-of-magnitude in part because it can perform sequencing at a scale close to the fundamental limits dictated by the number of molecules In some embodiments, an integrated MINDS system can automate and miniaturize all processes for shotgun sequencing, directed sequencing, and resequencing. The MINDS System can create a microbead-based fluorescent DNA µCAE sequencer with 100-fold, or more, lower operating costs that leverages the existing sequencing infrastructure. Each system can perform completely automated sequencing with unattended operation for up to one week with mini-robotic microfluidics replacing full-scale robotics.

The MINDS System can be implemented in modules, which are then integrated. In some embodiments, a 200 nL cycle sequencing microchip-based module can be used. A DNA Analysis Module based on an advanced, rotary LIF scanner is constructed as a platform module for the MINDS System with µCAE microchips that can clean up pair-end read samples with dual affinity capture chambers before injection into pairs of electrophoretic channels using the advanced matrices. These five-layer microchips can be operated by the MOV valves and pumps, with microfluidics "servicing." The cycle sequencing module can be combined on-chip to produce a Core MINDS chip that integrates 100 nL cycle sequencing, sample cleanup, and separation. In some embodiments, a complete MINDS chip with 25 nL sample preparation can input a microbead library and output sequence information is enabled.

b) Cycle Sequencing Module

A microfluidic Cycle Sequencing Module (CSM) can be used as a stand-alone function and as a module in a microchip-based sample preparation for the MINDS System. The CSM can include: 1) a microchip that contains the sample preparation microfluidic with on-chip valves and pumps to control flows, and 2) an external interface to operate the microchip through the on-chip valves and pumps. The sample preparation CSM can be a 16-channel scale with 200 nL cycle sequencing volumes with off-chip analysis by capillaries (CAE) and microchips (μCAE). In some embodiments, a microchip interface device (MID) with external fluidic interfaces, heating, and pneumatic actuation, can be scalable to 400 or more channels.

Figure 14:
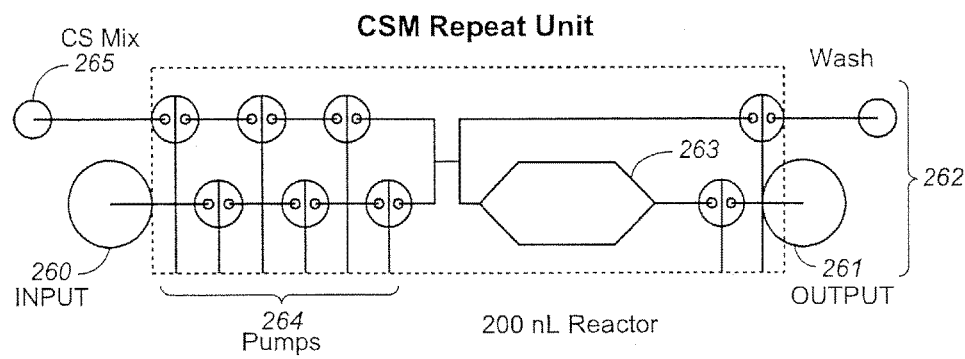
FIG. 14 illustrates an embodiment of a cycle sequencing module (CSM) repeat unit.

In some embodiments, a 16-channel 200 nL cycle sequencing sample preparation microchip device with on-chip valves and pumps can be used. Two channels of a simplified microchip cartridge are shown schematically in FIG. 14. The reservoirs labeled "Input" 260 and "Output" 261 are essentially holes in the upper layer of the microchip 262 that can be connected to the microfluidic channels. The device can take input DNA samples (PCR, plasmid, or other templates) from microtiter plates, perform cycle sequencing at 200 nL volumes, and output fluorescently labeled cycle sequencing products into microtiter plates ready for sample cleanup and injection into CAE instruments or μCAE analysis. The microchip can be operated by the microchip interface device, which in turn will be driven by LabRAT™ software. The CSM microchip interface device can provide the mechanics to 1) open and close on-chip valves, 2) operate on-chip pumps, 3) meter cycle sequencing reagents from storage onto the microchips, 4) control the heating and cooling to perform the cycle sequencing, and 5) regenerate the chip with buffer and wash solutions. The microchip and the MID can be mounted on the deck of a Tecan MiniPrep fluid handling robot that can perform fluidic transfers.

In some embodiments, a 200 nL CSM microchip can be operated as follows. Samples can be loaded from microtiter plates into the wells of the Input 260 reservoirs by the Tecan MiniPrep robot. The MOV on-chip pumps 264 can move aliquots into the reaction chambers by controlling the pumping using external actuation of the vacuum/pressure lines that drive the on—chip pumps, as described in FIGS. 9-10. The cycle sequencing mix 265 (CS Mix, FIG. 14) can be pumped by its on-chip pumps to dispense dye terminator cycle sequencing master mix into the reaction chamber 263. The MID, under computer control, seals the three valves surrounding each reaction chamber 263 and thermal cycles the reaction mix. Upon completion, the 200 nL samples can be pumped by the on-cartridge pumps into the Output reservoirs 261 which will contain 5 μL of water. The diluted samples can be moved by the Tecan into 35 μL of alcohol in a microtiter plate for subsequent off-chip post-processing and analysis. In some embodiments, the samples can be moved to dual affinity capture chambers for cleanup and analysis. The CSM cartridge can be flushed with buffer to remove residual DNA template, reloaded with new samples and the process begins again. Cycle sequencing can tolerate greater than 5% contamination with template from a previous reaction: therefore flushing the reaction chamber can regenerate the microchip. In some embodiments, each microchip can be reusable for hundreds of reactions.

c) CSM Instrumentation

Features of instrumentation to operate a CSM can include: 1) automated external actuation of on-chip mini-robotics that control movement of liquids in the CSM microchip-based cartridge, 2) control of the external heating and cooling for the thermal cycling, 3) drive syringe pumps to deliver cycle sequencing reagent to the chip and 4) control of a Tecan MiniPrep robot to move samples into the Input reservoir from microtiter plates and take prepared cycle sequencing samples from the microchip Output reservoir to microtiter plates. All four elements can be controlled through LabRAT software.

The thermal cycling can use heating and cooling from external sources to simplify microchip fabrication and reduce operating costs. Some embodiments use groups of resistive heating coils with cooling from a fan. In some embodiments, nichrome heaters placed on top of microchips with thermocouple sensors can be used and can have ramp times of over 30° C./sec. In some embodiments, heaters can be implemented at the 400 channel level, that are reproducible, and reliable without monitoring every channel. In some embodiments, an enclosure can be used for the cooling air to prevent it from altering the temperature of other parts of the microchip when the sample preparation and analysis are integrated. In some embodiments, a high-performance Peltier-effect heat pumps can be used in strips to rapidly cycle temperatures at the reaction chambers. These various methods can use the existing NanoPrep thermal cycler software under LabRAT™ control.

A syringe pump, kept chilled by a Peltier heat pump, can be used to deliver the cycle sequencing reagents to the CS reservoir channel on the microchip and the reservoir replenished as on-chip pumps dispense reagent. Similarly, water or buffer to regenerate the microchip can be delivered and controlled. In some embodiments, syringe pumps can have 1 nL full step size and can be controlled by LabRAT™ software. In some embodiments, a solution with a simple gravimetric flow to replenish the reservoirs is possible; a mini-valve under software control can regulate flow.

In some embodiments, the CSM can be implemented on the deck of a Tecan MiniPrep. The Tecan can move the samples from a microtiter plate into the Input reservoir and pickup finished samples from the Output reservoir and move them into a microtiter plate. The Tecan has the capability to operate a single syringe pump with the tip mounted on a robot with X-Y-Z motion under CAN control. As mentioned above, the LabRAT software can control CAN devices using the Microsoft WSH controller. Scripting to move the liquid to and from microtiter plates is straightforward. The use of Tecan instead of manual pipetting permits the CSM to operate in a completely automated mode.

In some embodiments, CSM can include sampled cycle sequence on-chip and analyzed off-chip by both the Mega-BACE CAE and a μCAE microchip systems. Dye-terminator sequencing reactions can be performed essentially according to the manufacturer's specified protocols using DYEnamic™ ET Terminator Sequencing Kits (Amersham). In some embodiments, reagents can be be cycled at 95° C. for 25 s, 50° C. for 10 s, and 60° C. for 2 min for 30 cycles. After thermal cycling, the samples can be moved into the microchip Output reservoirs and transferred into 40 μL of 80% ethanol at room temperature in a microtiter plate by air pressure. For ethanol post-processing, the samples can be centrifuged at about 2,800 RCF for 45 min and the alcohol removed by a brief inverted spin for 30 s at 50 RCF. The samples can be resuspended in 10 μL of double distilled water.

Controls can include full volume samples prepared in microtiter plates and 500 nL and 200 nL NanoPrep samples prepared in capillaries. The samples can be injected into a 96-capillary MegaBACE instrument using a 10 kV, 15 s injection and separated using a 120 V/cm field strength. Four-color electropherograms can be processed using the Sequence Analyzer base-calling software package with the Cimarron 3.12 basecaller (Amersham Biosciences) and the Phred base-calling and quality score generating application as described. All readlengths can be reported as the Phred20 window, which is 99% accuracy.

The number of amplification cycles, reaction times, cycling profiles, and the concentration of different reactants, i.e., primers, polymerase, dNTPs, ddNTPs, etc, can be individually optimized as needed and is within the abilities of the skilled artisan. For example, the range of DNA concentrations tolerated can be determined and a matrix of the performance of a range of DNA-to-primer concentrations measured. Initially, the samples can be purified PCR products. When the CSM is optimized for PCR products, a series of actual samples representative of both unchallenging and challenging sequences can be tested for both CAE and µCAE analysis and compared with full volume sample preparation with CAE analysis results. The acceptance criteria can be equivalent data quality, readlengths, and success rates as compared to full volume sample preparation results. Controls will include full volume reactions and NanoPrep (500 nL and 200 nL volumes) reactions.

Uniformity can be addressed both by heater and cooler design and by changes in the microchip layout. Surface interactions can be suppressed by additives such as BSA or PVA. The surface chemistry of the reaction chambers can be suppressed using either modified LPA, PEG, or other coatings. For glass, an alternate approach can be multipoint covalent attachment of the polymers such as polyethers and oxidized polysaccharides to many surface sites simultaneously, thus extending the lifetime of the surface immobilization since many sites must be hydrolyzed to free the polymer.

d) Integrated MINDS System

In some embodiments, a complete MINDS system can include three modules—a Bead Library Module, a Cycle Sequencing Module, and a DNA Analysis Module. In some embodiments, a complete MINDS system can analyze a bead-based library on a 400 channel MINDS microchip which integrates 25 nL paired-read cycle sequencing, paired affinity capture cleanup, and µCAE separations on folded microchannels with hyperturns. The MINDS System can be a completely automated system for shotgun sequencing or for resequencing, depending on the bead library construction. In some embodiments, the Cycle Sequencing Module and DNA Analysis Module can be integrated and prepared samples, such as PCR or purified plasmids, can be used as the input samples. In some embodiments, the PCR or other amplification can be performed on the microchip.

The DNA Analysis Module can include a rotary scanner (FIG. 30) and can perform paired-end read sample cleanup on microchips and then inject the samples into two separate µCAE channels for separation and detection of the forward and reverse sequencing reactions. The detector can be a rotary LIF scanner with 488 nm excitation and four-color detection. To create a Core MINDS System, a Cycle Sequencing Module can be integrated with the DNA Analysis Module instrumentation. This core system can integrate 100 nL cycle sequencing, paired affinity capture cleanup, and separation on the same microchip. Beads containing the PCR fragments that have been sorted by a FACS instrument can be delivered to the microchip and individual beads can be routed into 25 nL cycle sequencing chamber.

i) DNA Analysis Module

The DNA Analysis Module can perform sample cleanup of paired-end reads and µCAE to separate and detect labeled DNA fragments from each paired-end read. The cycle sequencing can use primers in both the forward and reverse direction that each have a unique affinity capture sequence, inserted in the vector. Paired cycle sequencing samples, from full volume, nano-scale preparation, or the CSM, can be loaded into reservoirs of an analysis microchip with a radial design. The samples can be electrokinetically moved into two sample cleanup chambers containing an affinity capture oligonucleotides for either the forward or reverse read. The cycle sequencing sample can be concentrated to a volume of approximately 20 nL while ions, unincorporated dyes, templates, nucleotides, and enzymes pass through into waste. The concentrated and cleaned sample can be released by raising the temperature and injected into a twin T injector for separation in a microchannel filled with separation matrix. The radial channels converge on a circular detection region where the microchannels can be scanned and detected.

The module hardware components include 1) a LIF rotary scanner which can accommodate a number of different microchip sizes and designs, 2) microchips, 3) electrophoresis controls, 4) temperature control, and 5) microchip regeneration. The DNA Analysis Module can be part of a fully integrated and automated MINDS system.

Some embodiments create an extremely sensitive scanning system with as much as 10-fold improved detection performance compared to existing rotary scanners. A 10-fold improvement can be obtained by extracting small (1.5 to 3-fold) multiplicative improvements in the scanner, microchip design, and dye chemistry. For the scanner, the best quality PMTs, dichroics, and mirrors can improve optical efficiency and can be coupled with a high power (200 mW) compact laser with a high numerical aperature lens. The dye chemistry can be improved with brighter dyes employing a cyanine donor. The microchip can have very deep etching in the detection region to improve detection with extra path length and to improve the resolution by sharpening bands. A reflective surface in the microchip sandwich and micro-optics can enhance light collection. Finally, the direct injection method, described below, can allow the complete cycle sequencing sample to be loaded into the separation channel. By carefully optimizing each element, the limit of detection can be significantly improved, compared to the current research versions, as the amount of labeled fragments needed for robust sequencing is decreased in parallel.

Rotary Scanner and Instrumentation. In some embodiments, an up-looking, rotary confocal laser-induced fluorescence scanner can be used to interrogate radial µCAE devices. The rotary scanner includes a rotating objective head coupled to a four-color confocal detection unit. Rotary scanning has the fundamental advantage of providing high scan rates with high positional accuracy and speed uniformity. Rotary scanning can be compatible with any radial wafer device 10-, 30-cm, or larger diameter wafers with as few as 1 to over 384 channels. Therefore, chip design can be tailored for various applications, e.g., long lanes for de novo sequencing and short lanes for resequencing.

Figure 30:
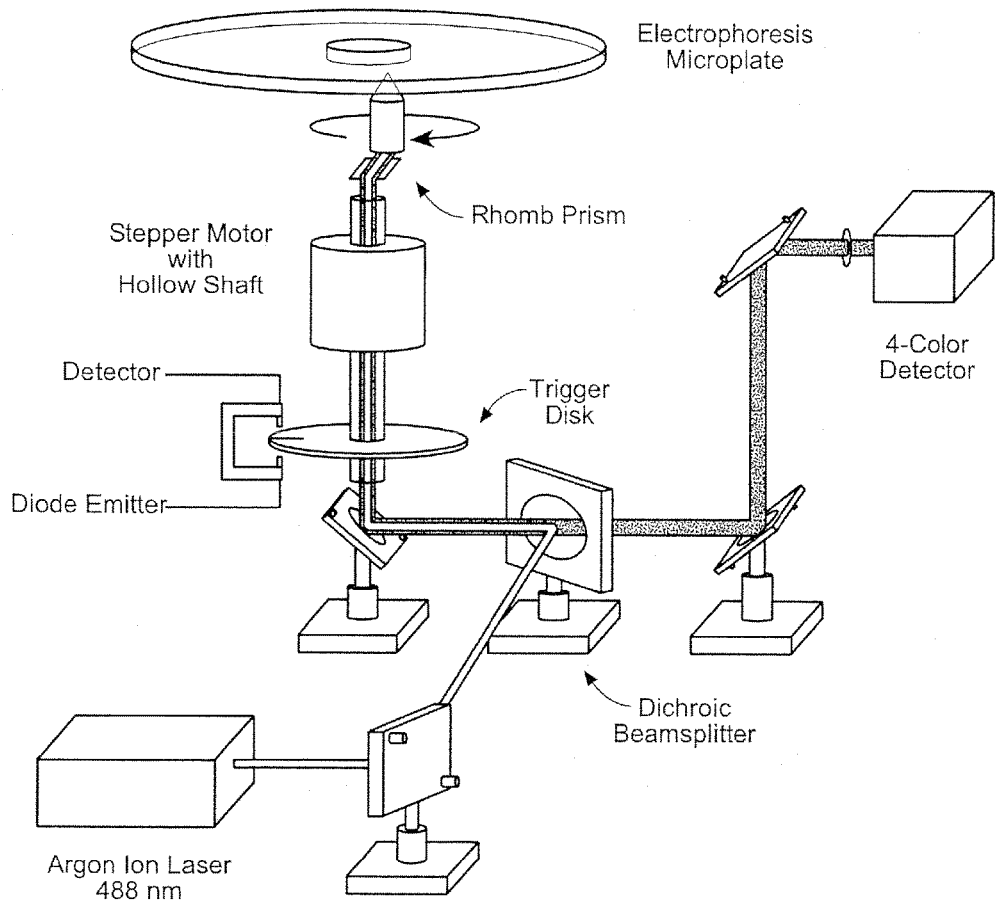
FIG. 30 illustrates an embodiment of a rotary scanner.

A schematic of an example of a rotary scanner is presented in FIG. 30. A 200 mW, 488 nm laser (Sapphire™ OPSL, Coherent, Santa Clara) is reflected by a dichroic beamsplitter and mirrors through the hollow shaft of a stepper motor. At the top of the shaft, a rhomb prism displaces the beam 1 cm off the axis of rotation and a high numerical-aperture (>0.7) objective focuses it on the channels through the bottom layer of the microchip. Fluorescence is collected by the objective and passes back through the optical system where it is spectrally and spatially filtered before detection in a modular confocal four PMT unit with a Microstar IDSC board with 8 channels for DA. The stepper motor is run at 5 Hz which gives 5120 data points/revolution with a spatial resolution of 12 micron, about 8 data points across a typical 100 micron channel. A 5th channel is fed by a photodiode that is triggered by a slot in a disk that is attached to the scanner shaft; the start of data acquisition in the other four channels is referenced to the voltage rise in the 5th channel. This design is sensitive with detection limits of several pM of fluorescein at a scan rate of typically 5 Hz. In some embodiments, the data can be pre-processed and analyzed with a commercial basecaller.

In some embodiments, the DNA Analysis Module instrument can also have a microchip interface device to control electrophoresis and microchip regeneration. The microchip can be held in place by a heated vacuum chuck after positioning with an alignment tool. In some embodiments, the microchips can have ca. 600 run lifetimes. The chuck can have three points to adjust the elevation of the chip to keep the planar relative to the plane of the confocal detector. An electrode ring can match the reservoirs at the perimeter of the microchip; electrodes can be controlled by four high voltage power supplies (Stanford Research Systems, Model 3101). Microchip regeneration, described below, can be performed in place using a centrally located "umbilical cord" to provide flushing of used matrix and refilling, while reservoir cleanout and replenishment can be from a tube-in-tube design with the inner tube removing out material while the outer tube flows buffer or other solutions.

Microchips and Operation. In some embodiments, the microchips can incorporate affinity sample cleanup and separation channels in a four-layer device. Affinity capture cleanup with oligonucleotide capture sequence can be a robust solution for sample cleanup and concentration. In contrast to electrokinetic injection which can concentrate dilute samples on injection, without the concentration step on-chip, the Twin T injector performs a pre-separation as it loads and then performs a "heart-cut" injection, both of which work against detection of dilute samples. The inclusion of affinity capture on the separation microchip can allow the 200 nL CSM samples to be diluted to microliter volumes before loading because the affinity capture can re-concentrate dilute samples while removing unincorporated terminators, ions, and template. Therefore, the CSM and DNA Analysis Module can be designed separately and then integrated.

Figure 34:
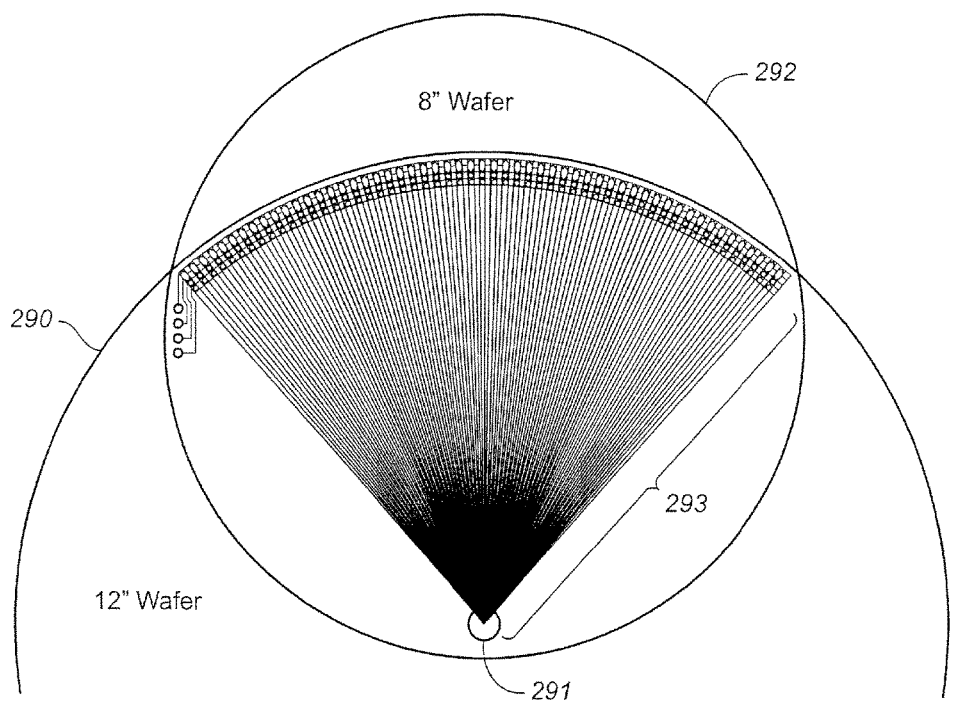
FIG. 34 illustrates modeling 12" wafers with 8" wafers.

In some embodiments, a MINDS system can use 12" wafers with radial designs 290 (FIG. 34), hyperturns and a central origin 291. In some embodiments, partial radial designs with 8" wafers 292 can be used that have the same channel densities and lengths as 12" designs that can have 400 channels and separation lengths of up to 45 cm, (achieved by folding the channels) depending upon the application. The 8" wafer can have about 108 separation channels 293.

Figure 21:
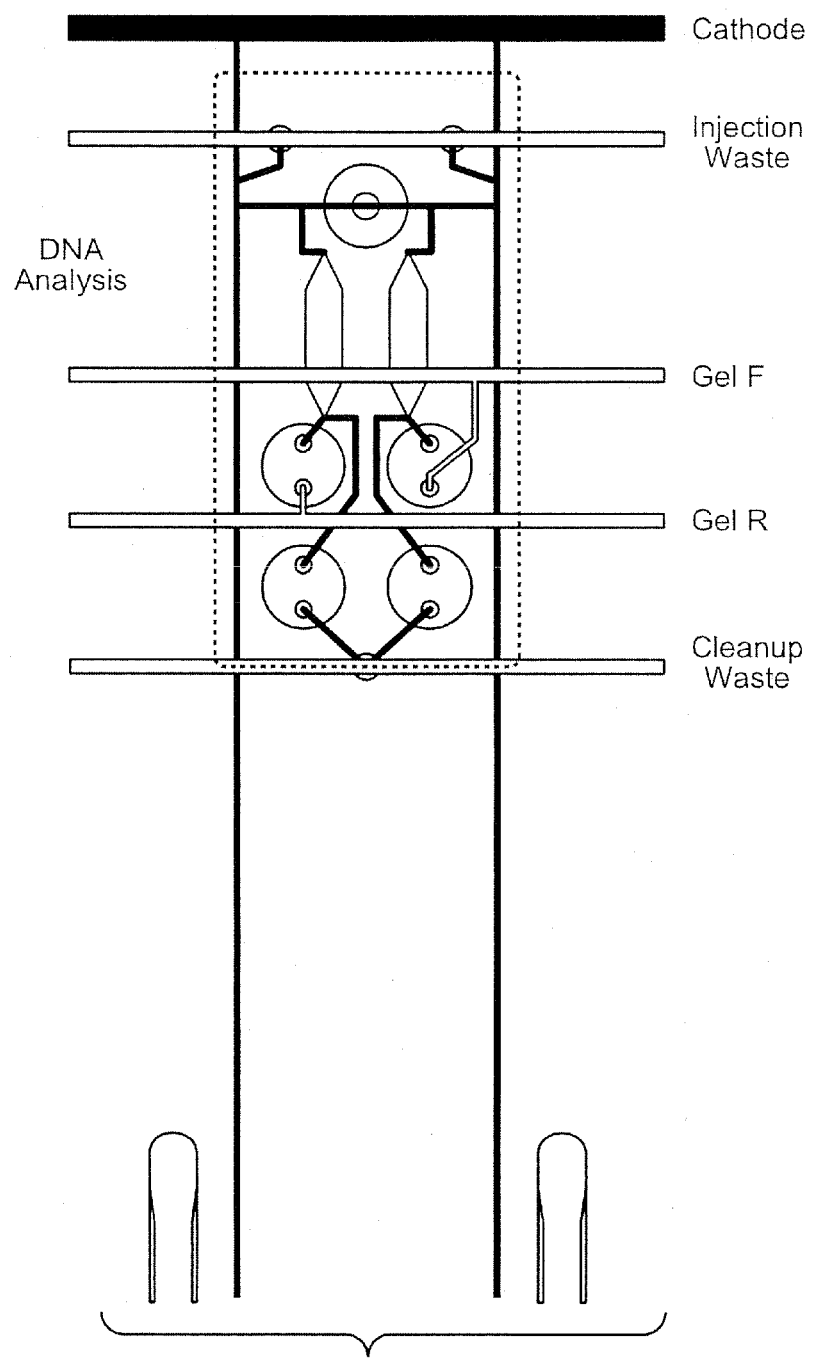
FIG. 21 illustrates an embodiment of a dual paired-end read affinity capture sample cleanup with dual analysis channels. The dark layer is microfluidic, gray lines are the service layer. Valve actuation layer is not shown. The light dashed box defines the DNA Analysis repeat unit.

FIG. 21 illustrates one embodiment of an 8" wafer. In various exemplary embodiments, this 8" wafer can have either straight 14 cm separation channels for short reads or folded channels up to about 45 cm for long reads. Samples can be pipetted into a single loading reservoir that connects to two affinity capture chambers that in turn each feed a separation channel. After the samples are loaded, an electrode ring with electrodes can be lowered and each cycle sequencing sample electrophoresed onto two affinity capture sample cleanup chambers, each with matrix to capture and concentrate either the forward or reverse read while removing the undesired components of the cycle sequencing reaction mix. The forward or reverse read can be released by heating the chamber to >65° C. and electrophoresing each read separately into a twin T injector for analysis. Thus each loading reservoir serves two separation channels. After separation, the separation matrix can be replaced. Matrix can be pumped in through a central "umbilical cord" which contains tubing for matrix and flush solutions as well as the electrical connection for the central common anode buffer reservoir. A number of geometries and designs can be used for the 400 channel MINDS microchip. The separations can be performed in many CAE matrices.

In some embodiments, the microchip can be held on a vacuum chuck on a Peltier heater to control temperature for optimal separation conditions and for matrix manipulation as needed. Following separations, buffer can be flushed through the umbilical cord to displace the used matrix. A manual tube-in-tube vacuum suction unit in the microchip interface device can remove the used buffer and matrix from the reservoirs. Fresh matrix can be added through the central chamber; matrix sensors may be incorporated to provide feedback to minimize matrix waste. In some embodiments, the replacement of matrix can be controlled with precision pumping which only replaces slightly more matrix than the column length. Either method can reduce matrix use by up to 10-fold. Buffer can be replenished into the reservoirs by the outer tube of the tube-in-tube while matrix is vacuumed by the inner tube. Affinity sample cleanup matrix can also be replaced as needed using service lines, as described herein.

In some embodiments, the microchips can last for 600 runs with clean samples. Microchip performance can be monitored by the software and operators alerted by LabRAT by e-mail, paging, or on-screen display as performance degrades. The replacement of the microchip can be done manually by the operator. In some embodiments, removal of a used microchip can entail unplugging the umbilical cord, electrode ring and actuation bundle for the on-chip valves and pumps, before releasing the microchip. The installation of new microchips can be facilitated by an alignment tool to properly position the microchip. The alignment can be verified by the detection of alignment marks and focusing of the optics either manually with software assistance or completely automated.

Microchip Fabrication. In various exemplary embodiments, the microfabrication process can be as described by Liu et al. 2000. *Proc. Natl. Acad. Sci. USA* 97(10):5369-5374 and Anderson et al. 2000. *Nucleic Acids Res.* 28:e60. Generally, Borofloat glass wafers (Schott, Yonkers, N.Y.) can be pre-etched in concentrated HF, then an amorphous silicon mask deposited by CVD or sputtering. In some embodiments, chrome-gold can be used in place of the amorphous silicon. An adhesion layer of HMDS can be coated on the top of the amorphous silicon, the wafer spin-coated with a thin layer of photoresist (Shipley, Santa Clara, Calif.), and soft-baked. The photoresist can be patterned with UV light through a mask having the desired channel pattern. After the photoresist is developed, the exposed amorphous silicon can be removed and the channel pattern chemically etched into the glass with concentrated hydrofluoric acid, to depths of about 40 µm for the channels on the fluidic wafer and about 70 µm deep for the manifold wafers. However, determining the depths of the various components is within the abilities of the skilled artisan. The residual photoresist and amorphous silicon can be stripped off. Access holes, 250 µm or smaller, can be drilled in Borofloat via wafers using a CNC-minimill with diamond drills. In some embodiments, smaller holes can be drilled with a custom laser. For production, ultrasonic drilling can drill all holes simultaneously. After a final cleaning in $H_2SO_4/H_2O_2$, the fluidic wafer and via wafers can be aligned so that the via holes are properly positioned with the channel gaps and thermally bonded at about 570° C. in a vacuum oven with a via wafer to produce a two layer µCAE chip. For 5 layer microchips, the three glass wafers can be aligned and assembled first; two of the glass layers can be thin wafers. The manifold wafer and the 254 µm thick PDMS membrane (Bisco Silicones, Elk Grove, Ill.) can be cleaned in a UV ozone cleaner and the four or five layer microchip assembled. The UV ozone treatment can produce an irreversible glass-PDMS bond. The finished microchips canl be diced to product the individual CSM microchips or used whole for MINDS microchips.

In some embodiments, microchips can be made in plastics and other materials using methods such as injection molding, hot embossing, lamination, and other well known methods to replicate a design. The application of these fabrication methods to make microchips are within the scope of the present dislcosure.

Characterization of the DNA Analysis Module. In embodiments employing the rotary scanner, the limits of detection can be measured with flowing dye solutions and the water Raman peak (from two peaks, 577.6 nm and 589.4 nm) measured as an internal standard. The performance of the sample cleanup and separation microchip with the DNA Analysis Module can be characterized using standards of full volume PCR reactions followed by a dilution series of the standard PCR products. The parameters for sample cleanup (e.g., loading, wash, and elution conditions) and injection and separation (times, voltages, separation temperature, buffer concentrations, etc.) can be optimized using methods well known to one skilled in the art. Quality values, success rates, and readlengths can be measured and compared with test and real samples. In some embodiments, readlengths can be about 600 bases or more. In some embodiments, the regeneration of the affinity capture can be tested and the number of runs before performance degradation can be measured. The partial replacement of urea with DMSO in the separation matrix can decrease run times and produce long readlengths in capillaries. In some embodiments, microchips can be run repeatedly with standard samples to determine microchip lifetime with the different matrices or coatings. For example, to shotgun sequence to 8×a BAC library can take about 22 runs of a 100 channel DNA Analysis Module microchip.

ii) Integrated Cycle Sequencing Module with DNA Analysis Module

Combining the features of the CSM with the DNA Analysis Module can produce a Core MINDS System. The basic unit design of the CSM microchip described above and in FIG. 14 can be ported onto the 8" DNA Analysis Module microchip. This can create a microchip with 50 100-nL cycle sequencing sample preparation chambers for paired-end reads integrated with 100 paired-end read affinity sample cleanup chambers and separations microchannels. The servicing of the system can use microfluidics and mini-robotic on-chip functions to operate and regenerate the microchips. In embodiments comprising external automation to load samples, the Core MINDS System can produce 7 Mbases of high quality sequence per day at a substantially reduced cost in comparison to current methodologies.

Instrumentation. The base for the Core MINDS System instrumentation can be the DNA Analysis Module instrumentation. The scanner can be used without modification. The CSM microchip interface device described above can be adapted directly with minimal alterations to 1) automate the external actuation of the on-chip mini-robotics that control movement of liquids in the CSM microchip-based cartridge, 2) control the external heating and cooling for thermal cycling, and 3) drive syringe pumps to deliver cycle sequencing reagent to the chip. In some embodiments, the Tecan robot is not be needed. For 1), external actuation of on-chip valves, no equipment adaptations are needed since each actuation channel can service all of one particular valve for all channels, whether there are 2 or 400. For 2), the heating and cooling can be external to the microchip and can be either arrays of resistance heaters or strips of Peltiers. The adaptation can be achieved by designs comprising geometries with additional lengths and numbers of heaters. Heat management is be an important consideration for the system. For 3), the syringe pumps, no addition pumps are be required. The addition of service channels, described below, should allow one syringe pump to service all channels. Thus, the equipment modifications can be to combine the components of the CSM microchip interface device with the DNA Analysis Module microchip interface device.

In some embodiments, the microchip interface device and the microchip details can be designed to eliminate any spatial or temperature conflicts. The vacuum chuck can be adapted to have rings of lower temperatures for the sample preparation and cleanup chambers. The design of the combined CSM and DNA Analysis Module microchip interface devices can be greatly simplified by the concept of servicing the microchip with on-chip micro-robotics discussed below.

Figure 22:
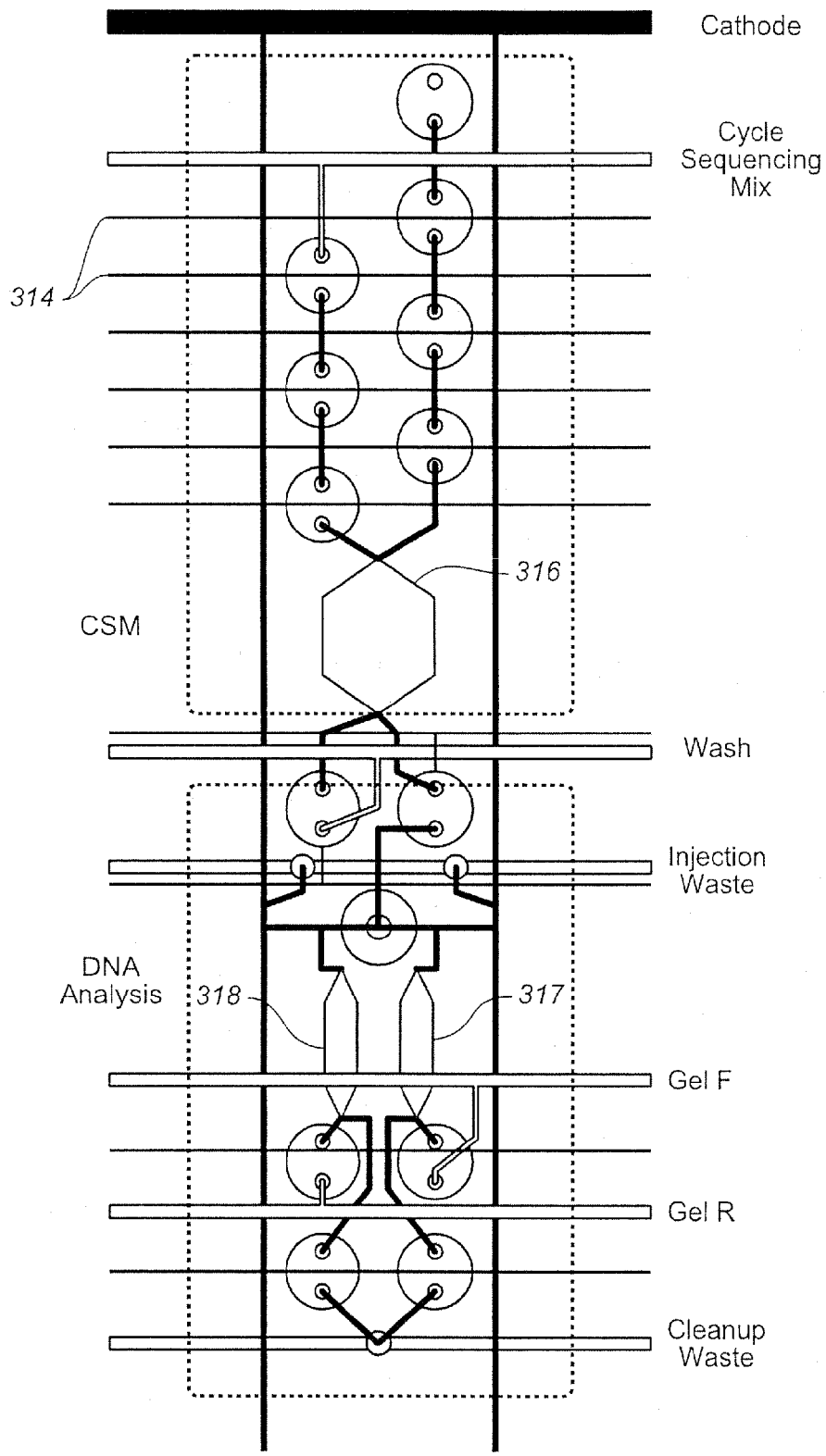
FIG. 22 illustrates an embodiments of integrated sample, preparation, cleanup, and analysis MINDS microchip repeat unit.

Microchip and Operation. The Core MINDS microchip can directly integrate the CSM microchip functionality and design, with the sample cleanup and separation from the DNA Analysis Module. FIG. 22 shows a pair of channels in one exemplary design. Note the actuation lines 314 for the valves and pumps which will be in circular rings on a microchip—these appear as horizontal lines in FIG. 22.

The samples—PCR products or beads with PCR products—can be loaded into an input reservoir. The basic CSM repeat unit (which can be repeated about 200 times) can pump the sample into the 100 nL cycle sequencing reaction chamber 316 with cycle sequencing mix, the four surrounding valves close, and cycle sequencing occurs. After cycle sequencing, as in the CSM, the cycle sequencing products and reactants can be pumped into a reservoir containing water, except this time it has an electrode connection. The sample can be electrophoresed onto two paired-read, affinity capture chambers 317-318. The contaminants can be removed and the purified fluorescently-labeled cycle sequencing fragments can be injected through twin-T injectors into two separation channels; this unit can replicated, for example, about 200 times to yield 400 separation channels. The fragments can be separated in high performance nanogels or other matrix and detected near the center by the rotary scanner. In some embodiments, an 8" with about 100 separation channels can be used to model a quarter section of a 12" wafer that can have about 400 separation channels.

The microchips can provide 45 min separation cycle times, and 45 min cycle sequencing and cleanup cycle times, one paired-read cycle sequencing reaction chamber can supply two separation channels. This simplifies the design, reduces the number of valves, electrodes, and channels that are required. The separations can be almost continuous, with only microchip regeneration and pre-run sharing the cycle time with the separation. During the 35 min separation, the sample preparation cycle can begin again with a sample loaded into the input reservoir. In some embodiments, samples can be prepared and ready for separation by the time the separation channel is ready for injection. In some embodiments, multiple cycle sequencing or genotyping chambers supplying a single separation channel as desired can be employed. The microchips, in addition to having a common central anode, also can have a common circular, open cathode channel running around the circumference of the microchip with a large buffer capacity. This channel can have extra buffer capacity to prevent ion depletion from degrading the separations, simplifies electrode number and placement, and may permit repeated matrix loadings without removal of buffer and excess matrix. The microchip also can use three dimensions to enable service channels, (i.e., cycle sequencing mix, waste, affinity gel polymers, water) to cross over other channels to greatly simplify the design and operation.

In some embodiments, the combined CSM and DNA Analysis Module microchip interface devices can rely upon servicing the microchip with on-chip mini-robotics using a three dimensional microchip design with a central wafer etched on both sides. The service channels build upon the ability of the valves to connect different layers in a multi-layer design.

Figure 12:
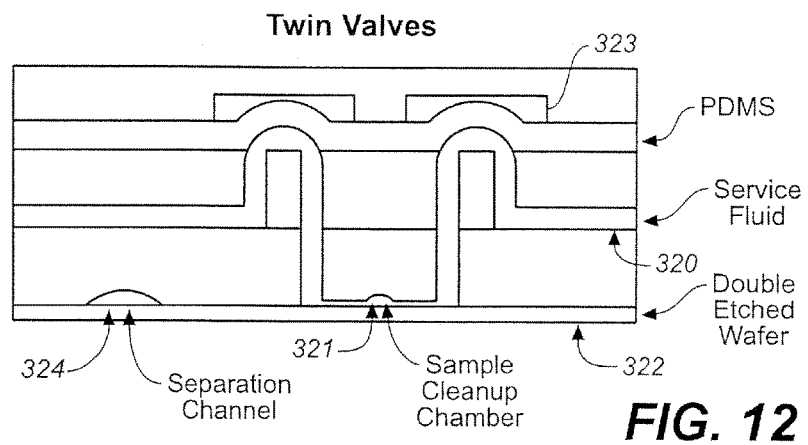
FIG. 12 illustrates an embodiment in cross-section of three dimension connection service channel supplying sample cleanup matrix.

FIG. 12 illustrates an embodiment of the connection of a service channel 320 providing fresh affinity capture matrix to a sample cleanup chamber 321. In the design shown, the service channel fluid path enters from the left on top of the etched wafer 322, crosses over a separation channel, and goes up in one aperture of a valve 323 on the PDMS layer, over, and then down the second aperture of the valve to the bottom layer of doubly etched wafer, where the sample preparation, cleanup, and separation channels 321, 324 are etched. The service channel fluid path then passes through the affinity capture sample cleanup chamber (which runs perpendicular to the plane of the figure) and through a valve to remerge on the top of the etched microchip. This allows the service channel on the upper side of the microchip to cross sample separation and other channels by passing above them without interference. This same principle can be applied to sample preparation channels, but not analysis channels. Individual service channels, which can be wide and deep, will deliver cycle sequencing mix, refill the two affinity capture matrices into two sample cleanup chambers, provide wash to restore the sample preparation chamber, and collect waste from all the sample preparation, sample cleanup, and separation channels. The six service channels will each form concentric rings on the microchip. They will be connected to syringe pumps, macroscale fluidic, or vacuum lines. The "extra" wafer layer between the doubly etched wafer and the PDMS will contain only through holes. Since the etched channels are on both sides of the etched wafer; the through holes can be relatively large except for the cycle sequencing mixture.

The regeneration of the microchip can be performed as follows. After the separation, the central umbilical cord can push new matrix into the channels, just filling the separation channel. Differential channel widths on the side channels can direct the matrix towards the cathode. In some embodiments, the two sample cleanup chambers can be regenerated using two service channels. The service channels can be closed by the valves normally. To replace the affinity matrix, the valves can be opened, the syringe pump for the channel activated, and new affinity matrix pumped into all the forward chambers, for example (multiple runs may be possible per loading of affinity matrix). A similar sequence occurs for the other affinity chamber. The cycle sequencing reaction chamber can be similarly cleaned by pumping a wash solution from the wash service line through the chamber and into the waste reservoir. The buffer reservoirs can be connected to a large common reservoir above the topmost wafer. The larger volume can minimize the impact of evaporation and buffer depletion, and simplify buffer filling and flushing.

Aspects of the present disclosure may be further understood in light of the following examples, which should not be construed as limiting the scope of the present disclosure in any way.

EXAMPLES

1. Bead-Based Capture of *E. coli*

The capture of model target organisms from dilute solutions with monoclonal or polyclonal antibodies conjugated to magnetic beads can be used to provide concentrated, purified material for introduction into BPM microdevices. Here, we describe the use of DYNAL® beads with conjugated antibodies against *E. coli* strain O157. We have run three series of experiments: (1) capturing *E. coli* from diluted stocks, (2) capturing *E. coli* in the presence of large excesses of *Bacillus*, and (3) capturing *E. coli* from an aerosol sample from a Baltimore Air-Sampler.

We first compared the DYNAL® "swab protocol," which is used for detecting *E. coli* O157 in food samples, with direct plating of beads onto a suitable growth medium. We found that direct plating of the non-pathogenic strain O157 and *E. coli*? ATCC strain 700728 onto trypticase soy agar (TSA) yielded about five-fold more colonies and therefore provided a better estimate of the number of captured organisms than the swab method. Therefore, we used direct plating in all subsequent experiments.

We measured the ability of DYNAL® beads to bind *E. coli* across a range of cell titers from $10^5$ CFU/mL to $10^1$ CFU/mL in PBS/Tween buffer. In these and subsequent immunomagnetic separations (IMS) experiments, the protocol was to add a 5 μL suspension of DYNAL® beads to the suitable dilution of *E. coli* in 250 μL PBS/Tween. The cells with added beads were mixed in a capped plastic microfuge tube for ten min on a rocking platform. The beads were then captured against the side of the tube with a strong magnet, the supernatant removed (but saved for plating), and the beads were washed three times with PBS/Tween buffer. The beads were resuspended and dilutions of the beads were plated. In several experiments we also plated out the washes. In general, the washes contained few target organisms; the target cells were either captured on beads or were not bound and recoverable in the primary supernatant.

Figure 35:
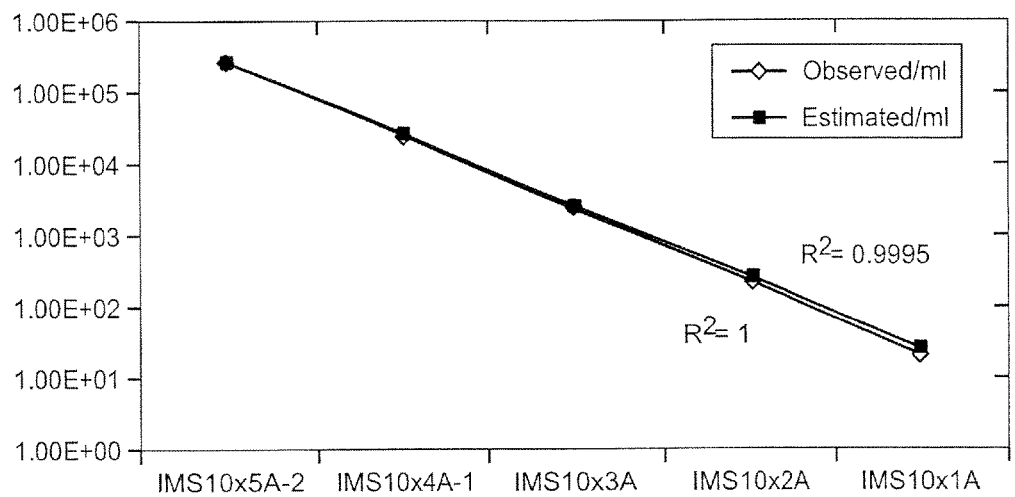
FIG. 35 shows capture of $E.$ $coli$ by beads over a range of concentrations.

FIG. 35 shows the result of capturing *E. coli* O157 diluted in PBS/Tween when the capture was performed in triplicate for starting concentrations of bacteria of $2 \times 10^5$, $10^4$, $10^3$, $10^2$, 20, and 2 cells/mL. The observed number of captured cells was linear ($R^2 = 0.995$) over the range from $10^5$ to 10 cells/mL with an efficiency of capture of approximately over 95% for the range $10^5$ to $10^3$ cells/mL, dropping to 87% for 100 cells/ml and 69% for 20 cells/mL. Other experiments (data not shown) generally yielded recoveries of greater than 85% from PBS/Tween for the *E. coli* concentrations of $10^3$-$10^5$.

2. Dynamic Range of Capturing of *E. coli* Using Monoclonal Antibodies

Figure 36:
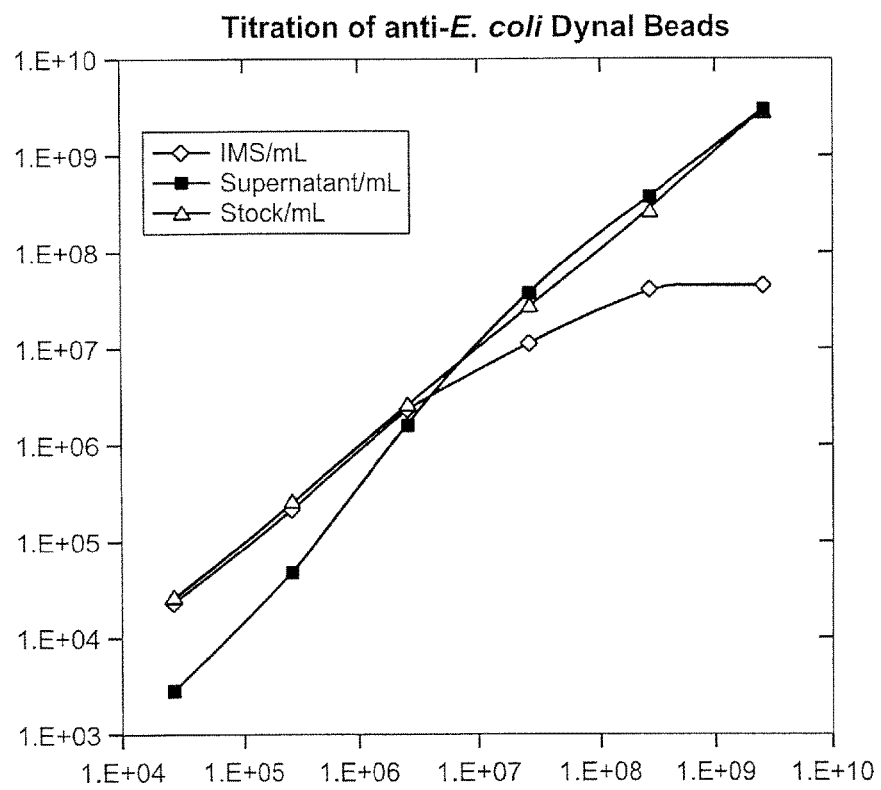
FIG. 36 shows the titration of monoclonal antibodies coupled to DYNAL™1 beads in the immunocapture of $E.$ $coli$.

The capture chemistry was studied first in 250 μL volumes in tubes, and the capture and washing optimized using model organisms dispersed in buffers. FIG. 36 shows a representative capture of *E. coli* using monoclonal antibodies coupled to DYNAL® beads. *E. coli* O157 was added to 5 μL of beads coupled with anti-*E. coli* O157 antibody in 250 μL PBS/Tween at various concentrations. The mixture was mixed on a rotating mixer for 10 min. The beads were pulled to the side of the tube using a strong magnet and the supernatant removed. The beads were washed three times with 250 μL PBS/Tween (PBST). The washed beads were resuspended in 250 μL PBST and captured *E. coli* was enumerated on TSA.

The results shown in FIG. 36 demonstrates that a dose response is found between the amount of beads and its ability to capture *E. coli*. FIG. 36 shows that the capture is linear up to about $10^6$ cells/mL, and saturates at a maximum of about $4\times10^7$ cells/mL. Above $10^6$ cells/mL an increasing percentage of the cells are recovered in the supernatant. Direct microscopic examination of DYNAL® beads saturated with *E. coli* revealed approximately 5 cells/bead. This capture method has demonstrated the ability to purify and concentrate an average of over 90% of target cells contained in 250 μL down to a volume of less than 10 μl in less than 15 min.

3. Specificity Capturing of *E. coli* Using Monoclonal Antibodies

To determine the specificity of bead based capture, we tested the impact of added *Bacillus cereus* (ATCC 11778) cells on the binding of *E. coli* to antibody-coated beads under standard assay conditions. A suspension of approximately $10^4$ *E. coli*/mL was mixed with varying titers of *B. cereus* and IMS were performed as described above, except that recovery was on TSA media with tetrazolium added at levels that selectively inhibited *B. cereus*. This allowed direct plating of the cell mixtures, but only *E. coli* could replicate and thus be quantified as colony forming units (CFU).

Figure 37:
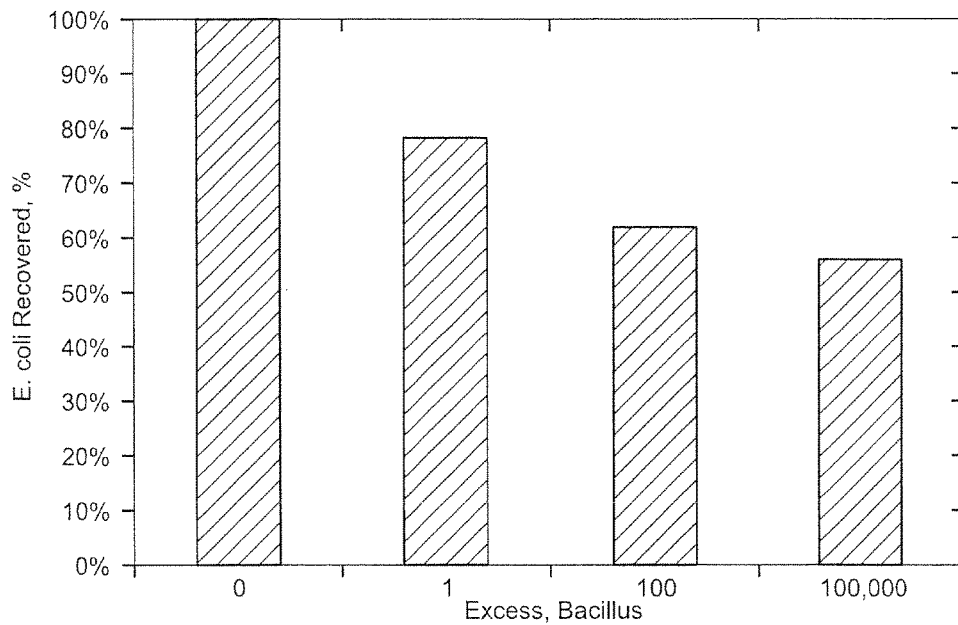
FIG. 37 shows the affect of $B.$ $cereus$ on immunocapture of $E.$ $coli$.

As shown in FIG. 37, *B. cereus* addition decreased the amount of *E. coli* bound to the beads—by about 20% when the two microbes were present at a 1/1 ratio, but a 100,000-fold excess of *Bacillus* only decreased *E. coli* binding to 56% of the control. This suggests for this antibody-cell combination the DYNAL® beads can yield excellent specificity.

4. Capturing *E. coli* from an Aerosol Sample Using Monoclonal Antibodies

Having shown that we can efficiently capture, purify, and recover bacterial cells, we wanted to extend this to recovering *E. coli* O157 from solutions containing 90% (v/v) of a Baltimore Air Sampler-derived Liquid (BASL) sample courtesy of Spector Industries. The BASL contains tremendous diversity of competing microorganisms, pollen, and other chemical and biological substances that could potentially interfere with the antibody-mediated binding and recovery.

To test our ability to concentrate and recover *E. coli* O157 from BASL solutions, we grew the strain in pure culture and prepared titers of $10^2$, $10^3$, and $10^4$ CFU/mL in 90% BASL and also PBST as a control. A 5 μL suspension of DYNAL® beads (containing anti-O157 antibody) was added to a 250 μL sample containing *E. coli* in either 90% BASL or PBST, incubated for ten minutes on a rocking platform, and followed by bead capture. The supernatant was removed, the beads washed three times with PBST, and resuspended in PBST. The primary supernatant and the beads were plated out for determination the number of CFU. All plate counts were determined using MacConkey-Sorbitol agar with added Cefixime and Tellurite (CT-SMAC). CT-SMAC is a semi-selective medium for *E. coli* O157, which served to reduce the overall number of non-*E. coli* CFU from the large number of organisms contained in the BASL and provides a colorimetric indication of O157 by fermentation of the sorbitol.

Figure 38:
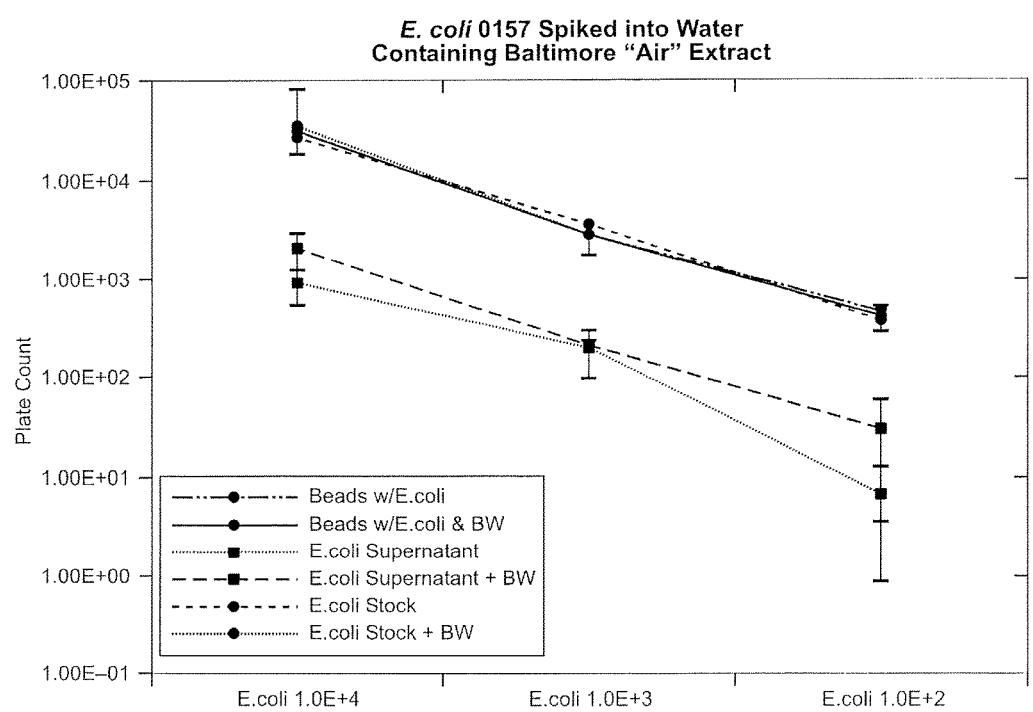
FIG. 38 shows the recovery of $E.$ $coli$ by immunocapture from spike air sampler liquid.

Excellent binding and recovery of *E. coli* O157 was obtained using our standard IMS protocol from solutions containing 90% BASL (FIG. 38). In general, greater than 90% of the cells were bound to the IMS beads and recovered regardless of whether the cells were dispersed in PBST or 90% BASL. This was true across the range of cell concentrations tested from $10^4$, $10^3$, and $10^2$ CFU/ml.

Figure 39:
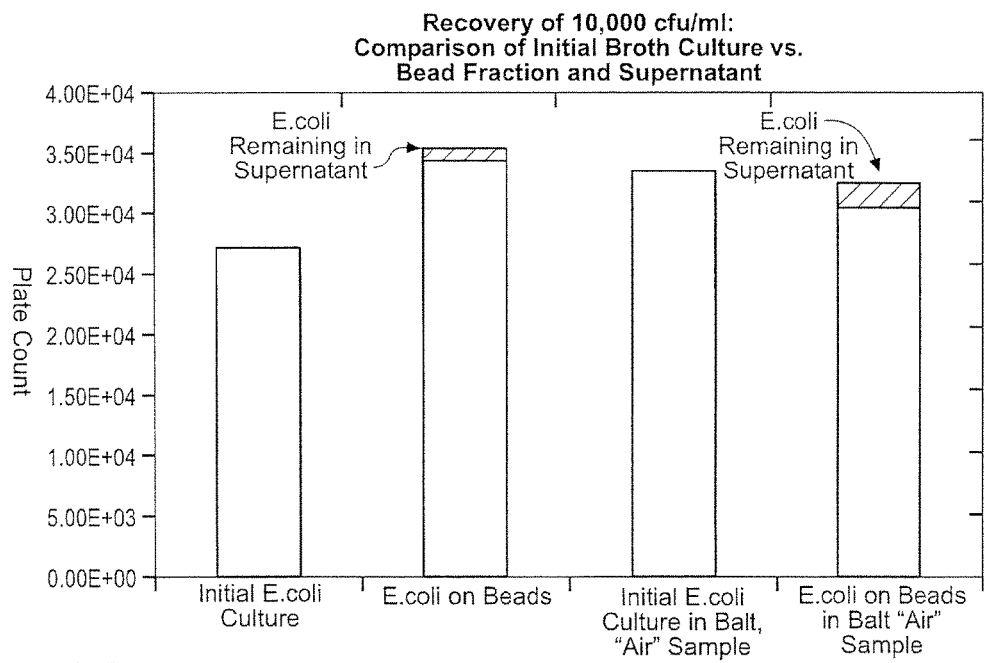
FIG. 39 shows the data set specifically for the $10^4$ CFU/ml titer of FIG. 38.

FIG. 39 shows the data set specifically for the $10^4$ CFR/ml titer. The first bar and third bars show the titer of the controls. The second bar shows the proportion of cells recovered in the bead fraction and supernatant fraction when the samples were performed exclusively in PBST as a control. The fourth bar shows the proportion of cells recovered in the bead fraction and supernatant fraction when the experiment was performed exclusively in 90% BASL. This experiment indicates components in the BASL do not interfere with binding and recovery at least for this antibody and its epitope.

5. Solid Phase Extraction (SPE)

We evaluated SPE for an off-chip disposable flowthrough device that can process up to liter sample volumes, binding analytes onto a small surface while allowing interfering compounds to flowthrough. Ultimately, the target analyte can be recovered in a concentrated form for down stream processing by a microchip-based bioprocessor or the SPE material itself can be the feedstock for the microchip.

We evaluated silica matrix SPE capture of *E. coli*. The basic scheme was to run bacteria of different titers through the solid phase, elute with a small volume back-flush, then analyze supernatant and eluent for bacterial content. In the following experiments, the DH5α strain of *E. coli* (Invitrogen Technologies) was prepared at dilutions ranging from $10^4$-$10^2$ cells/mL in PBS/Tween (PBST). A bare silica Extract-Clean SPE cartridge (Alltech Associates) having a 100 mg solid bed was used in all experiments.

For each cartridge: (1) 18 mL of a bacteria/enzyme mixture was run through an SPE bed at a flow rate of approximately 5 mL/min; (2) supernatant was collected and analyzed for bacterial titer; (3) the cartridge was back-flushed with 2 mL of buffer and eluent was the number of bacteria was determined Analysis was performed by bacterial growth at 37° C. on TSA as above to determine the relative capture and recovery of bacteria.

6. Retention of Bacteria by SPE Media in a Flowthrough Mode

Figure 40:
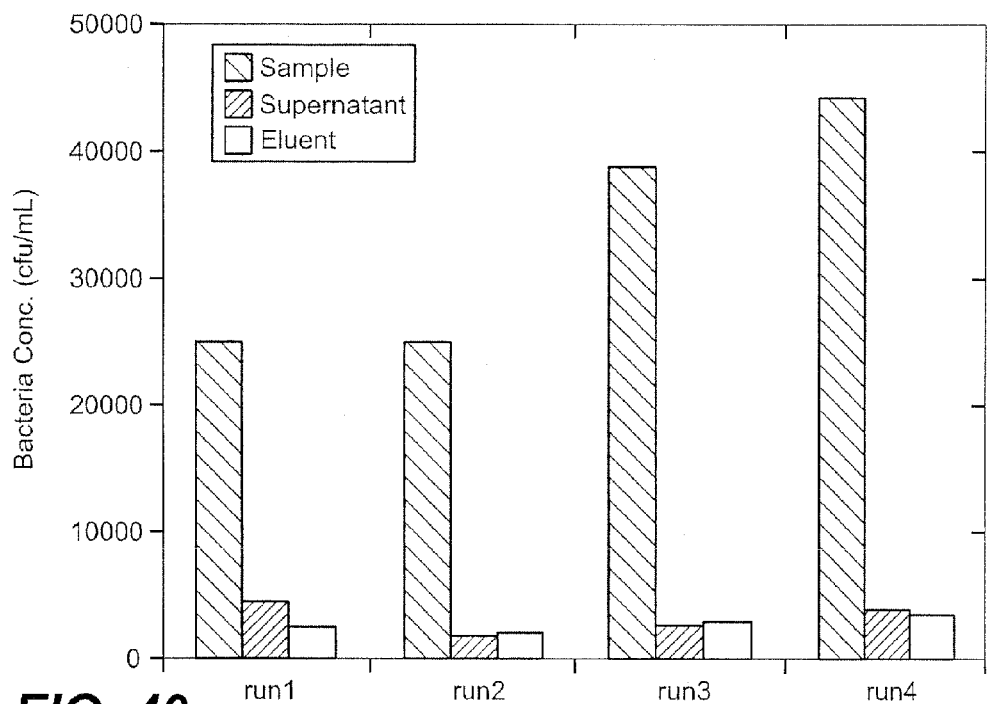
FIG. 40 shows the results of concentrating high titered $E.$ $coli$ for various fractions of sample run through a 100 mg bed of silica Extract-Clean SPE media.
Figure 41:
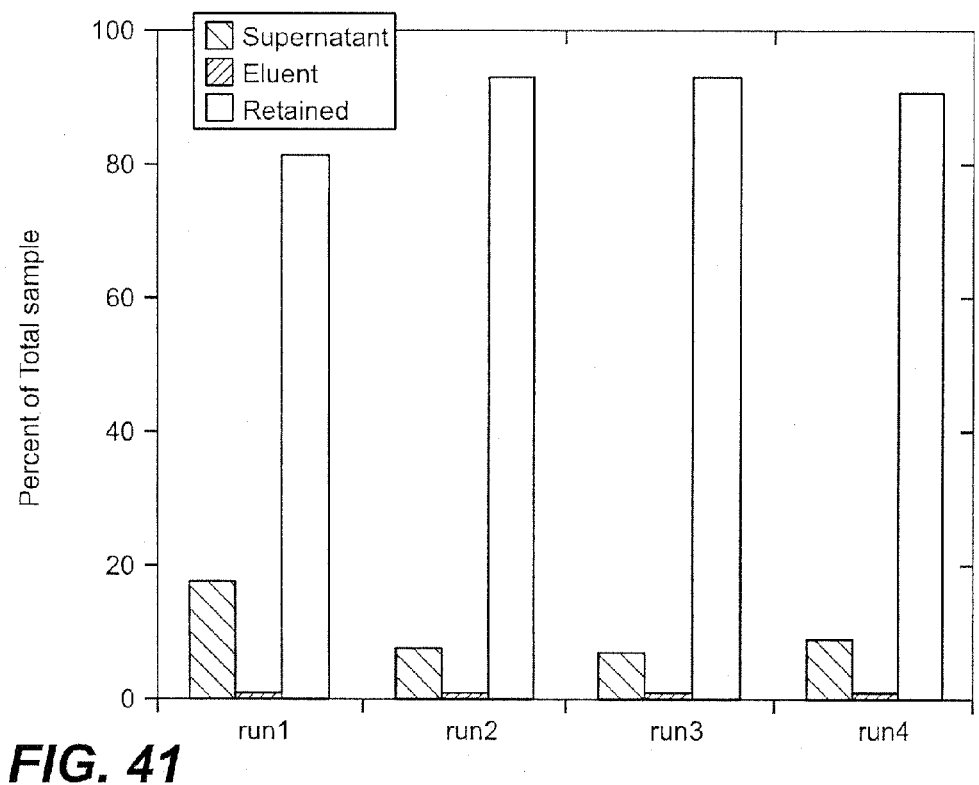
FIG. 41 shows the percentage of total bacteria from high concentration $E.$ $coli$ samples present in various fractions after run through a 100 mg bed of silica Extract-Clean SPE media.

FIG. 40 shows the results of the bacterial assays as a function of bacterial concentration in the sample loaded, and in the post-SPE supernatant (unbound) and eluent with samples with relatively high bacterial concentration of 25,000 or 45,000 CFU/mL. In this range, 80 to 90% of the *E. coli* are retained on the SPE matrix (FIG. 41), while a small amount of the bacteria pass though, and a very small amount (1%) is recovered by a backwash. Thus, a strong binding is exhibited on silica, with poor elution of viable cells. At very low titers, 125 and 250 CFU/mL, proportionately more cells pass through the column, with only about 20% retained (data not shown).

7. Retention of Protein (β-galactosidase) by SPE and Agarose "Big Beads" Media in a Flowthrough Mode Some embodiments employ agarose-based "Big Beads" to capture or purify biomaterials. Commercially-available β-galactosidase (Sigma) was dissolved in 0.1 M phosphate buffer, pH 7.5, 1 mM $MgCl_2$ at two concentrations: 100 and 10 ng/ml. These two solutions were run through "Extract Clean" SPE cartridges (Alltech) containing a 100 mg of 50 μm silica particles with 50 Å pore size, or 5 ml "Big-Bead" columns with 500 μm hardened agarose beads. For both agarose and silica-derived media, enzyme solutions (20 ml) were run through their respective SPE bed at a flow rate of approximately 5 mL/min, the supernatant was collected, and the cartridge was back-flushed with 2 mL of buffer at a flow rate of approximately 1 ml/second. Supernatant and eluant were analyzed for enzyme activity using o-nitrophenyl-β-galactoside (ONPG) as the substrate.

Figure 42:
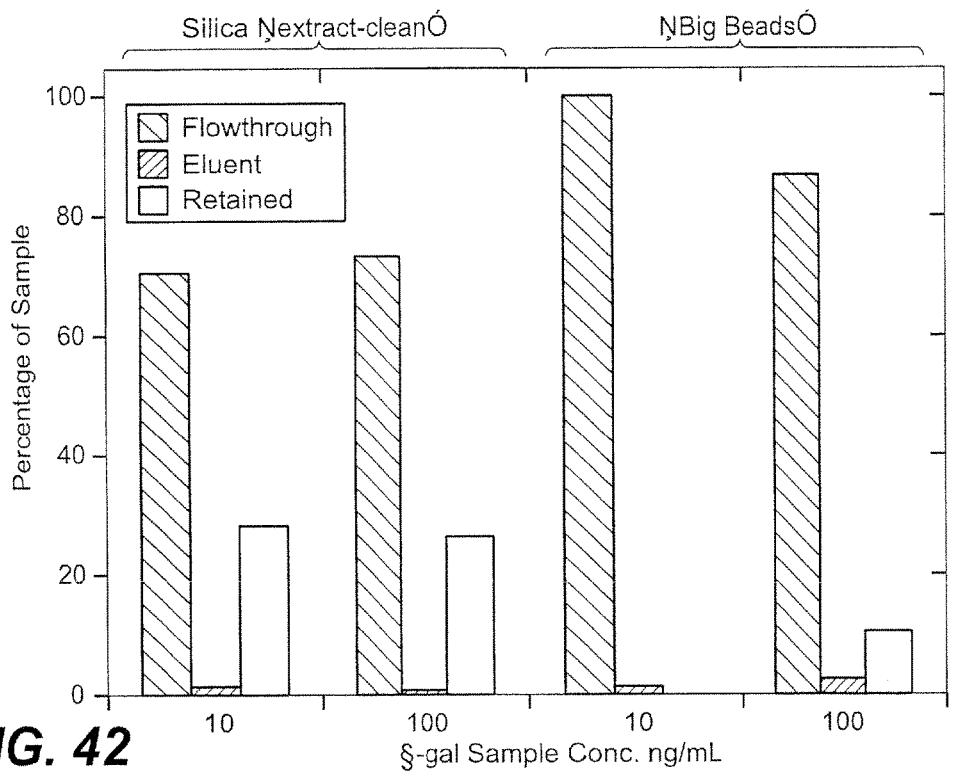
FIG. 42 shows the recovery of β-galactosidase using silica beads (left) and Big Beads (rights).

FIG. 42 shows a graph of the distribution of β-galactosidase activity in the "supernatant", "eluant", and "retained" fractions for the two matrices at both the 10 and 100 ng/ml enzyme concentrations. "Retained" is calculated by the difference among loaded, flowthrough, and eluant. For the silica-based SPE media, approximately 75% of the β-galactosidase is flowthrough and recovered in the supernatant. Very little enzyme (1-2%) is detected in the back-flushed eluant. Therefore, approximately 25% of the β-galactosidase is retained on the column. For the "Big-Bead" medium, 85-99% of the β-galactosidase flows through the column, while less than 5% is recovered in the eluant (FIG. 42). This means that a very low amount, about 0-10%, is retained on the matrix. Therefore, these media may be useful in the flowthrough mode to separate target analytes, such as toxins, from retained materials.

Figure 43:
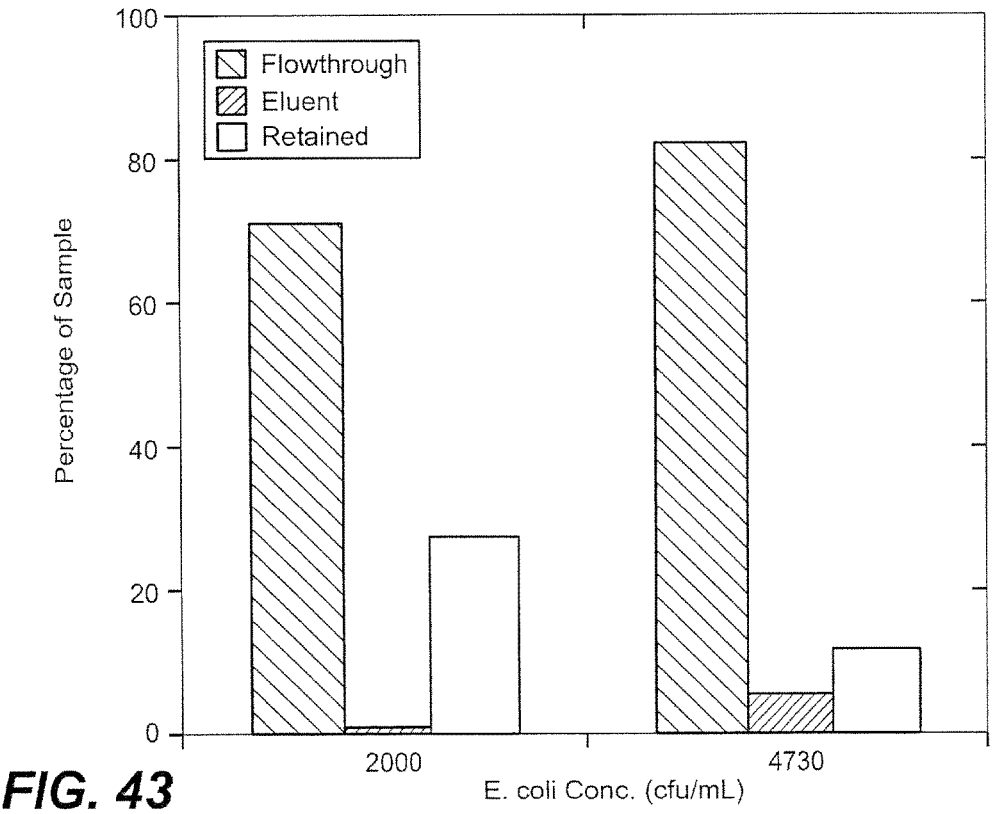
FIG. 43 shows the recovery of $E.$ $coli$ using Big Beads.

8. Retention of *E. coli* by Agarose "Big Beads" as a Capture Media in a Flowthrough Mode We evaluated the ability of the agarose Big Bead cartridges to selectively bind and concentrate *E. coli* strain DH5α. FIG. 43 shows the distribution of *E. coli* DH5α in fractions obtained from the Big Bead capture experiment performed at initial cell concentrations of 2,000 or 4,700 CFU/ml. These experiments were performed in 0.1 M phosphate buffer, pH 7.5, 1 mM $MgCl_2$ using 20 mL of a bacterial suspension at $10^4$ or $10^3$ CFU/mL. The assay was growth on TSA plates. At the lower titer (2,000 CFU/ml), >70% of the bacteria were recovered in the flowthrough fraction and less than 1% in the back-flushed eluant. At the higher titer (4,730 CFU/ml), >80% of the bacteria were recovered in the flowthrough fraction and less than 5% in the eluant. Thus only 25-10% of the bacteria remained bound to the Big Bead matrix.

9. NanoBioProcessor Microchips

Microfibrication of microfluidic devices was performed essentially was described by Liu et al. 2000. *Proc. Nati. Acad. Sci. USA* 97(10):5369-5374. Briefly, Borofloat glass wafers were cleaned and an amorphous silicon mask deposited followed by an adhesion layer of HMDS and a layer of photoresist. The photoresist was patterned with UV light through a mask and the channel pattern chemically etched with concentrated HF, typically to depths of 40 µm for the channels on the fluidic wafer and 70 µm deep for the manifold wafers. The photoresist and amorphous silicon were stripped off and access holes were drilled using a CNC-minimill with diamond drills. These holes can be used in a four layer microchip as reaction and detection chambers. Alternatively, we will use ultrasonic drilling to drill all holes simultaneously. After cleaning, the fluidic wafer and via wafers were aligned and thermally bonded. The manifold wafer and PDMS membrane were added to create four-layer microchips.

Two NanoBioProcessor microchips were designed and built. The first microchip, MBI-11 240 (FIGS. 19A-19D), was designed to isolate and test essential microfluidic processing on-chip components at a variety of scales. It demonstrates embodiments of (1) valve design, (2) reaction chamber design, (3) ganging reactions, and (4) router design. The operation of each element is controlled by an eight channel, full-scale pneumatic system 241 to operate the valves, pumps, and routers. We have tested the operation of the MOV valves, pumps, and routers in 3-layer and 4-layer chips. Each element of the chip is designed to interface with an 8-channel full-scale pneumatic bus to facilitate valve operation.

Figure 20:
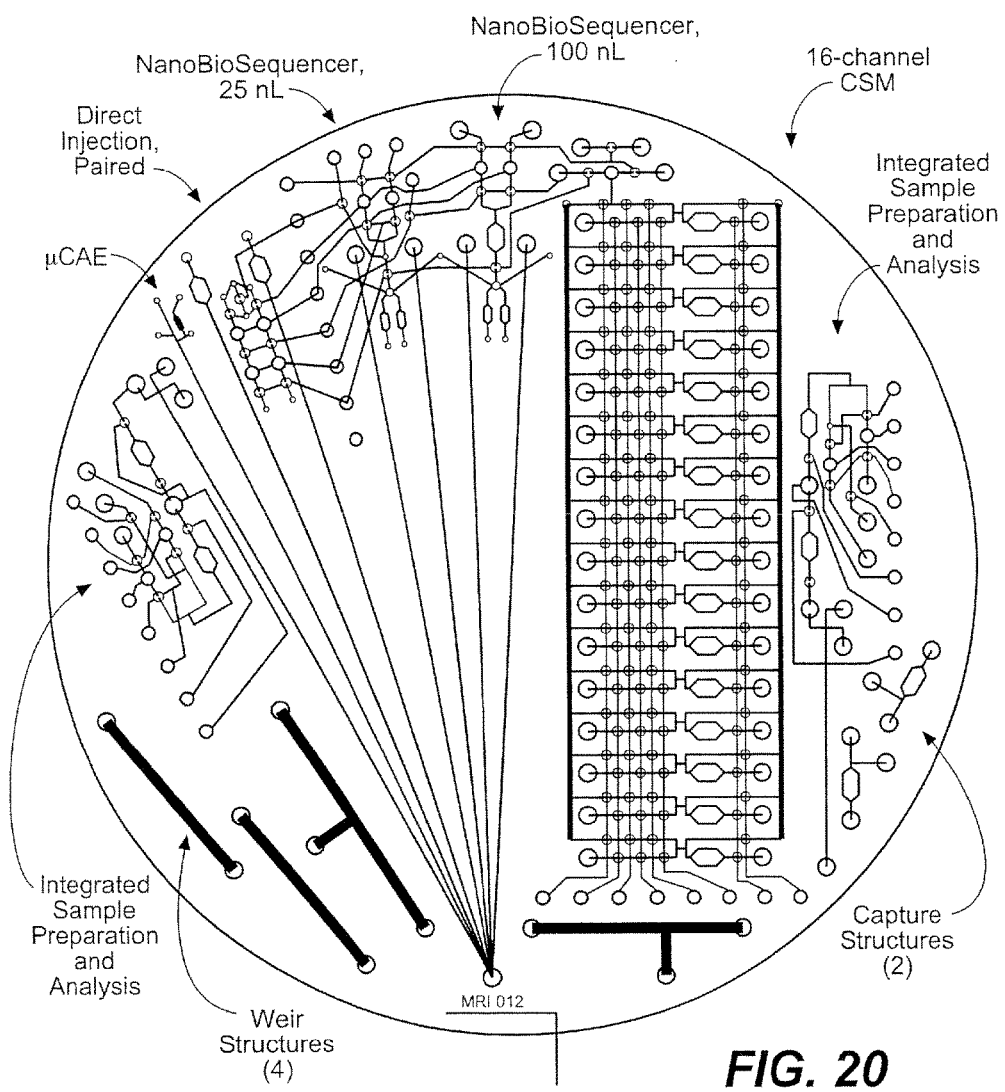
FIG. 20 illustrates microchip embodiment MBI-12 with nanofluidic structures for microcapillary electrophoresis (μCAE) integrated with sample preparation. Fluidic channels are shown in blue and MOV actuation channels in red.

The second NanoBioProcessor microchip, MBI-12, was developed to test both sample preparation from beads for cycle sequencing or PCR and to test µCAE, both separately and coupled with sample preparation. The mask design, shown in FIG. 20, was etched, assembled into functional four layer microchips, and is being tested. MBI-12 has several designs of µCAE channels and how to connect them to upstream sample preparation devices.

We have demonstrated mixing using MOV valves, pumps, and routers and using Surface Acoustic Wave (SAW) mixing which works well in deep chambers such as the via. SAW creates a pulsating internal pressure wave within a chamber in the microchip and homogenizes solutions to mix them.

While mixing micro and/or nanoscale volumes can be difficult to accomplish and typically can be limited by diffusion, the MOV valves, pumps, and routers, disclosed herein, enhance mixing and can substantially reduce the time to mix solutions. In various exemplary embodiments, one or more valves, pumps, and/routers disclosed herein can be arranged in various geometries or formats to facilitate mixing of two or more liquids either sequentially or substantially simultaneously. The rate and degree of mixing can be selected at the discretion of the practitioner. In various exemplary embodiments, mixing can occur rapidly and/or can be substantially complete. The skilled artisan will appreciate that the rate and degree of mixing can depend on the number and types of fluids, the volumes, and miscibility. Selecting the desired rate and degree of mixing is within the abilities of the skilled artisan. in various exemplary embodiments, mixing can be effected when MOV valves and/or pumps are used as routers or in a "T" mixer. In some embodiments, solutions can be mixed by a back and forth motion of the fluid through a router or a "T" structure drive by two or more pumps.

10. NanoBioProcessor Performing Sample Preparation for Biodefense

This bioprocessor module receive samples from an upstream air sample collector or other input device, create aliquots for archiving and retesting, lyse samples, prepare and label samples, and output them to a single molecule fluorescence correlation detector for analysis. The bioprocessor module includes disposable plastic cartridges that contain the fluidics and an instrument that operates the cartridges.

Prior to analysis the sample is partitioned and divided into aliquots. The automated microfluidics processor can: 1) prepare nucleic acids for testing; 2) prepare protein for testing; 3) prepare cells for detection; 4) archive for retesting of positive samples and forensic analysis.

The cartridges are in a "CD" format and have 12 bioprocessor units per cartridge in sectors, with each unit used for a single sample. The cartridge processes one sample in a bioprocessor unit and then rotates to receive the next sample in the next bioprocessor unit. For a 2 hr sampling regime, the cartridges is automatically changed daily from sets of cartridges stored in mini-carousels, analogous to a CD changer. Manual intervention to resupply cartridges and reagents is performed about once every two weeks.

The instrument provides the mechanics to store, load reagents, run, and change cartridges. The instrument has functionality to 1) open and close solenoids to deliver pressure or vacuum to operate the valves and pumps, 2) heat and cool areas of the cartridge, 3) move cartridges to and from mini-carousels, 4) ultrasonic disrupt microorganisms, and 5) other functions, as needed.

11. NanoBioProcessor Performing Genetic Analysis for Biodefense

Sample Concentration Module. Starting at the macroscale, magnetic beads modified with antibodies to the surface epitopes of target organisms are added to milliliter volumes of air collector 210 effluents (or slurries produced from other matrices) in a chamber (FIG. 8). The beads are mixtures of sets of beads coated with antibodies specific to individual organisms, subtypes, species, etc. The range of organisms interrogated can be extended with additional reagent mixtures. The beads capture the target organisms while contaminants are removed by washing—providing a first dimension of selectivity and specificity. The beads containing target organisms are collected by a magnet in an SCPM 211.

Sample Amplification and Analysis Module. Now entering the microscale, the beads are loaded into a reservoir 212 containing lysis buffer on the NanoBioProcessor (NBP) microchip 213 with all further manipulations occurring at the microfluidic scale. The NBP microchip 200 (FIG. 18) is designed to process samples in individual bioprocessor units using microfluidic on-chip valves and pumps as control elements. The beads are pumped from the reservoir 221 until they are trapped by a weir 222 where they are sonicated to disrupt spores and/or cells and release DNA. The DNA is moved to a reaction chamber 223 where PCR reagents with specific primers containing probes for µRT-PCR are added by the on-chip pumps and µRT-PCR performed in multiplexed reactions—providing a second biochemical dimension of selectivity and specificity.

Figure 18:
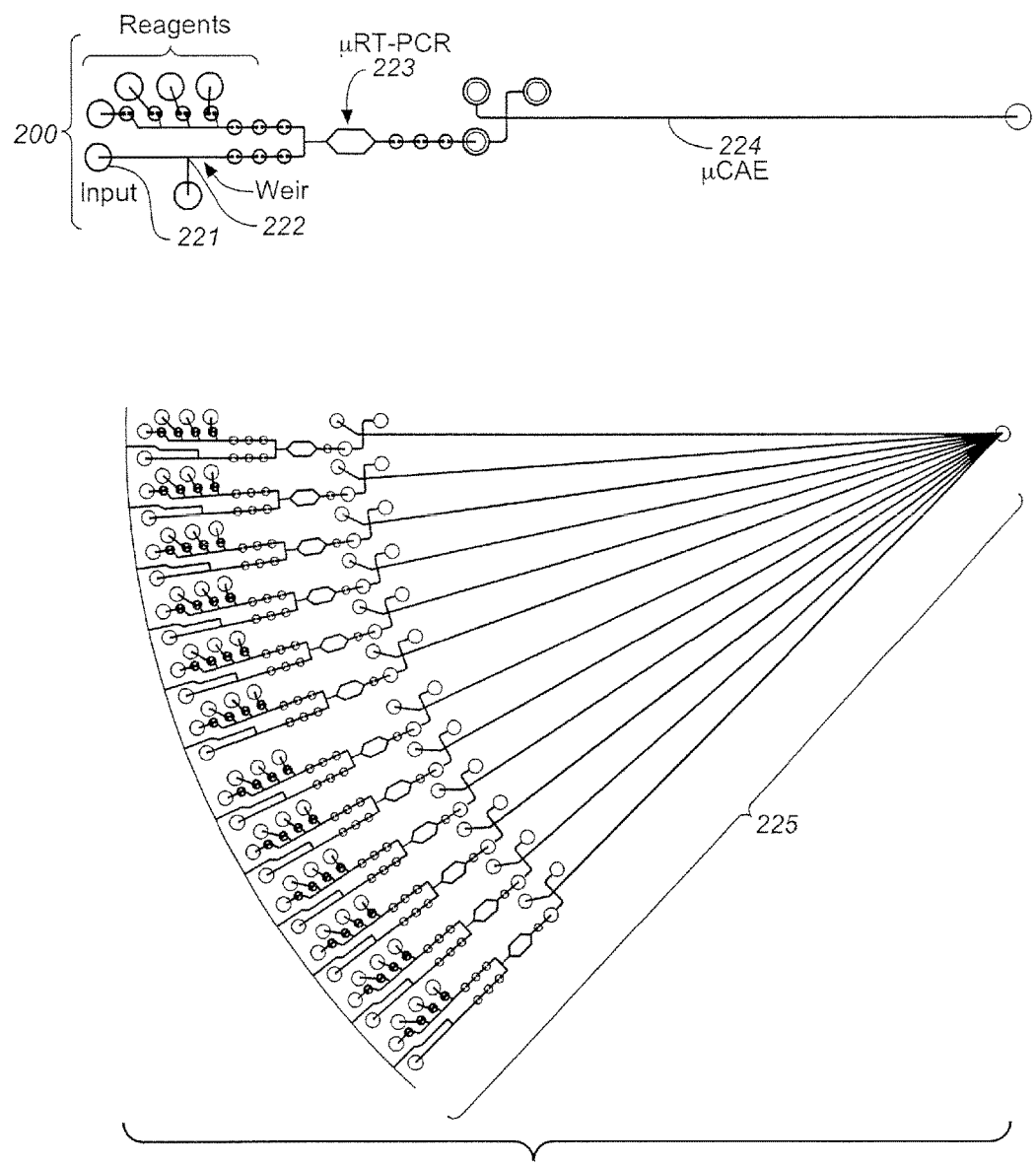
FIG. 18 illustrates an embodiment of a nonbioprocessor unit and microchip layout.
Figure 19A:
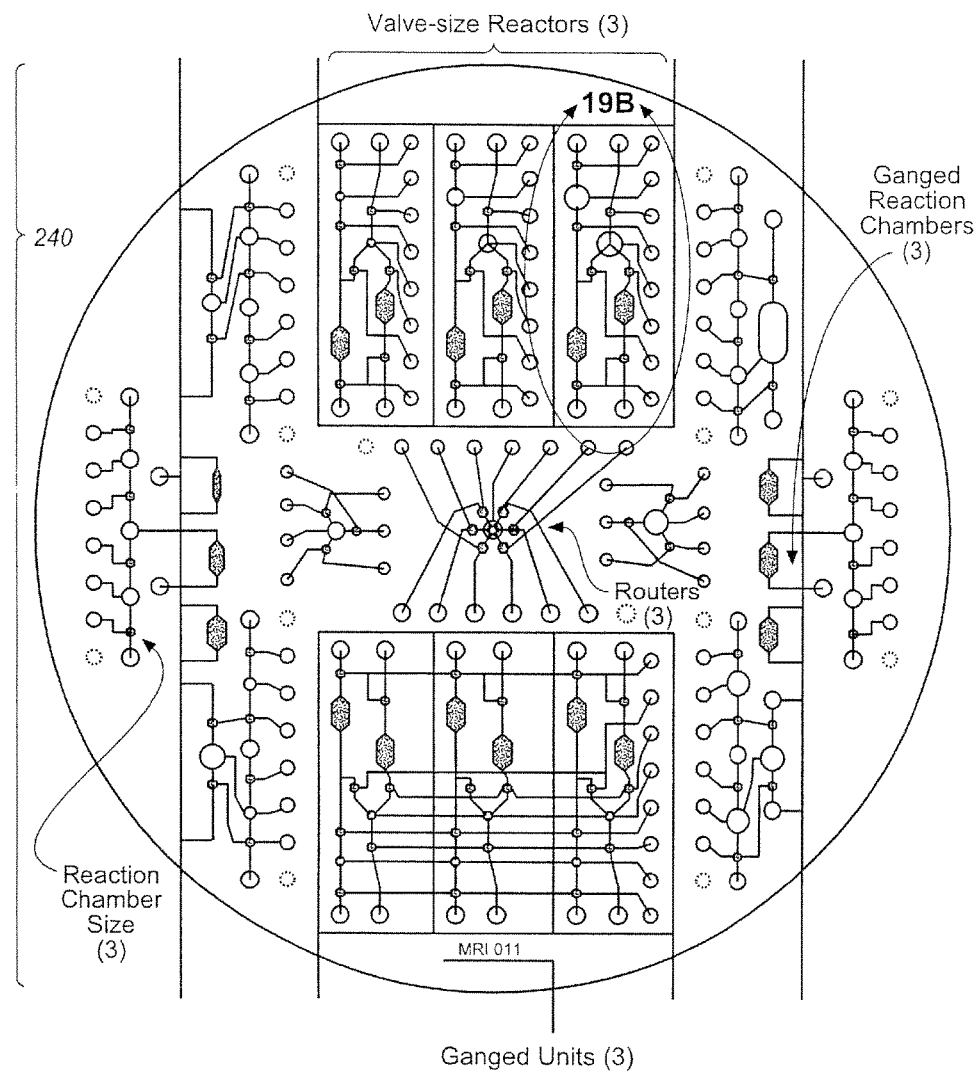
FIGS. 19A-19D illustrates microchip embodiment MBI-11.
Figure 19B:
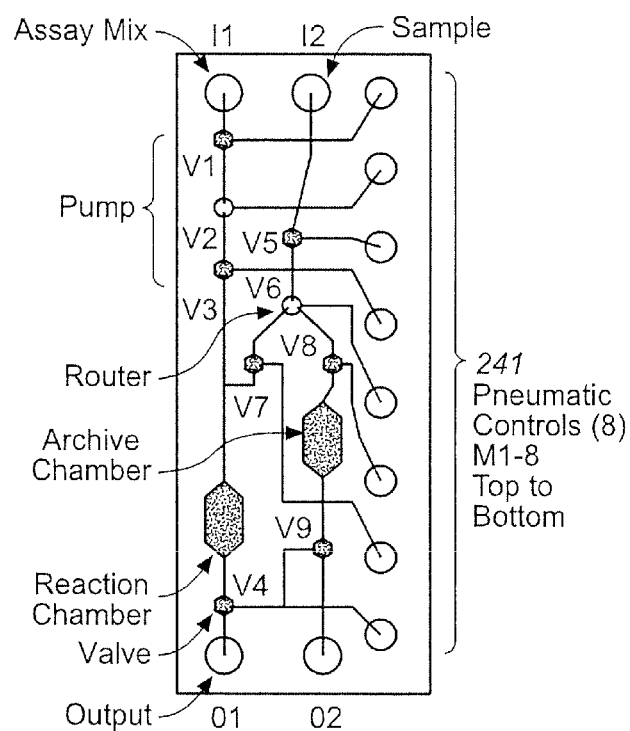
Figure 19C:
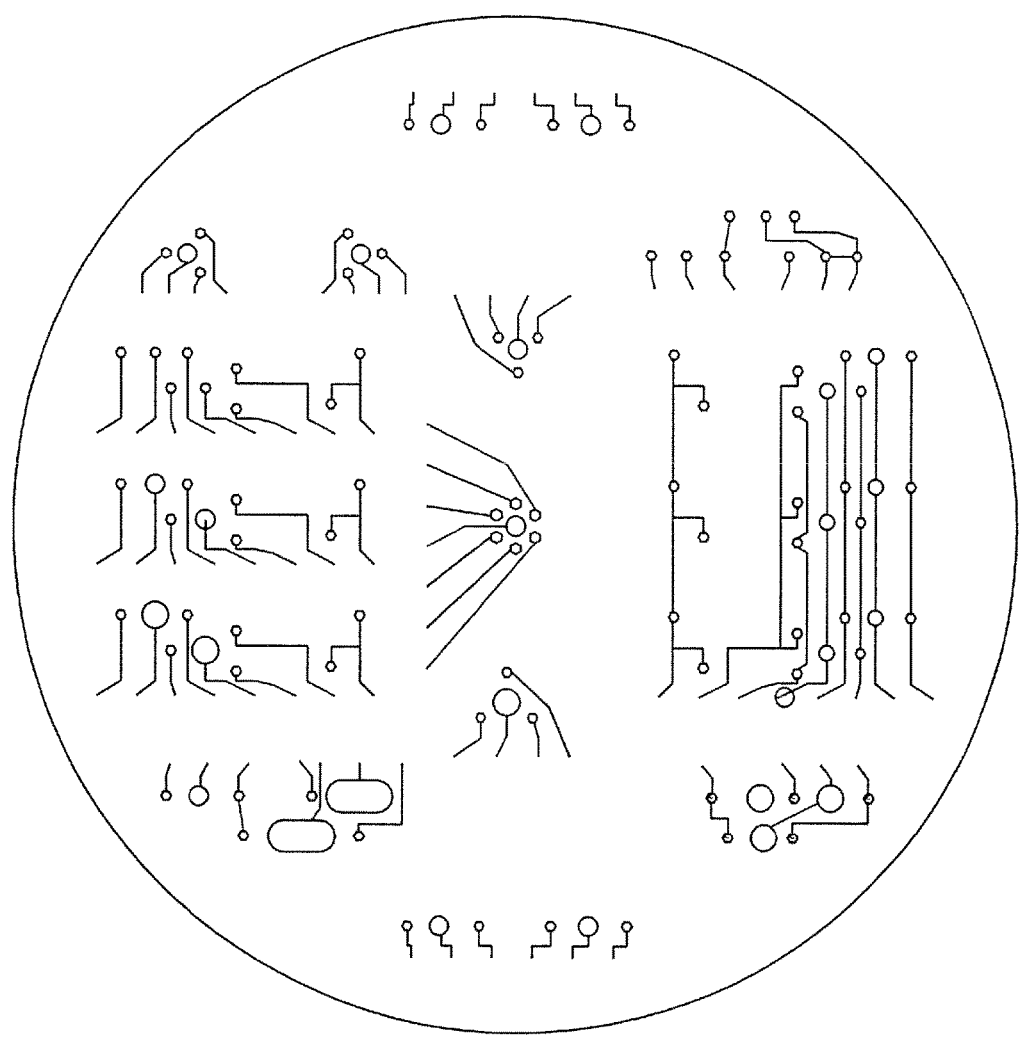
Figure 19D:
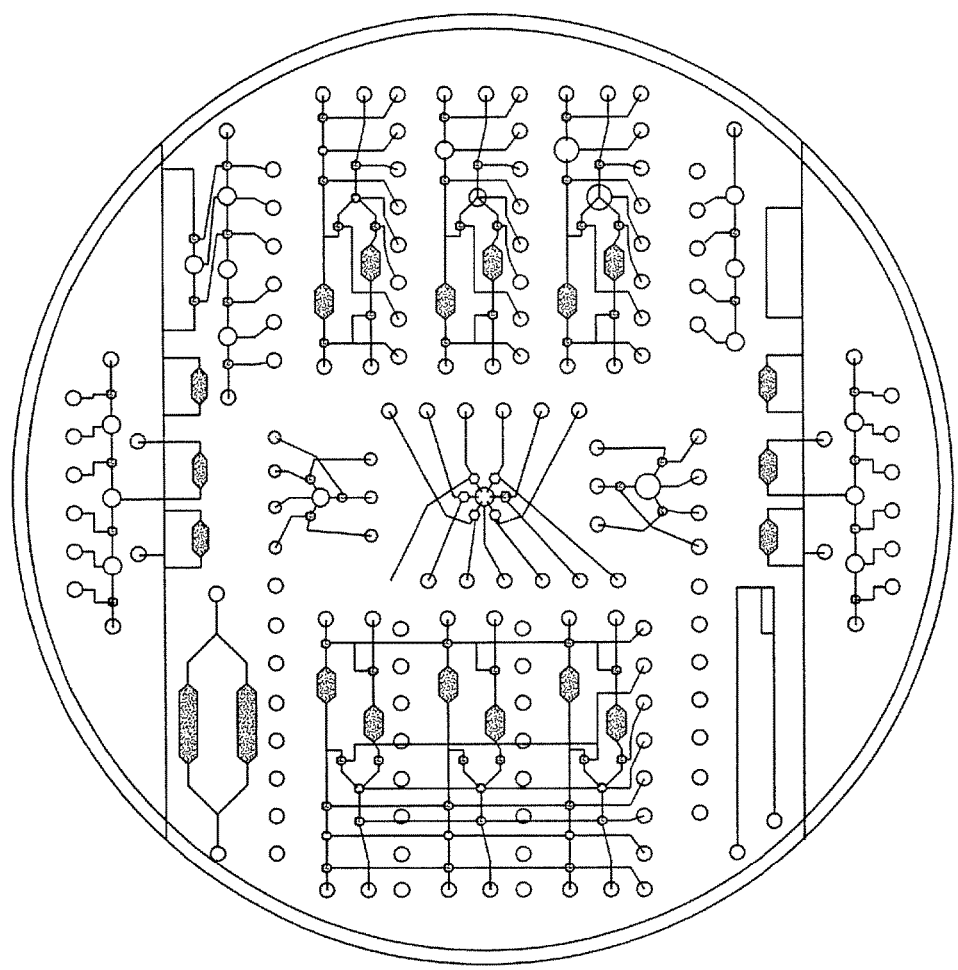

While RT-PCR is a powerful molecular diagnostic tool, RT-PCR suffers from high and variable background as fluors are unquenched by nucleases, non-specific extension, or other mechanisms. To minimize false positives, putatively positive µRT-PCR samples are separated by fast (<5 min) on-chip microchannel capillary array electrophoresis separations 224 for further selectivity and specificity. Products of different fragment lengths are produced by bioinformatic primer design and discriminated by microchannel electrophoretic separation and fluorescent emission—allowing for increased multiplexing of the PCR reactions with confirmation and identification of true positives by fragment sizing. At least 96 bioprocessor units are radially place on a microchip 225 (FIG. 18). A 96 channel microchip operates for 4 days using a single channel per hour.

12. EXPAR Reactions Performed in a NanoBioProcessor

EXPAR is a rapid isothermal method for specifically amplifying short segments of DNA at 60° C. using oligonucleotide sequences, a thermal stable polymerase, and nicking enzymes. The products are detected by fluorescence or MS. The EXPAR reactions can be implemented in the NanoBioProcessor for genetic testing, gene expression measurements, molecular diagnostics, biodefense and other applications.

The reaction mix is added to the sample in a single step, and the thermal stable polymerase and nicking enzymes perform like most other proteins in microchannels. EXPAR is performed in the microchips shown in FIG. 15 or 20 after minor adaptations or in the microchip shown in FIG. 13. The nucleic acid, DNA or RNA, is moved in a microchannel such as the one labeled IMS input 250, using MOV pumps 251 into a chamber and then the single reaction mix added from one of the reagent channels 252. Fluidic circuits are used for adding one of more reactants to a reaction chamber 253. The temperature of the reaction chamber is optionally controlled. Following reaction, the processed sample is pumped using the MOV pumps into a reservoir or tube 254 for analysis by off-chip MS or analyzed on-microchip by fluorescence, chemiluminescence or other detection methods. In addition to single channels for analysis, samples can be split into many channels using the MOV routers and followed by multiple-EXPAR.

13. RiboMaker Reactions Performed in a NanoBioProcessor

The RiboMaker detection systems is based upon abortive initiation of RNA polymerase (RNAP) transcription, termed Abscription™, using Artificial Promoter Complexes (APCs) and nucleotide analogs called RiboLogs™. The APCs provide an initiation site for RNAP polymerase to generate 50-450 trinucleotide abortive products/min/site. Detection can be by MS analysis, fluorescence, chemiluminescence, or other methods well known to one skilled in the art. For DNA or RNA analysis, the APCs can have flanking sequences that provide specificity for the target site probe. RiboLogs with different mass units can identify which site is bound. By binding multiple APCs to different portions of a sequence to be interrogated, a fingerprint of RiboLogs can provide additional specificity information for biodefense, which can help eliminate false positives and false alarms. For proteins, an APC unit can be linked to an antibody. The RiboMaker detection is claimed to be fast, linear, and less sensitive to inhibition than PCR.

Figure 13:
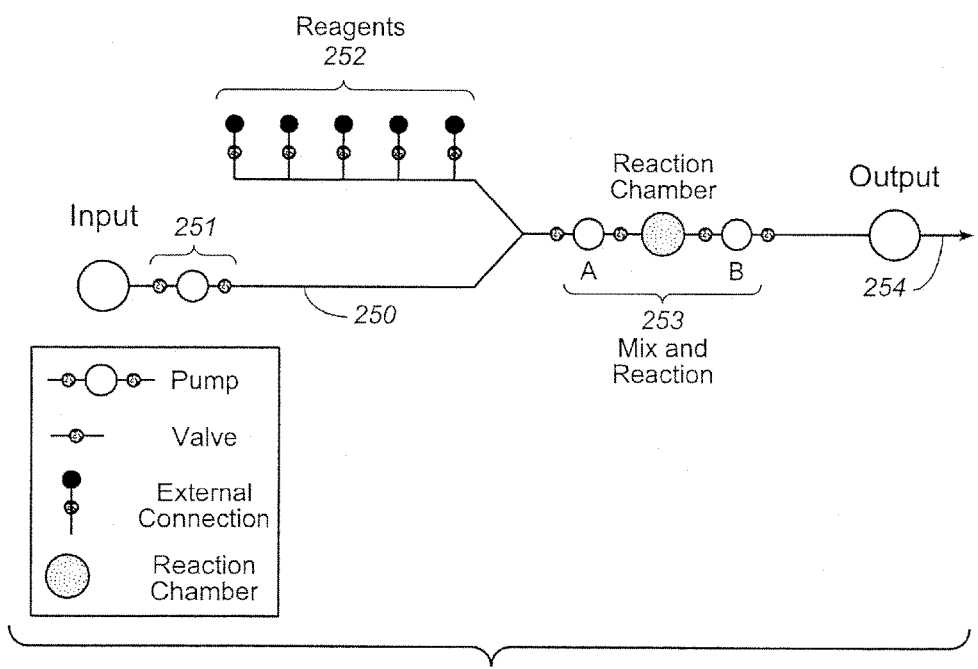
FIG. 13 illustrates an embodiment of a fluidic circuit for adding one or more reactants to a reaction chamber.

The RiboMaker reaction is accomplished on a NanoBioProcessor microchip such as the one in FIG. 13. The addition of a single APC reagent followed by single reaction mix requires two mixing steps. If the RiboMaker sample is captured on a bead, the bead is through the IMS Input (FIG. 13) into the reaction chamber, which optionally has a weir or magnet to trap the bead. The APCs are added using one of the reagent channels. The RiboLogs are added from a second reagent channel. If necessary, the reaction is moved back and forth between pumps A and B.

14. Microchip CMS Array Design

Figure 23:
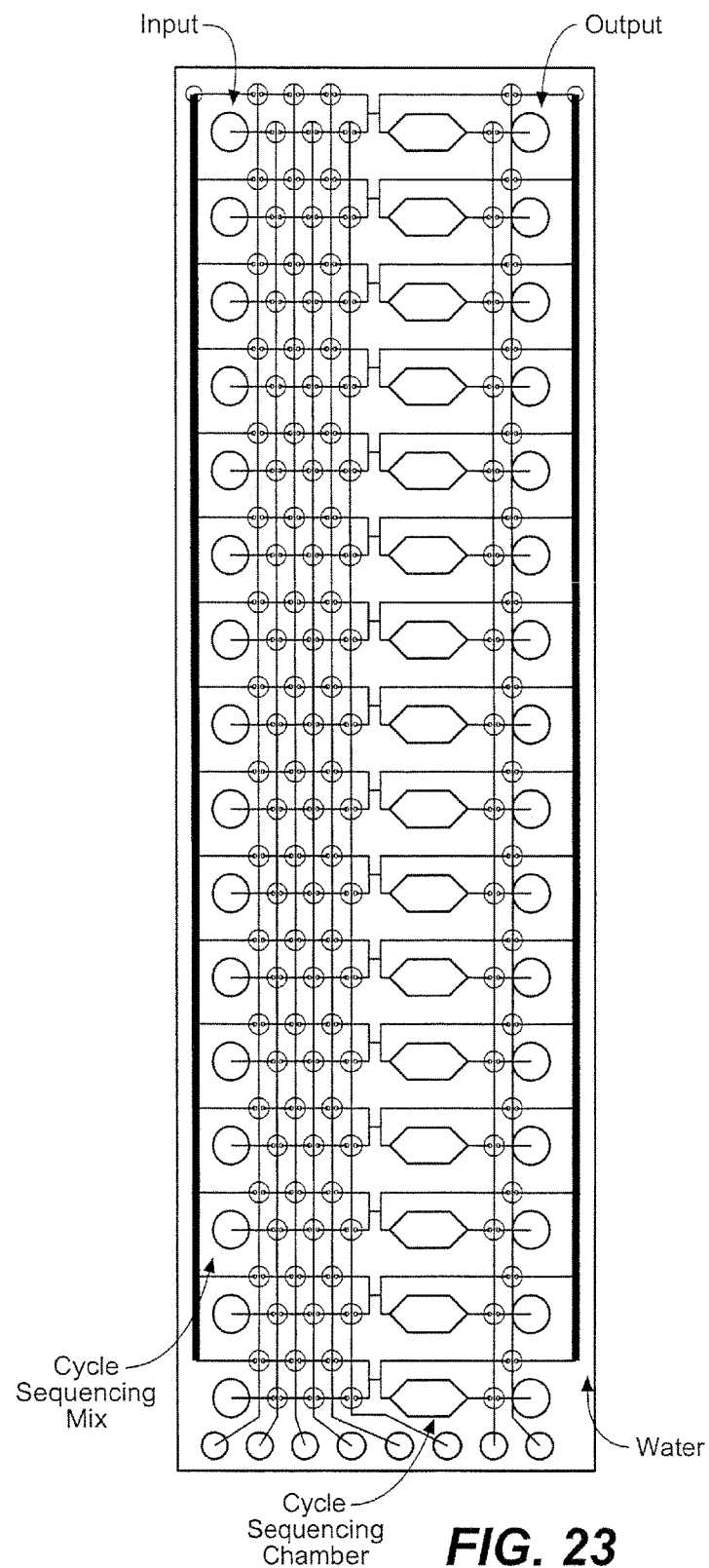
FIG. 23 illustrates an embodiment of a 16-channel 200 nL cycle sequencing module microchip.

An embodiments of a 16 channel microchip 270 is shown in FIG. 23. The actuation lines 271 for the valves and pumps are shown running vertically and terminating at vias on the bottom of the microchip where external actuation lines can be connected. The cycle sequencing mixture is supplied via a syringe pump to a channel 272 on the left and water or buffer to regenerate the microchip is supplied in a channel 273 on the right. Both these "service" channels are multiplexed to feed all 16 channels and have on-chip pumps or valves 274 respectively to control the flow. This microchip is constructed as a four layer device from glass wafers and PDMS membrane.

15. A Complete MINDS System

To create the complete MINDS System, the instrumentation from the Core MINDS system is modified: 1) A bead service channel is added and interfaced with a bead sorting method to deliver individual beads; 2) The resistive heater design and electrode ring on the microchip interface device is altered to the microchip; 3) Microchip modifications to ensure that single beads are loaded and unloaded repeatedly.

Figure 24:
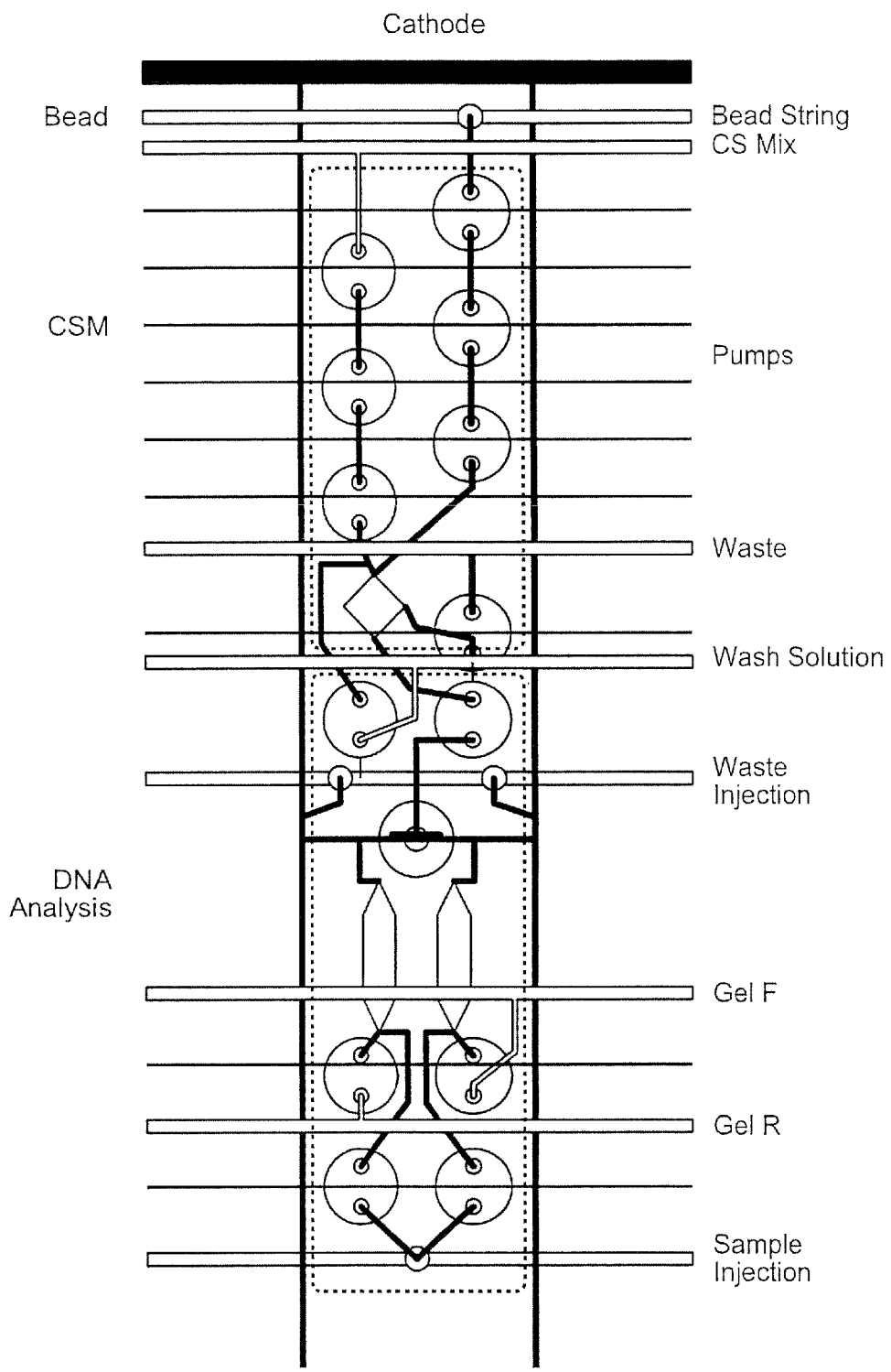
FIG. 24 illustrates an embodiment of a microbead-feed integrated sample, preparation, cleanup, and analysis MINDS microchip repeat unit. A 25 nL sample preparation chamber is shown with two affinity capture and separation channels.

A design of a MINDS microchip is shown in FIG. 24. The microchip is similar to the Core MINDS microchip shown in FIG. 22 except that a bead service channel leads 330 to the input line, the sample volume is decreased 4-fold to 25 nL, and a weir is formed in the cycle sequencing chamber to trap the bead. Single beads are input through the Input channel. The weir is etched to only 2 µm, which requires an additional mask and fabrication steps.

The single bead is pumped into the cycle sequencing chamber with only the channel leading towards the electrode and to the affinity capture chambers flowing. The weir stops the movement of the bead. Once a bead is loaded, 25 nL of cycle sequencing mixture with primers for both forward and reverse paired-end reads are pumped by on-chip pumps into the reaction chamber. The valves adjacent to the chamber are closed and the temperature cycled. Following cycling, the cycle sequencing products in the cycle sequencing mixture are pumped into electrode reservoir 6, electrophoresed into two sample cleanup chambers, and processed essentially as described above, with each paired-end read injected into separate separation channels. The valve leading to waste is opened and the bead flushed into the waste channel by the wash line. The separation regeneration occurs as described above.

Single beads are fed into each channel by 1) manipulating a microfluidic string of beads, that are well separated, and moving them into each channel serially or in parallel, 2) feeding from a 'bin" of beads in each channel and dispensing them one at a time into the cycle sequencing reactor, or 3) magnetically manipulating individual beads or pickup onto the end of capillaries for "pick-and-place" manipulation. For the string of beads approach, beads are well separated spatially from the next by a bolus of liquid, possibly immiscible such as Fluorinert (3M). We have previously successfully used boluses of Fluorinert in cycle sequencing and PCR reactions. The bead string is moved together into rough positions. A valve then closes on the circulating bead service channel, and flow is diverted through an individual cycle sequencing chamber long enough to move the bead into the loading channel. A valve on the loading channel is closed, the valve on the bead service channel opened, and the next bead is placed into the next channel. Parallel variations are also possible and can minimize loading time. Optical bead sensors can also assist in helping regulate timing and feed flows.

The MINDS system use valves and pumps with laser drilled test holes of 50 μm to decrease pump volumes of several nanoliters. Alternately, valves with 250 μm holes are partially opened with partial "strokes" on each cycle. The valves surrounding the chambers are pulsed to move the bead in the chamber or external ultrasonic mixing is applied. Surface interactions are ameliorated by additives with surface modifications applied as needed.

Figure 44:
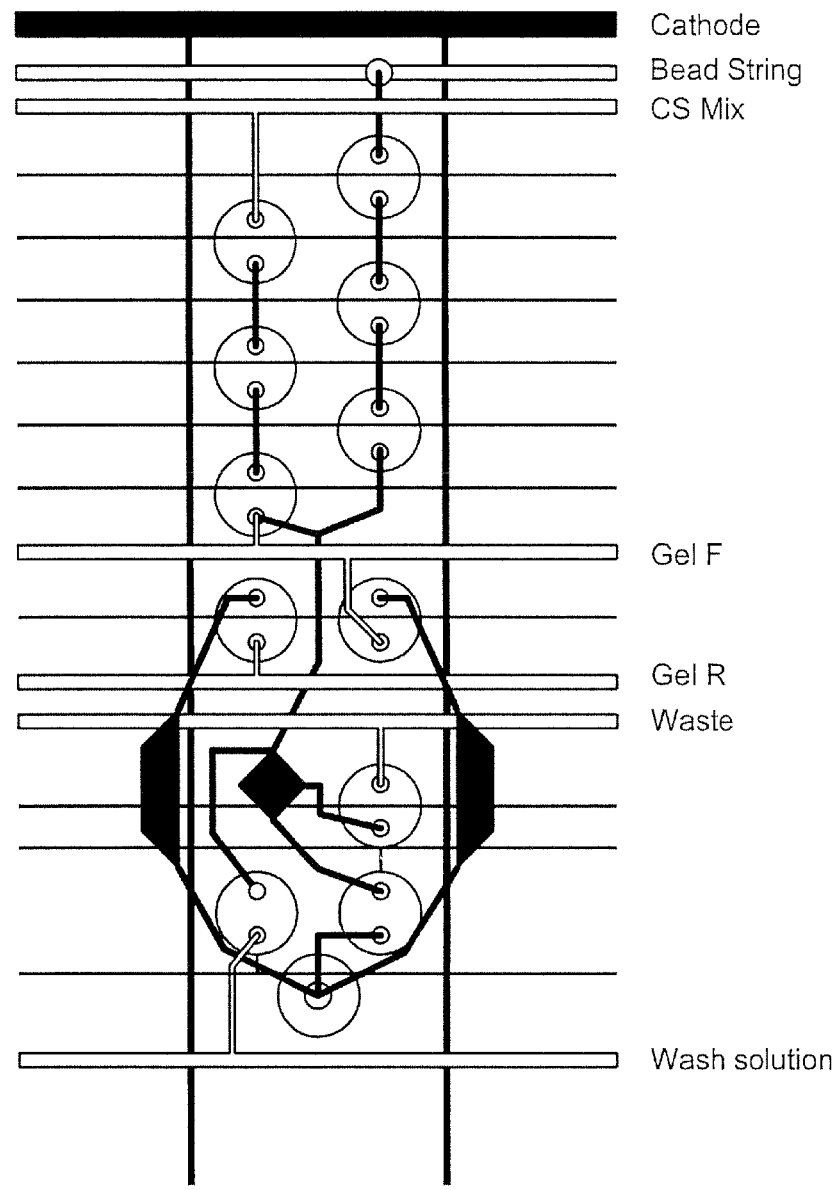
FIG. 44 shows an embodiment of a direct injection scheme with sample cleanup directly injecting into separation channels.

For direct injection, the sample cleanup matrix is positioned in line with the separation channel. As shown in FIG. 44, this design has the familiar elements of cycle sequencing chamber for a bead and sample cleanup except the sample cleanup chambers are moved to the cathode side of the separation channel. Cycle sequencing samples are be electrophoresed on the sample cleanup matrix and contaminants removed into the cathode chamber which is flushed if needed. The clean samples are in a sharpened band on the sample cleanup matrix, and are released by heating the chambers and separations started. This volumetrically injects a sharp band onto the separation channel. Therefore, all of the sample collected on each sample cleanup matrix is analyzed as opposed to the "heart cut" found in typical twin T injections where the loading of the twin T only allows a fraction of the sample to be analyzed.

16. Mixing with on-chip MOV Devices

A four-layer microchip was used to demonstrate mixing with the on-chip MOV devices. The mixing demonstration used the three different designs of mixers that we had fabricated on the MBI-13 microchip—bolus mixing, router mixing, and "T" mixing. Water and Brilliant Red dye solution were mixed These designs used either (1) two opposing MOV pumps (FIG. 45), (2) two opposing MOV pumps with a third pump to create boluses separated by air, and (3) using a router to mix two streams. All chip mixing designs showed a good mixing of clear water and red dye solution. During the pumping sequence we observed a movement back and forth of the portion of liquid exiting the last valve. The last valve aspirates a volume of the liquid from the channel, because the channel is opened. This movement produced good mixing inside the valve.

Figure 46:
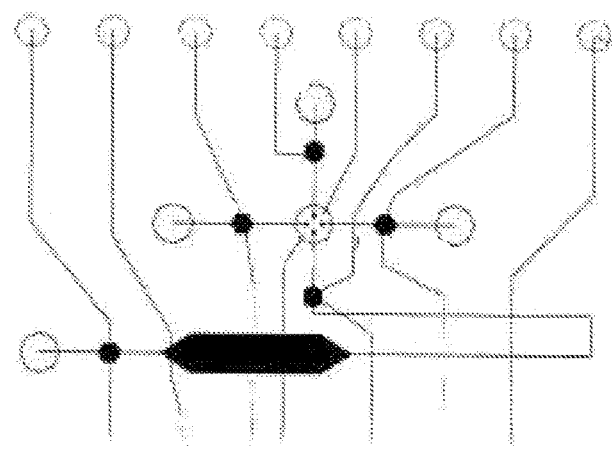
FIG. 46 shows an embodiment of mixing with on-chip MOV pumps on MBI-13 T-channels and boluses.

The structure presented in FIG. 46 was used to generate boluses. The MOV router formed by the five valves pumps reagents from two wells (labeled 1 and 3) and air from well 2 into the blue reaction chamber to form boluses separated by air. Various papers have shown good mixing inside a bolus, driven by the shearing forces of the walls creating mixing inside the bolus as the material contacting the wall is slowed. In our case the mixing was aided by the back and forth movement of the two reagents into the air channel, during multiple pumping steps. By using two solutions, one with a dye and the other simply water, no color variation was seen by the time the bolus reached the reaction chamber.

Figure 45:
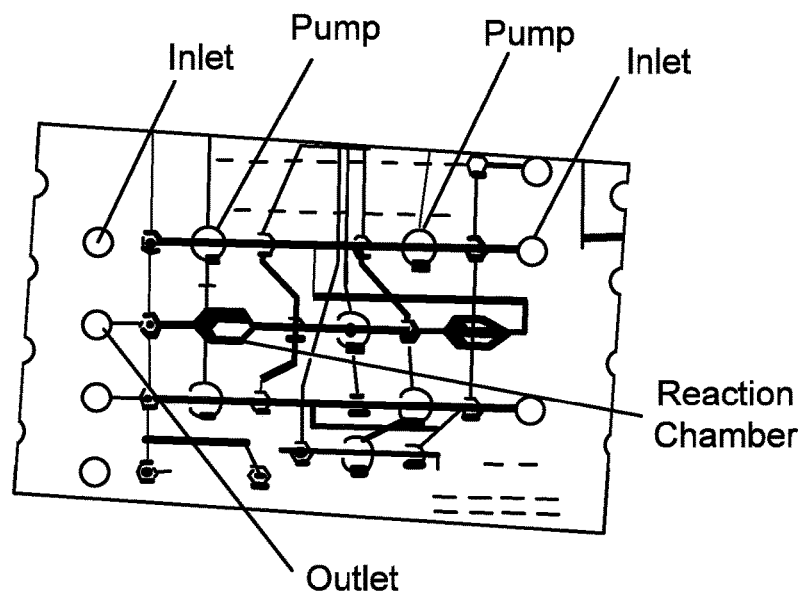
FIG. 45 shows an embodiment of mixing on-chip with MOV devices.

FIG. 45 shows an exemplary chip design for bolus and router mixing. Mixed liquid/air boluses were generated by pumping water from port 1, air from port 2 and red dye from port 3. No difference in color was observed across the reaction chamber. The mixing of reagents 1 and 3 in the router was studied by keeping port 2 closed. In each pumping cycle, water and dye enter the router in a laminar flow mode (the router appears half white and half red) and mixing starts in the exit valve and at the beginning of the channel. The next pumping cycle aspirates back from the channel a volume equal to that of the exit valve when it opens. This back and forth movement inside the exit valve produces a very efficient mixing effect. Again no color differences were seen across the reaction chamber—consistent with uniform mixing, at least at the microscopic scale.

Figure 47:
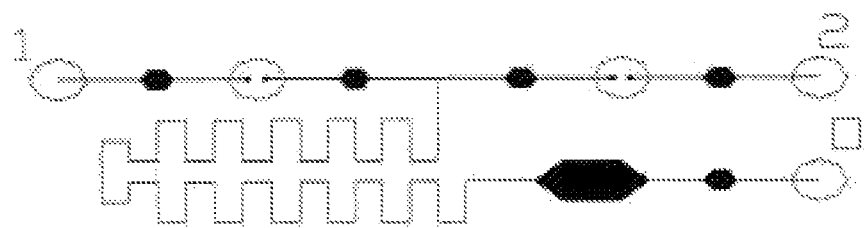
FIG. 47 shows an embodiment of a chip design for "T" mixing in which water was pumped from Port 1 and red dye was pumped from Port 2. Substantial mixing was observed a few millimeters from the "T" junction and no color difference was seen across the 2 mm reaction chamber.
Figure 48:
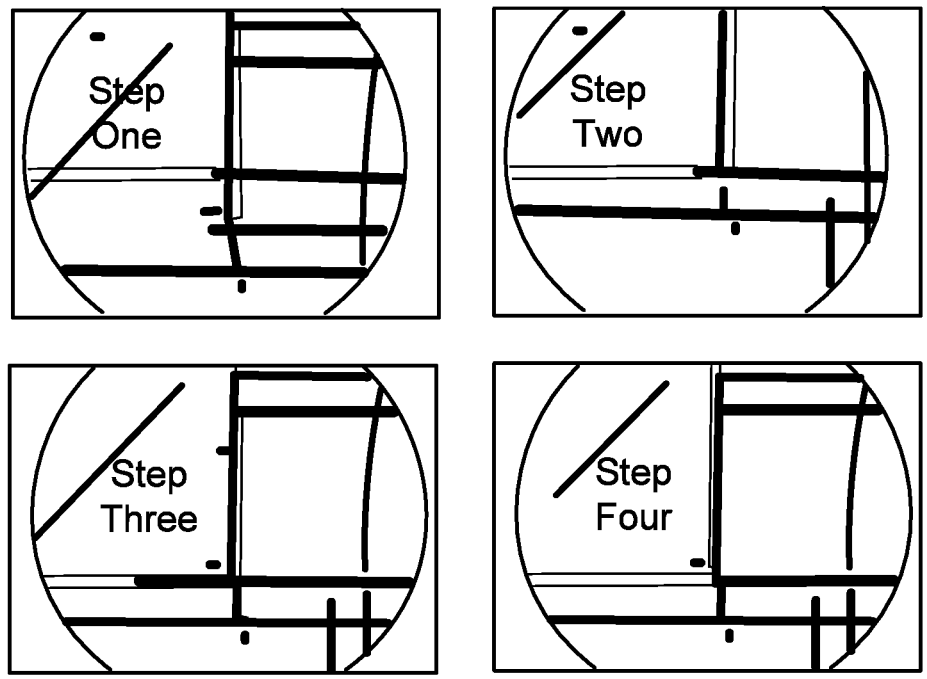
FIG. 48 shows images of an embodiment of a "T" channel junction during a four-step pumping sequence in which the timing was 1 second for each step. Channel dimensions were 50 µm deep and 150 µm wide. The pump valve volume was about 50 nL.

FIG. 47 shows an exemplary chip design for "T" mixing. Good mixing was observed a few mm from the "T" junction, due to a "back and forth" movement inside the pump exit valves. No color difference was seen across the 2 mm reaction chamber. For a better understanding of this special "T" mixing, the following movie frames (FIG. 48) illustrates the process. The inlet valves open and the outlet valves close in step 1 (mixed solution is pushed into the main channel). Pump valves are opening in step 2 (more diffusion of red dye in water can be seen). The inlet valves close and the outlet valves open in step 3 (a plug of semi-mixed solution is aspirated back from the main channel). The pump valves close in step 4 (new solution slugs are pushed and laminar flow can be seen in the main channel).

Figure 49:
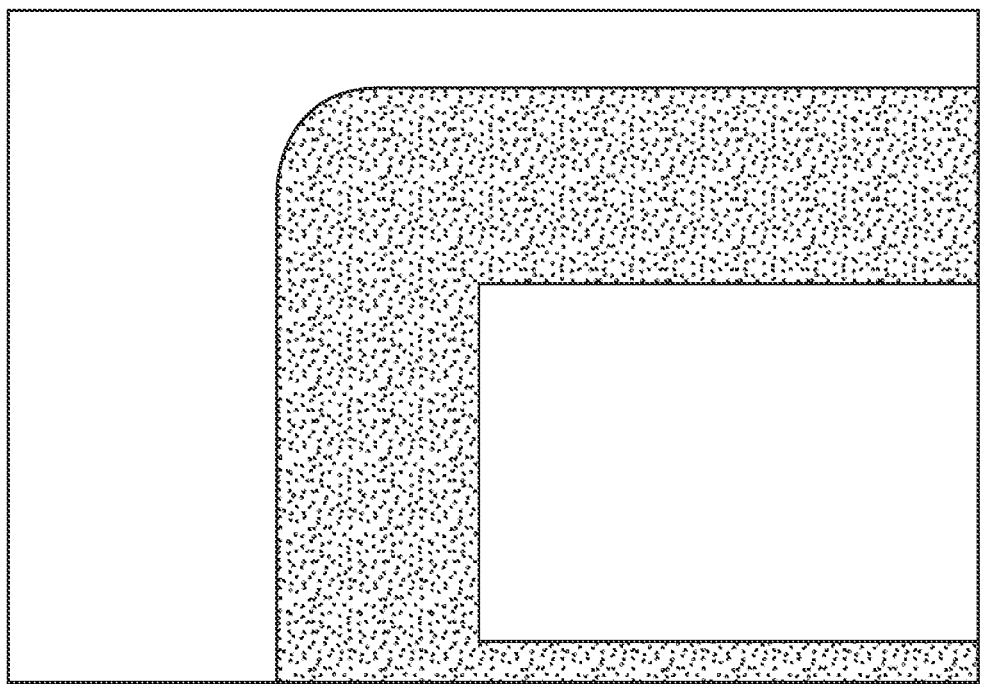
FIG. 49 shows a close-up image taken in pumping step 3 a few millimeters downstream from the "T" junction. Channel width was 150 µm. Uniform color consistent with substantial mixing is apparent.

The backflow of mixed liquid in step 3 (due to opening of outlet valves) helps to achieve good mixing. FIG. 49 shows a close up picture of uniform solution color a few mm downstream from the "T" junction.

All three tested MOV mixing strategies produced good mixing, due to the "back and forth" movement of fluid induced by this type of pumping system. Bolus mixing produced bubbles in the reaction chambers, which may be detrimental to achieving good reactions. Just a few mm of 150 μm channel (downstream from the junction) are enough to achieve good mixing. In the Gen II design, we decided to use MOV mixing with the new Ionian NEA assay to mix reagents and samples on chip, perform the reactions, and stop the reactions with MOV mixing.

What is claimed is:

1. A traveling magnetic wave flow through device, comprising:
   a rotating pole piece;
   a flow through tube;
   a magnetic fixed piece; and
   at least one bead positioned in the lumen of said flow through tube, wherein said flow through tube is in fluidic communication with a microfluidic device, and wherein said rotating pole piece is configured to produce a travelling magnetic wave down said flow through tube upon rotation of said rotating pole piece.

2. The device of claim 1, wherein the rotation of said rotating pole piece is at least about 100 Hz.

3. The device of claim 1, wherein said flow through tube is adjacent to said rotating pole piece.

4. The device of claim 3, wherein said flow through tube is axially parallel to said rotating pole piece.

5. The device of claim 3, wherein said flow through tube is fluidically separated from said rotating pole piece.

6. The device of claim 1, further comprising wherein said at least one bead comprises a plurality of beads positioned in the lumen of said flow through tube.

7. The device of claim 6, wherein said plurality of beads comprises magnetic beads.

8. The device of claim 7, wherein said rotation of said rotating pole piece produces acceleration of said magnetic beads to lyse target analytes flowing through said flow through tube.

* * * * *